US011938179B2

(12) United States Patent
Tian et al.

(10) Patent No.: US 11,938,179 B2
(45) Date of Patent: *Mar. 26, 2024

(54) **METHODS AND COMPOSITIONS FOR INDUCING IMMUNE RESPONSES AGAINST *CLOSTRIDIUM DIFFICILE***

(71) Applicant: Novavax, Inc., Gaithersburg, MD (US)

(72) Inventors: Jing-Hui Tian, Germantown, MD (US); Ye Liu, Clarksville, MD (US); Gale Smith, Germantown, MD (US); Gregory Glenn, Poolesville, MD (US); David Flyer, Olney, MD (US)

(73) Assignee: Novavax, Inc., Gaithersburg, MD (US)

( * ) Notice: Subject to any disclaimer, the term of this patent is extended or adjusted under 35 U.S.C. 154(b) by 24 days.

This patent is subject to a terminal disclaimer.

(21) Appl. No.: 17/398,610

(22) Filed: Aug. 10, 2021

(65) Prior Publication Data

US 2022/0211834 A1 Jul. 7, 2022

Related U.S. Application Data

(63) Continuation of application No. 16/494,517, filed as application No. PCT/US2018/022597 on Mar. 15, 2018, now Pat. No. 11,123,419.

(60) Provisional application No. 62/474,434, filed on Mar. 21, 2017, provisional application No. 62/471,636, filed on Mar. 15, 2017.

(51) Int. Cl.
*A61K 39/116* (2006.01)
*A61K 39/00* (2006.01)
*A61K 39/39* (2006.01)

(52) U.S. Cl.
CPC ............ *A61K 39/116* (2013.01); *A61K 39/39* (2013.01); *A61K 2039/55577* (2013.01); *A61K 2039/70* (2013.01)

(58) Field of Classification Search
None
See application file for complete search history.

(56) References Cited

U.S. PATENT DOCUMENTS

| 11,123,419 | B2 | 9/2021 | Tian et al. |
|---|---|---|---|
| 2012/0282293 | A1 | 11/2012 | Galen |
| 2015/0328305 | A1 | 11/2015 | Smith et al. |
| 2020/0085934 | A1 | 3/2020 | Tian et al. |

FOREIGN PATENT DOCUMENTS

| CN | 105120892 A | 12/2015 |
|---|---|---|
| CN | 105682679 A | 6/2016 |
| CN | 106220737 A | 12/2016 |
| JP | H10508301 A | 8/1998 |
| JP | 2014530010 A | 11/2014 |
| JP | 2015506948 A | 3/2015 |
| JP | 2016502551 A | 1/2016 |
| JP | 2016504993 A | 2/2016 |
| JP | 2016518374 A | 6/2016 |
| WO | WO-9611711 A1 | 4/1996 |
| WO | WO-2010017383 A1 | 2/2010 |
| WO | WO-2011060431 A2 | 5/2011 |
| WO | WO-2013112867 A1 | 8/2013 |
| WO | WO-2014086787 A1 | 6/2014 |
| WO | WO-2015063647 A1 | 5/2015 |
| WO | WO-2015197737 A1 | 12/2015 |

OTHER PUBLICATIONS

Devera, T.S. et al., "Memory B Cells Encode Neutralizing Antibody Specific for Toxin B from the Clostridium difficile Strains VPI 10463 and NAP1/BI/027 but with Superior Neutralization of VPI 10463 Toxin B," Infection and immunity, 2016, vol. 84(1), pp. 194-204.
Extended European Search Report issued by the European Patent Office for Application No. 18767173.0, dated Nov. 24, 2020, 8 pages.
Heinrichs et al., "Design, Production and Pre-Clinical Evaluation of a Novel Toxin-Based Vaccine for the Prevention of Clostridium Difficile Disease," 4th International Clostridium Difficile Symposium, Sep. 20, 2012 (Sep. 20, 2012), p. 30, XP055149657, Retrieved from the Internet: URL:http://www.icds.si/icds-2012/docs/abstract book.pdf [retrieved on Oct. 29, 2014], 226 pages.
International Search Report and Written Opinion issued by the International Searching Authority for Application No. PCT/US2018/022597, dated Aug. 31, 2018, 12 pages.
Bowie, J. U. et al., "Deciphering the message in protein sequences: Tolerance to amino acid substitutions," Science, (Mar. 16, 1990), 247(4948):1306-1310.
Burgess, W. H. et al., "Possible dissociation of the heparin-binding and mitogenic activities of heparin-binding (acidic fibroblast) growth factor-1 from its receptor-binding activities by site-directed mutagenesis of a single lysine residue," The Journal of Cell Biology, (Nov. 1990), vol. 111, No. 5, pp. 2129-2138.
Lazar, E. et al., "Transforming Growth Factor Alpha: Mutation of Aspartic Acid 47 and Leucine 48 Results in Different Biological Activities," Molecular and Cellular Biology, Mar. 1988, vol. 8, No. 3, pp. 1247-1252.

*Primary Examiner* — Brian Gangle
(74) *Attorney, Agent, or Firm* — COOLEY LLP

(57) ABSTRACT

Disclosed herein are methods and compositions for treating or preventing bacterial infection. In particular, the methods and compositions are directed towards *C. difficile* infection. In particular aspects, the compositions are vaccines containing multimeric polypeptides containing portions of multiple toxins from bacteria. The polypeptides induce effective immune responses thus treating or preventing infection.

20 Claims, 33 Drawing Sheets
Specification includes a Sequence Listing.

**Fig. 1: *C. difficile* triple toxin vaccine constructs**

Triple toxin 1420

CDTb

| Activation domain | Mature CDTb | TcdB RBD | TcdA(R19)RBD |

RARRRKKR
With a furin cleavage site

Mol Wt: 206,421

Triple toxin 1470

CDTb

| Activation domain | Mature CDTb | TcdB RBD | TcdA(R19)RBD |

Mol Wt: 205,312

Fig. 2: Expression and solubility of triple toxin vaccine BV1470 and BV1420

Fig. 3: Time course expression of triple toxin vaccine BV1470 and BV1420

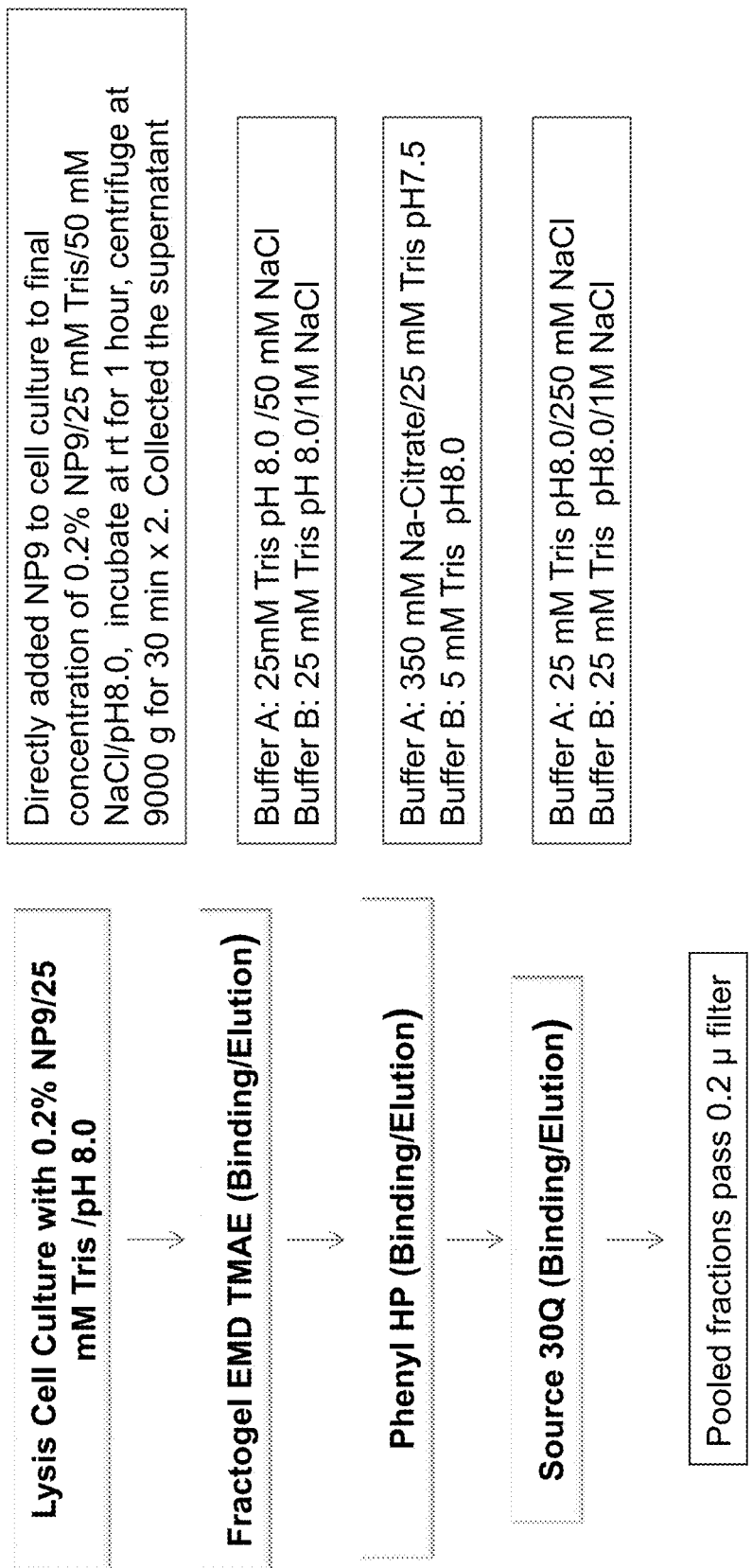
Fig. 4: Purification of triple toxin vaccine

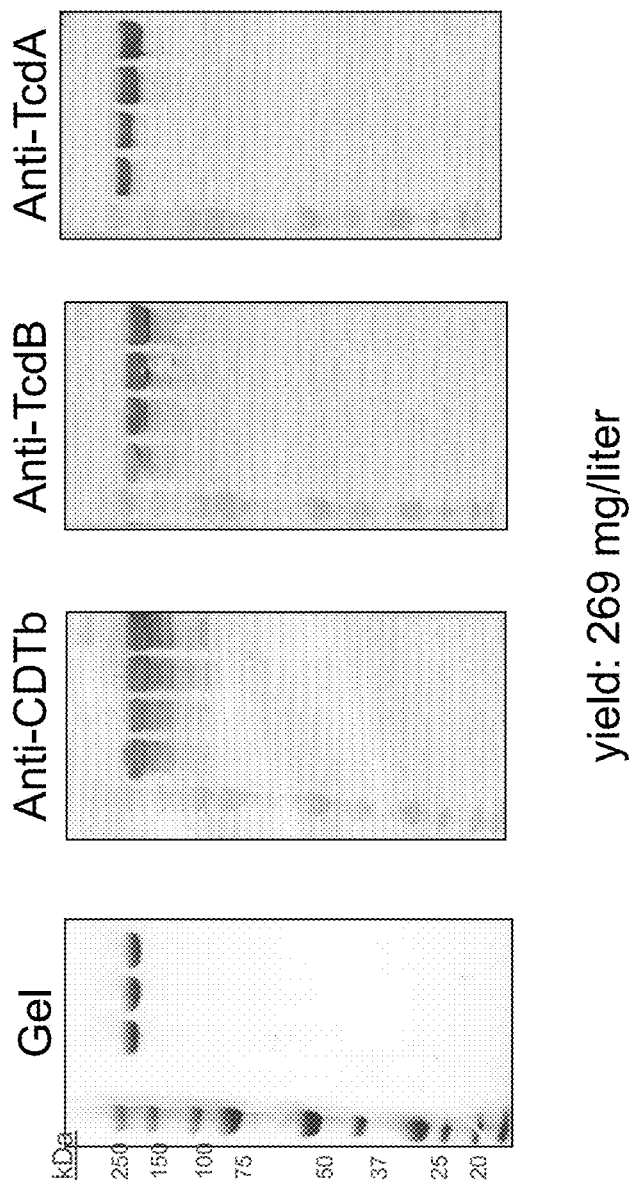

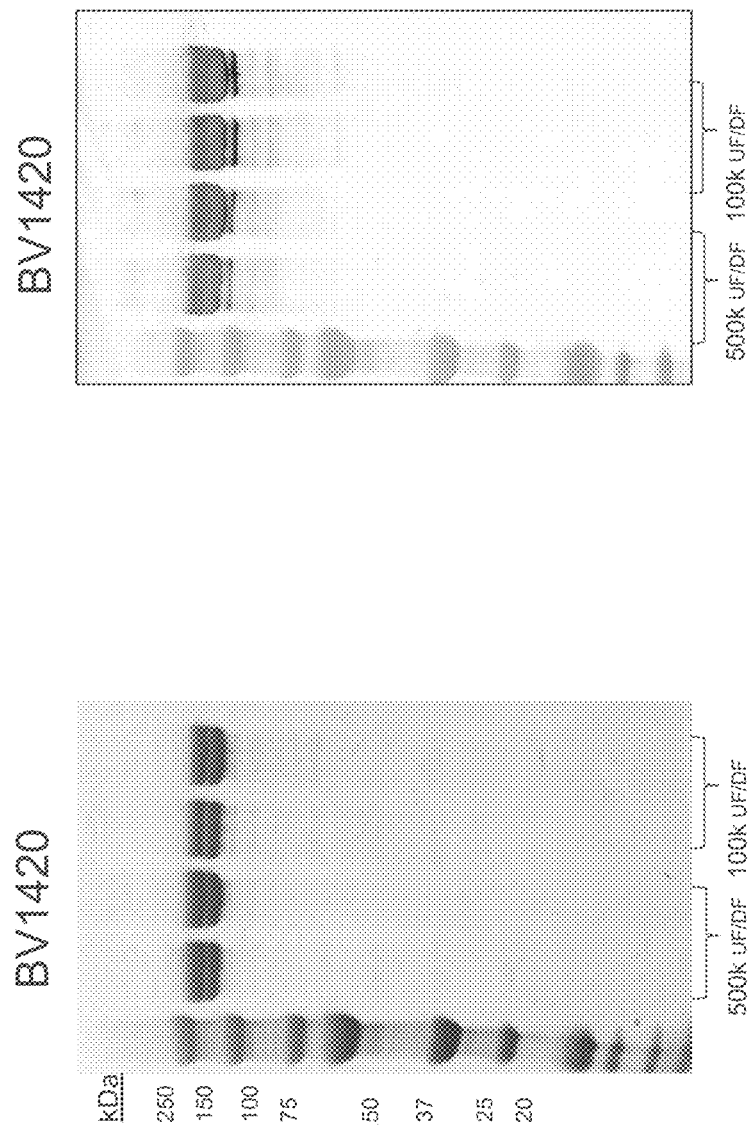

Fig. 7: Particle size distribution by volume graph for triple toxin BV1420

| | Diam. (nm) | % Volume | Width (nm) |
|---|---|---|---|
| Peak 1: | 15.95 | 99.8 | 7.006 |
| Peak 2: | 298.8 | 0.1 | 120.3 |
| Peak 3: | 4235 | 0.1 | 1041 |

Z-Average (d.nm): 30.62
PdI: 0.391
Intercept: 0.906
Result quality: Good

Fig. 8: Particle size distribution by intensity graph for triple toxin BV1470

| # of runs | Zave (nm) | %CV | PDI ave |
|---|---|---|---|
| 6 | 17.7 | 4.0 | 0.243 |

Size Distribution by Intensity

Intensity (Percent) vs Size (d.nm)

Attenuator: 9

|  | Size (d.nm): | % Intensity: | St Dev (d.nm): |
|---|---|---|---|
| Peak 1: | 17.84 | 92.3 | 6.148 |
| Peak 2: | 558.7 | 4.2 | 341.0 |
| Peak 3: | 4210 | 3.5 | 1134 |

Z.Average (d.nm): 17.66
PdI: 0.243
Intercept: 0.934
Result quality: Good

Fig. 9A: Electronmicrographs of negative stained triple toxin BV1420

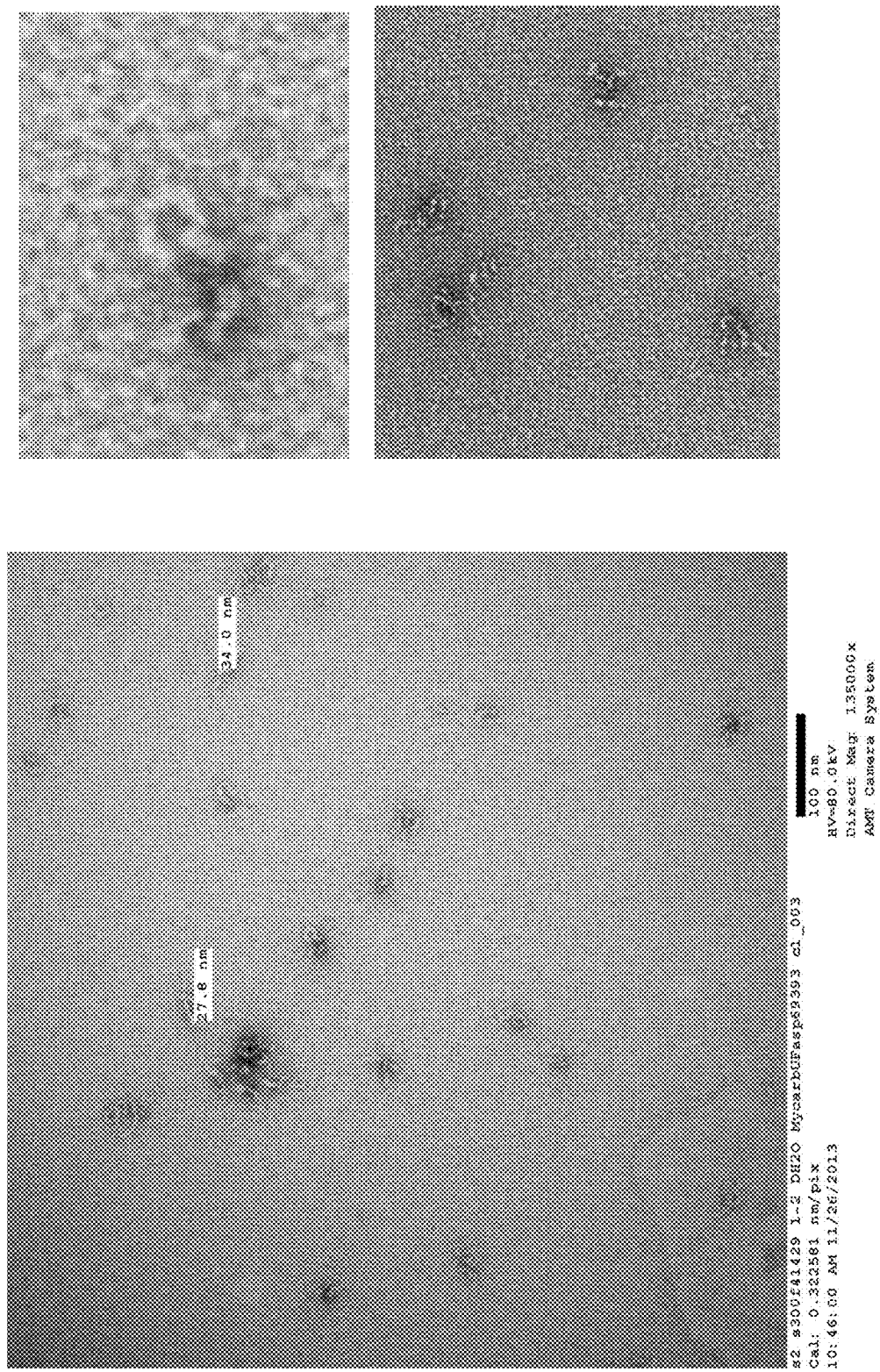

Fig. 10: BV1420 triple toxin vaccine mouse lethal toxin challenge study 1

| Gp | Antigen | Adjuvant (µg) | Dose (µg) | N | Day Immun | Bleed | Challenge day 35 | Terminal Bleed |
|---|---|---|---|---|---|---|---|---|
| 1 | BV1420 | Alum OH 50.0 | 30.0 | 8 | 0, 14 | 0, 14, 32 | Toxin A | 42 |
| 2 | BV1420 | Alum OH 50.0/ Matrix M 5.0 | 30.0 | 8 | 0, 14 | 0, 14, 32 | Toxin A | 42 |
| 3 | PBS | | | 8 | 0, 14 | 0, 14, 32 | Toxin A | 42 |
| 4 | BV1420 | Alum OH 50.0 | 30.0 | 8 | 0, 14 | 0, 14, 32 | Binary Toxin | 42 |
| 5 | BV1420 | Alum OH 50.0/ Matrix M 5.0 | 30.0 | 8 | 0, 14 | 0, 14, 32 | Binary Toxin | 42 |
| 6 | PBS | | | 8 | 0, 14 | 0, 14, 32 | Binary Toxin | 42 |

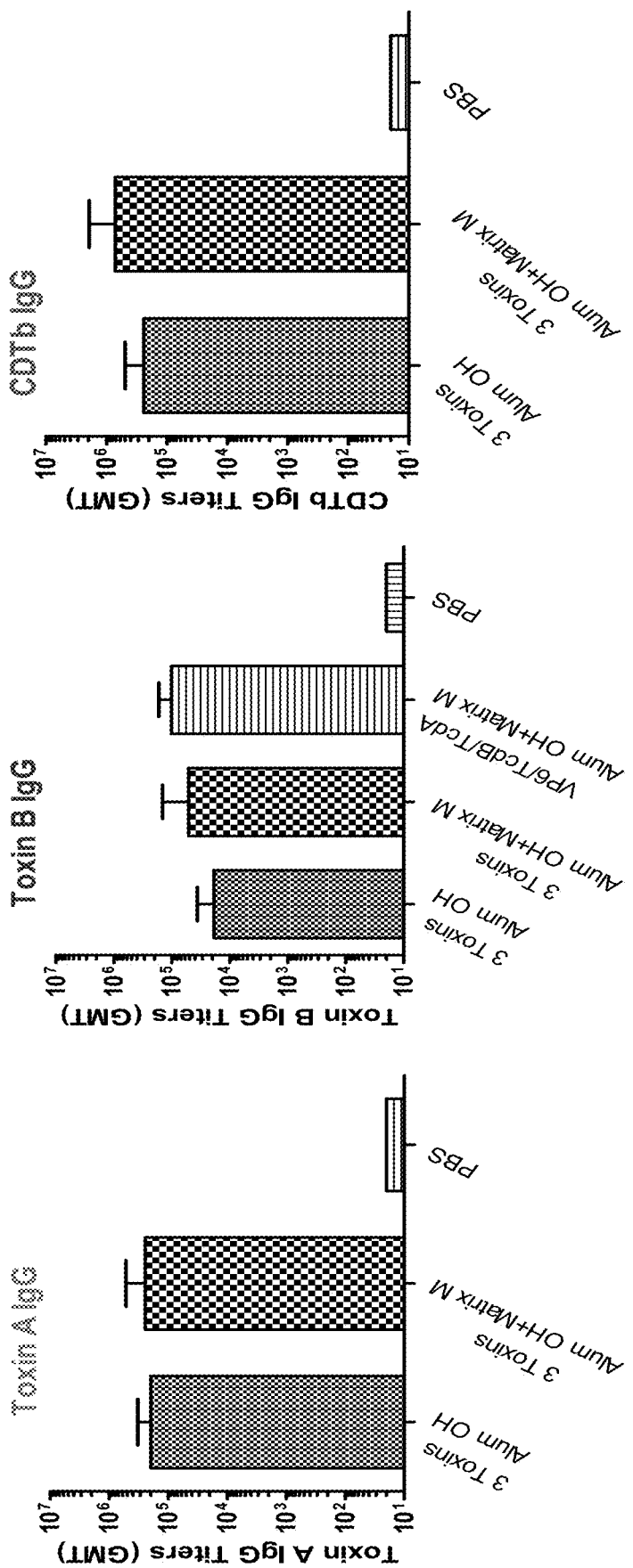
Fig. 11: BV1420 triple toxin vaccine mouse lethal toxin challenge study 1
Serum IgG responses

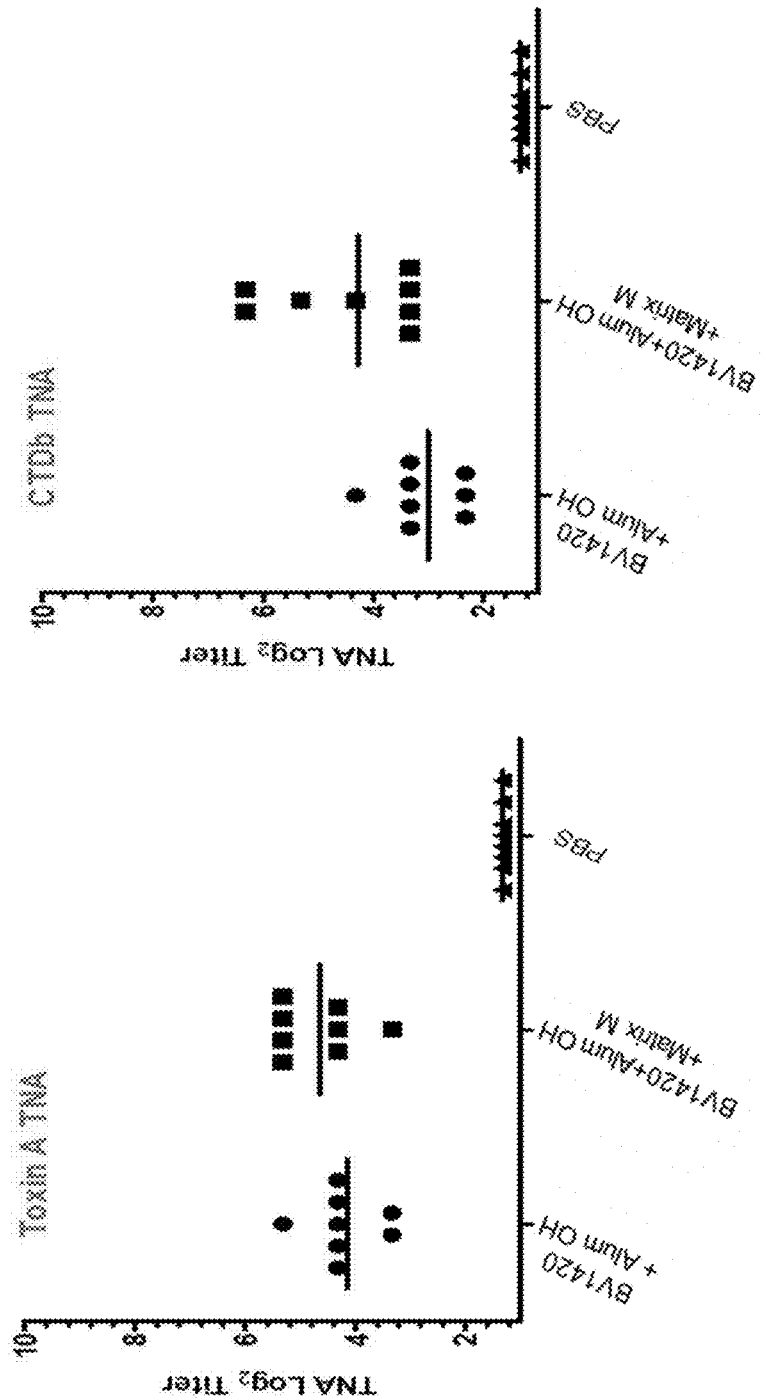
Fig. 12: BV1420 triple toxin vaccine mouse lethal toxin challenge study 1 toxin neutralizing antibody ( Fig. 13: BV1420 triple toxin vaccine mouse lethal toxin challenge study 1 animal survival

| Gps | Antigen | Adjuvant (ug) | Toxin | 1/6/14 Survivor | 1/7/14 Survivor | 1/8/14 Survivor | 1/9/14 Survivor | 1/10/14 Survivor | 1/11/14 Survivor | 1/12/14 Survivor | 1/13/14 Survivor | Survival % |
|---|---|---|---|---|---|---|---|---|---|---|---|---|
| 1 | BV1420 | Alum OH 50.0 | Toxin A | 8 | 8 | 8 | 8 | 8 | 8 | 8 | 8 | 100% |
| 2 | BV1420 | Alum OH 50.0/ Matrix M 5.0 | Toxin A | 8 | 8 | 8 | 8 | 8 | 8 | 8 | 8 | 100% |
| 3 | PBS | NA | Toxin A | 8 | 7 | 0 | 0 | 0 | 0 | 0 | 0 | 0% |
| 4 | BV1420 | Alum OH 50.0 | Binary Toxin | 8 | 8 | 8 | 8 | 8 | 8 | 8 | 8 | 100% |
| 5 | BV1420 | Alum OH 50.0/ Matrix M 5.0 | Binary Toxin | 8 | 8 | 8 | 8 | 8 | 8 | 8 | 8 | 100% |
| 6 | PBS | NA | Binary Toxin | 8 | 3 | 2 | 2 | 2 | 2 | 2 | 2 | 25% |

Fig. 14: BV1420 triple toxin vaccine mouse lethal toxin challenge study 2

| Gp | N | Antigen | Adjuvant (µg) | Dose (µg) | Day Immun. | Bleed | Challenge day 35 | Terminal bleed |
|---|---|---|---|---|---|---|---|---|
| 1 | 20 | BV1420 | Alum OH | 30.0 | 0, 14 | 0, 14, 32 | Toxin B | 42 |
| 2 | 20 | BV1470 | Alum OH | 30.0 | 0, 14 | 0, 14, 32 | Toxin B | 42 |
| 3 | 20 | VP6/TcdB RBD | Alum OH | 10.0 | 0, 14 | 0, 14, 32 | Toxin B | 42 |
| 4 | 20 | BV1470 + VP6/TcdB RBD | Alum OH | 30+10 | 0, 14 | 0, 14, 32 | Toxin B | 42 |
| 5 | 20 | Toxoid B | Alum OH | 10 | 0, 14 | 0, 14, 32 | Toxin B | 42 |
| 6 | 20 | PBS | - | - | 0, 14 | 0, 14, 32 | Toxin B | 42 |

Fig. 15: BV1420 triple toxin vaccine mouse lethal toxin challenge study 2
Anti-toxin IgG levels All vaccine groups adjuvanted with Alum Fig. 16: BV1420 triple toxin vaccine mouse lethal toxin challenge study 2
Toxin B TNA titers All vaccine groups adjuvanted with Alum Fig. 17: BV1420 triple toxin vaccine mouse lethal toxin challenge study 2
Toxin B survival

| Gps | Antigen | Adjuvant (ug) | Toxin | Day 0 | Day 1 | Day 2 | Day 3 | Day 4 | Day 5 | Day 6 | Day 7 | Survival % |
|---|---|---|---|---|---|---|---|---|---|---|---|---|
| 1 | BV1420 | Alum OH 50.0 | Toxin B | Survivor | Survivor | Survivor | Survivor | Survivor | Survivor | Survivor | 4 | 67% |
| 2 | BV1470 | Alum OH 50.0 | Toxin B | 6 | 6 | 6 | 6 | 6 | 6 | 5 | 5 | 83% |
| 3 | VP6/TcdB RBD | Alum OH 50.0 | Toxin B | 6 | 6 | 6 | 6 | 6 | 5 | 5 | 5 | 83% |
| 4 | BV1470 + VP6/TcdB RBD | Alum OH 50.0 | Toxin B | 6 | 5 | 5 | 5 | 5 | 5 | 5 | 5 | 83% |
| 5 | Toxoid B | Alum OH 50.0 | Toxin B | 6 | 6 | 6 | 6 | 6 | 6 | 6 | 6 | 100% |
| 6 | PBS | NA | Toxin B | 6 | 1 | 1 | 0 | 0 | 0 | 0 | 0 | 0% |

Fig. 18: Alternative triple toxin vaccines

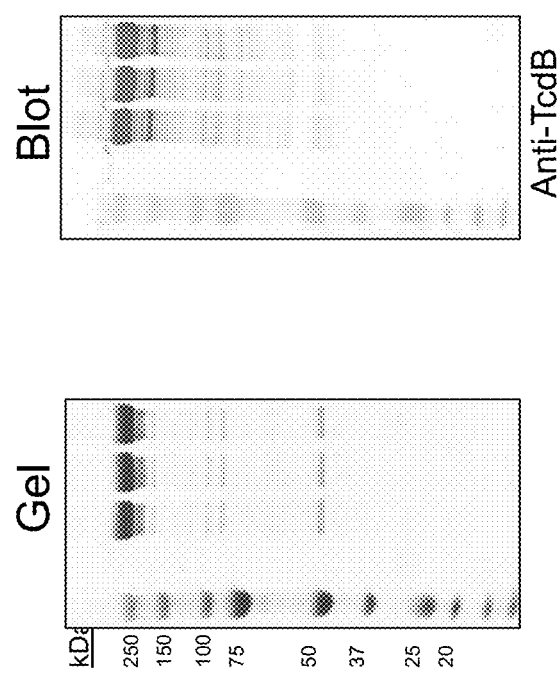
Fig. 19: Alternative triple toxin vaccine – BV1512 purified pCDTb/TD/TcdAR

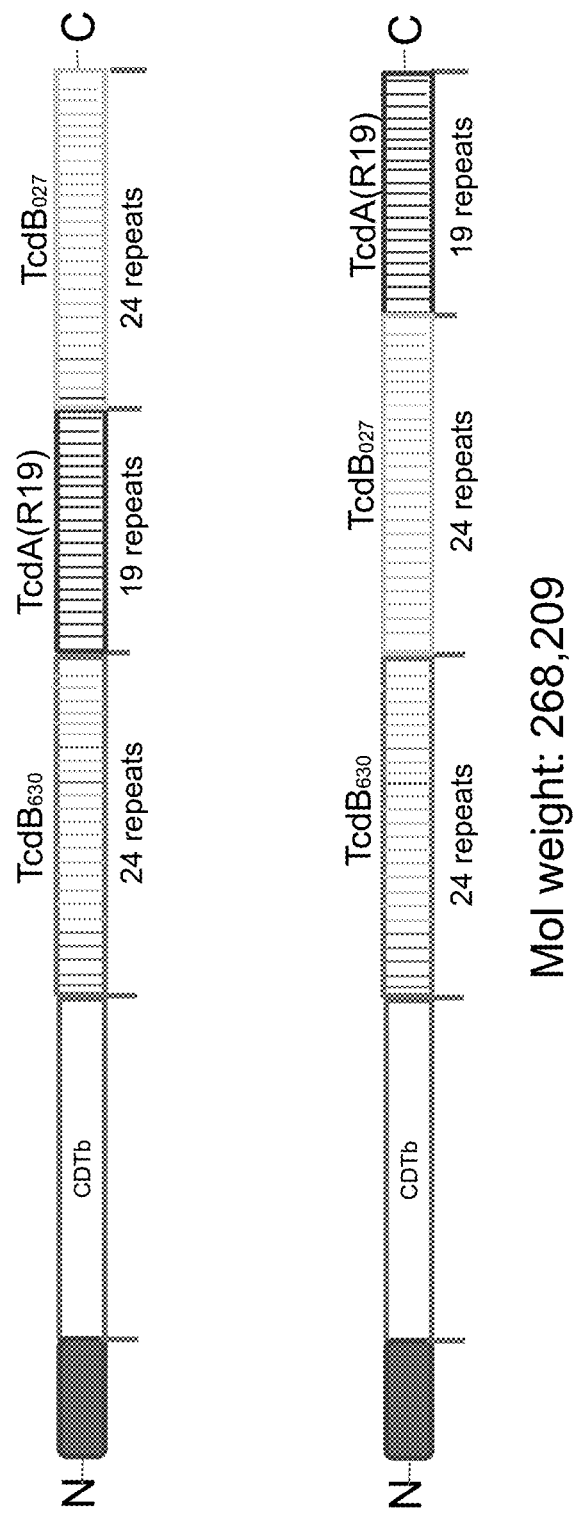
Fig. 20: Quadrivalent toxin vaccine
Mol weight: 268,209

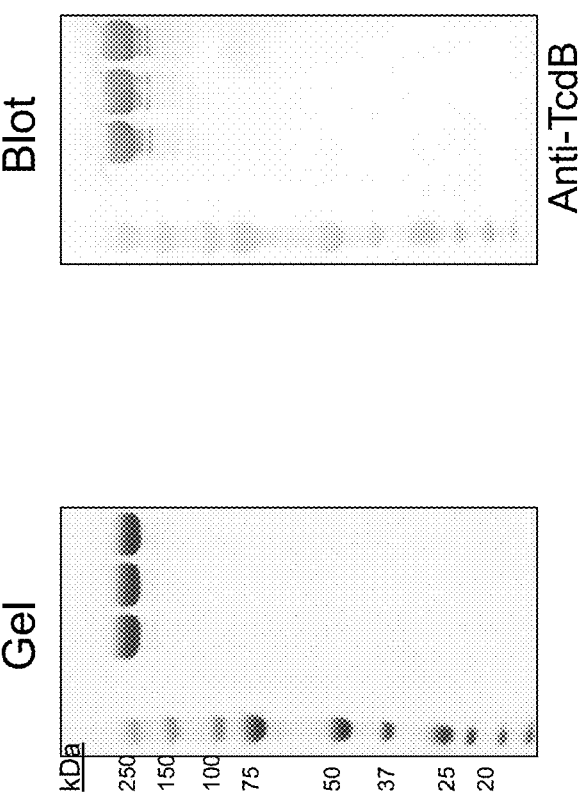
Fig. 21: Purified quadrivalent vaccine - CBAB pCDTb/TcdB630/TcdAR19/TcdB027

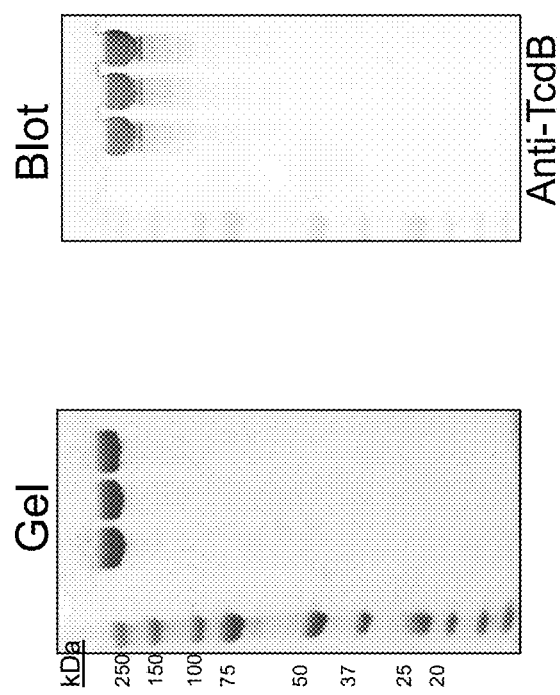
Fig. 22: Purified quadrivalent vaccine – CBBA pCDTb/TcdB630/TcdB027/TcdAR19
yield from culture med Fig. 24. Expression and purification of T-toxin and Q-toxin fusion proteins.

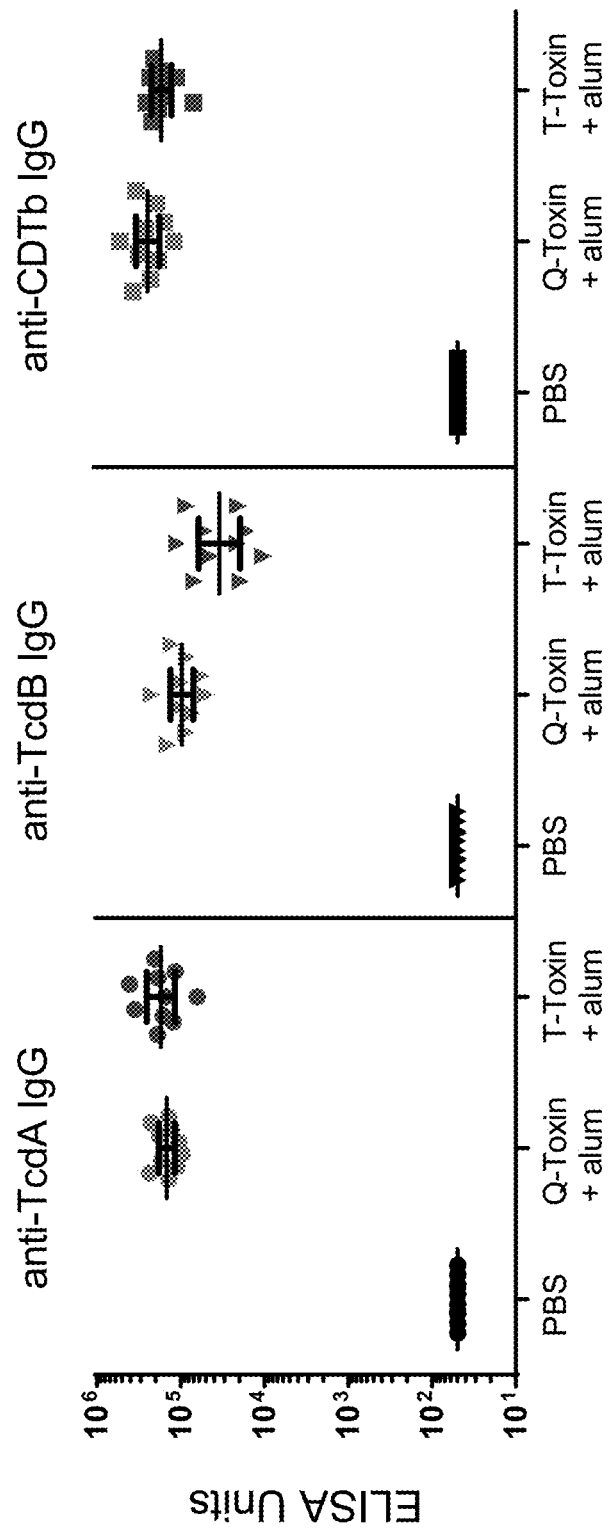
Fig. 25A: Immunogenicity of T-toxin and Q-toxin fusion proteins in mice: Serum IgG titers to TcdA, TcdB(003), and

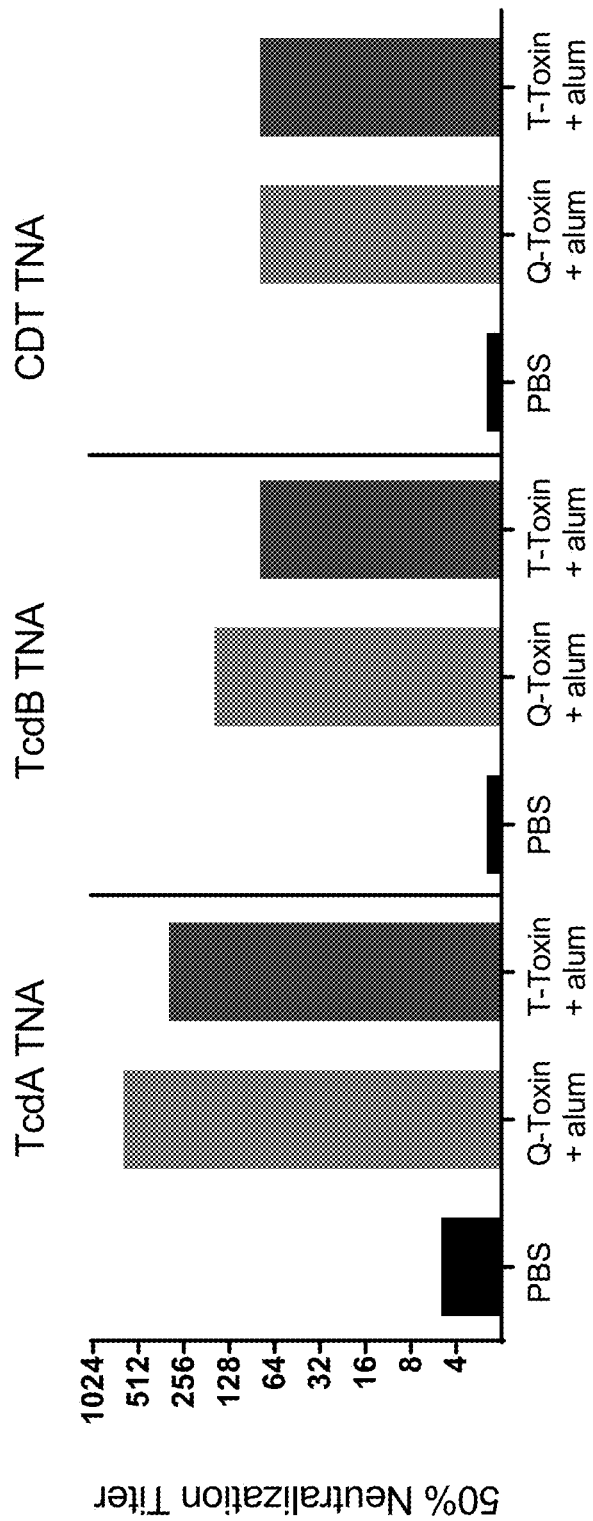
Fig. 25B: Immunogenicity of T-toxin and Q-toxin fusion proteins in mice: toxin-neutralizing antibody (TNA) titers using pooled ser Fig. 25C: Immunogenicity of T-toxin and Q-toxin fusion proteins in mice: Protection against lethal challenge Fig. 26A: Immunogenicity of T-toxin and Q-toxin fusion proteins in hamsters: Serum IgG titers to TcdA, TcdB(003), and CDTb determined by ELISA Fig. 26B: Immunogenicity of T-toxin and Q-toxin fusion proteins in hamsters : Toxin-neutralizing antibody (TNA) titers using pooled serum

SEQUENCE LISTING

```
<160> NUMBER OF SEQ ID NOS: 28

<210> SEQ ID NO 1
<211> LENGTH: 1813
<212> TYPE: PRT
<213> ORGANISM: Artificial Sequence
<220> FEATURE:
<223> OTHER INFORMATION: Triple toxin vaccine BV1470
<220> FEATURE:
<221> NAME/KEY: SITE
<222> LOCATION: (588)..(588)
<223> OTHER INFORMATION: Xaa can be any naturally occurring amino acid

<400> SEQUENCE: 1

Met Glu Ile Val Asn Glu Asp Ile Leu Pro Asn Asn Gly Leu Met Gly
1               5                   10                  15

Tyr Tyr Phe Thr Asp Glu His Phe Lys Asp Leu Lys Leu Met Ala Pro
            20                  25                  30

Ile Lys Asp Gly Asn Leu Lys Phe Glu Glu Lys Lys Val Asp Lys Leu
        35                  40                  45

Leu Asp Lys Asp Lys Ser Asp Val Lys Ser Ile Arg Trp Thr Gly Arg
    50                  55                  60

Ile Ile Pro Ser Lys Asp Gly Glu Tyr Thr Leu Ser Thr Asp Arg Asp
65                  70                  75                  80
```

```
Asp Val Leu Met Gln Val Asn Thr Glu Ser Thr Ile Ser Asn Thr Leu
            85                  90                  95

Lys Val Asn Met Lys Lys Gly Lys Glu Tyr Lys Val Arg Ile Glu Leu
           100                 105                 110

Gln Asp Lys Asn Leu Gly Ser Ile Asp Asn Leu Ser Ser Pro Asn Leu
           115                 120                 125

Tyr Trp Glu Leu Asp Gly Met Lys Lys Ile Ile Pro Glu Glu Asn Leu
130                 135                 140

Phe Leu Arg Asp Tyr Ser Asn Ile Glu Lys Asp Pro Phe Ile Pro
145                 150                 155                 160

Asn Asn Asn Phe Phe Asp Pro Lys Leu Met Ser Asp Trp Glu Asp Glu
                165                 170                 175

Asp Leu Asp Thr Asp Asn Asp Asn Ile Pro Asp Ser Tyr Glu Arg Asn
                180                 185                 190

Gly Tyr Thr Ile Lys Asp Leu Ile Ala Val Lys Trp Glu Asp Ser Phe
            195                 200                 205

Ala Glu Gln Gly Tyr Lys Lys Tyr Val Ser Asn Tyr Leu Glu Ser Asn
            210                 215                 220

Thr Ala Gly Asp Pro Tyr Thr Asp Tyr Glu Lys Ala Ser Gly Ser Phe
225                 230                 235                 240

Asp Lys Ala Ile Lys Thr Glu Ala Arg Asp Pro Leu Val Ala Ala Tyr
                245                 250                 255

Pro Ile Val Gly Val Gly Met Glu Lys Leu Ile Ile Ser Thr Asn Glu
                260                 265                 270

His Ala Ser Thr Asp Gln Gly Lys Thr Val Ser Arg Ala Thr Thr Asn
            275                 280                 285

Ser Lys Thr Glu Ser Asn Thr Ala Gly Val Ser Val Asn Val Gly Tyr
            290                 295                 300

Gln Asn Gly Phe Thr Ala Asn Val Thr Thr Asn Tyr Ser His Thr Thr
305                 310                 315                 320

Asp Asn Ser Thr Ala Val Gln Asp Ser Asn Gly Glu Ser Trp Asn Thr
                325                 330                 335

Gly Leu Ser Ile Asn Lys Gly Glu Ser Ala Tyr Ile Asn Ala Asn Val
            340                 345                 350

Arg Tyr Tyr Asn Thr Gly Thr Ala Pro Met Tyr Lys Val Thr Pro Thr
            355                 360                 365

Thr Asn Leu Val Leu Asp Gly Asp Thr Leu Ser Thr Ile Lys Ala Gln
            370                 375                 380

Glu Asn Gln Ile Gly Asn Asn Leu Ser Pro Gly Asp Thr Tyr Pro Lys
385                 390                 395                 400

Lys Gly Leu Ser Pro Leu Ala Leu Asn Thr Met Asp Gln Phe Ser Ser
                405                 410                 415

Arg Leu Ile Pro Ile Asn Tyr Asp Gln Leu Lys Lys Leu Asp Ala Gly
                420                 425                 430

Lys Gln Ile Lys Leu Glu Thr Thr Gln Val Ser Gly Asn Phe Gly Thr
            435                 440                 445

Lys Asn Ser Ser Gly Gln Ile Val Thr Glu Gly Asn Ser Trp Ser Asp
450                 455                 460

Tyr Ile Ser Gln Ile Asp Ser Ile Ser Ala Ser Ile Ile Leu Asp Thr
465                 470                 475                 480

Glu Asn Glu Ser Tyr Glu Arg Arg Val Thr Ala Lys Asn Leu Gln Asp
                485                 490                 495
```

```
Pro Glu Asp Lys Thr Pro Glu Leu Thr Ile Gly Glu Ala Ile Glu Lys
            500                 505                 510

Ala Phe Gly Ala Thr Lys Lys Asp Gly Leu Leu Tyr Phe Asn Asp Ile
        515                 520                 525

Pro Ile Asp Glu Ser Cys Val Glu Leu Ile Phe Asp Asp Asn Thr Ala
        530                 535                 540

Asn Lys Ile Lys Asp Ser Leu Lys Thr Leu Ser Asp Lys Lys Ile Tyr
545                 550                 555                 560

Asn Val Lys Leu Glu Arg Gly Met Asn Ile Leu Ile Lys Thr Pro Thr
                565                 570                 575

Tyr Phe Thr Asn Phe Asp Asp Tyr Asn Asn Tyr Xaa Ser Thr Trp Ser
            580                 585                 590

Asn Val Asn Thr Thr Asn Gln Asp Gly Leu Gln Gly Ser Ala Asn Lys
            595                 600                 605

Leu Asn Gly Glu Thr Lys Ile Lys Ile Pro Met Ser Glu Leu Lys Pro
        610                 615                 620

Tyr Lys Arg Tyr Val Phe Ser Gly Tyr Ser Lys Asp Pro Leu Thr Ser
625                 630                 635                 640

Asn Ser Ile Ile Val Lys Ile Lys Ala Lys Glu Glu Lys Thr Asp Tyr
                645                 650                 655

Leu Val Pro Glu Gln Gly Tyr Thr Lys Phe Ser Tyr Glu Phe Glu Thr
            660                 665                 670

Thr Glu Lys Asp Ser Ser Asn Ile Glu Ile Thr Leu Ile Gly Ser Gly
        675                 680                 685

Thr Thr Tyr Leu Asp Asn Leu Ser Ile Thr Glu Leu Asn Ser Thr Pro
690                 695                 700

Glu Ile Leu Asp Glu Pro Glu Val Lys Ile Pro Thr Asp Gln Glu Ile
705                 710                 715                 720

Met Asp Ala His Lys Ile Tyr Phe Ala Asp Leu Asn Phe Asn Pro Ser
                725                 730                 735

Thr Gly Asn Thr Tyr Ile Asn Gly Met Tyr Phe Ala Pro Thr Gln Thr
            740                 745                 750

Asn Lys Glu Ala Leu Asp Tyr Ile Gln Lys Tyr Arg Val Glu Ala Thr
        755                 760                 765

Leu Gln Tyr Ser Gly Phe Lys Asp Ile Gly Thr Lys Asp Lys Glu Met
    770                 775                 780

Arg Asn Tyr Leu Gly Asp Pro Asn Gln Pro Lys Thr Asn Tyr Val Asn
785                 790                 795                 800

Leu Arg Ser Tyr Phe Thr Gly Gly Glu Asn Ile Met Thr Tyr Lys Lys
                805                 810                 815

Leu Arg Ile Tyr Ala Ile Thr Pro Asp Asp Arg Glu Leu Leu Val Leu
            820                 825                 830

Ser Val Asp Ala Ser Met Val Ser Gly Leu Ile Tyr Ile Asn Asp Ser
        835                 840                 845

Leu Tyr Tyr Phe Lys Pro Pro Val Asn Asn Leu Ile Thr Gly Phe Val
    850                 855                 860

Thr Val Gly Asp Asp Lys Tyr Tyr Phe Asn Pro Ile Asn Gly Gly Ala
865                 870                 875                 880

Ala Ser Ile Gly Glu Thr Ile Ile Asp Asp Lys Asn Tyr Tyr Phe Asn
                885                 890                 895

Gln Ser Gly Val Leu Gln Thr Gly Val Phe Ser Thr Glu Asp Gly Phe
            900                 905                 910

Lys Tyr Phe Ala Pro Ala Asn Thr Leu Asp Glu Asn Leu Glu Gly Glu
```

-continued

```
                915                 920                 925
Ala Ile Asp Phe Thr Gly Lys Leu Ile Ile Asp Glu Asn Ile Tyr Tyr
    930                 935                 940

Phe Asp Asp Asn Tyr Arg Gly Ala Val Glu Trp Lys Glu Leu Asp Gly
945                 950                 955                 960

Glu Met His Tyr Phe Ser Pro Glu Thr Gly Lys Ala Phe Lys Gly Leu
                965                 970                 975

Asn Gln Ile Gly Asp Tyr Lys Tyr Tyr Phe Asn Ser Asp Gly Val Met
                980                 985                 990

Gln Lys Gly Phe Val Ser Ile Asn Asp Asn Lys His Tyr Phe Asp Asp
                995                 1000                1005

Ser Gly Val Met Lys Val Gly Tyr Thr Glu Ile Asp Gly Lys His
    1010                1015                1020

Phe Tyr Phe Ala Glu Asn Gly Glu Met Gln Ile Gly Val Phe Asn
    1025                1030                1035

Thr Glu Asp Gly Phe Lys Tyr Phe Ala His His Asn Glu Asp Leu
    1040                1045                1050

Gly Asn Glu Glu Gly Glu Glu Ile Ser Tyr Ser Gly Ile Leu Asn
    1055                1060                1065

Phe Asn Asn Lys Ile Tyr Tyr Phe Asp Asp Ser Phe Thr Ala Val
    1070                1075                1080

Val Gly Trp Lys Asp Leu Glu Asp Gly Ser Lys Tyr Tyr Phe Asp
    1085                1090                1095

Glu Asp Thr Ala Glu Ala Tyr Ile Gly Leu Ser Leu Ile Asn Asp
    1100                1105                1110

Gly Gln Tyr Tyr Phe Asn Asp Asp Gly Ile Met Gln Val Gly Phe
    1115                1120                1125

Val Thr Ile Asn Asp Lys Val Phe Tyr Phe Ser Asp Ser Gly Ile
    1130                1135                1140

Ile Glu Ser Gly Val Gln Asn Ile Asp Asp Asn Tyr Phe Tyr Ile
    1145                1150                1155

Asp Asp Asn Gly Ile Val Gln Ile Gly Val Phe Asp Thr Ser Asp
    1160                1165                1170

Gly Tyr Lys Tyr Phe Ala Pro Ala Asn Thr Val Asn Asp Asn Ile
    1175                1180                1185

Tyr Gly Gln Ala Val Glu Tyr Ser Gly Leu Val Arg Val Gly Glu
    1190                1195                1200

Asp Val Tyr Tyr Phe Gly Glu Thr Tyr Thr Ile Glu Thr Gly Trp
    1205                1210                1215

Ile Tyr Asp Met Glu Asn Glu Ser Asp Lys Tyr Tyr Phe Asn Pro
    1220                1225                1230

Glu Thr Lys Lys Ala Cys Lys Gly Ile Asn Leu Ile Asp Asp Ile
    1235                1240                1245

Lys Tyr Tyr Phe Asp Glu Lys Gly Ile Met Arg Thr Gly Leu Ile
    1250                1255                1260

Ser Phe Glu Asn Asn Asn Tyr Tyr Phe Asn Glu Asn Gly Glu Met
    1265                1270                1275

Gln Phe Gly Tyr Ile Asn Ile Glu Asp Lys Met Phe Tyr Phe Gly
    1280                1285                1290

Glu Asp Gly Val Met Gln Ile Gly Val Phe Asn Thr Pro Asp Gly
    1295                1300                1305

Phe Lys Tyr Phe Ala His Gln Asn Thr Leu Asp Glu Asn Phe Glu
    1310                1315                1320
```

```
Gly Glu Ser Ile Asn Tyr Thr Gly Trp Leu Asp Leu Asp Glu Lys
1325                1330                1335

Arg Tyr Tyr Phe Thr Asp Glu Tyr Ile Ala Ala Thr Gly Ser Val
1340                1345                1350

Ile Ile Asp Gly Glu Tyr Tyr Phe Asp Pro Asp Thr Ala Gln
1355                1360                1365

Leu Val Ile Ser Glu Ser Arg Met Val Thr Gly Val Phe Lys Gly
1370                1375                1380

Pro Asn Gly Phe Glu Tyr Phe Ala Pro Ala Asn Thr His Asn Asn
1385                1390                1395

Asn Ile Glu Gly Gln Ala Ile Val Tyr Gln Asn Lys Phe Leu Thr
1400                1405                1410

Leu Asn Gly Lys Lys Tyr Tyr Phe Asp Asn Asp Ser Lys Ala Val
1415                1420                1425

Thr Gly Trp Gln Thr Ile Asp Gly Lys Lys Tyr Tyr Phe Asn Leu
1430                1435                1440

Asn Thr Ala Glu Ala Ala Thr Gly Trp Gln Thr Ile Asp Gly Lys
1445                1450                1455

Lys Tyr Tyr Phe Asn Leu Asn Thr Ala Glu Ala Ala Thr Gly Trp
1460                1465                1470

Gln Thr Ile Asp Gly Lys Lys Tyr Tyr Phe Asn Thr Asn Thr Phe
1475                1480                1485

Ile Ala Ser Thr Gly Tyr Thr Ser Ile Asn Gly Lys His Phe Tyr
1490                1495                1500

Phe Asn Thr Asp Gly Ile Met Gln Ile Gly Val Phe Lys Gly Pro
1505                1510                1515

Asn Gly Phe Glu Tyr Phe Ala Pro Ala Asn Thr Asp Ala Asn Asn
1520                1525                1530

Ile Glu Gly Gln Ala Ile Leu Tyr Gln Asn Lys Phe Leu Thr Leu
1535                1540                1545

Asn Gly Lys Lys Tyr Tyr Phe Gly Ser Asp Ser Lys Ala Val Thr
1550                1555                1560

Gly Leu Arg Thr Ile Asp Gly Lys Lys Tyr Tyr Phe Asn Thr Asn
1565                1570                1575

Thr Ala Val Ala Val Thr Gly Trp Gln Thr Ile Asn Gly Lys Lys
1580                1585                1590

Tyr Tyr Phe Asn Thr Asn Thr Ser Ile Ala Ser Thr Gly Tyr Thr
1595                1600                1605

Ile Ile Ser Gly Lys His Phe Tyr Phe Asn Thr Asp Gly Ile Met
1610                1615                1620

Gln Ile Gly Val Phe Lys Gly Pro Asp Gly Phe Glu Tyr Phe Ala
1625                1630                1635

Pro Ala Asn Thr Asp Ala Asn Asn Ile Glu Gly Gln Ala Ile Arg
1640                1645                1650

Tyr Gln Asn Arg Phe Leu Tyr Leu His Asp Asn Ile Tyr Tyr Phe
1655                1660                1665

Gly Asn Asn Ser Lys Ala Ala Thr Gly Trp Val Thr Ile Asp Gly
1670                1675                1680

Asn Arg Tyr Tyr Phe Glu Pro Asn Thr Ala Met Gly Ala Asn Gly
1685                1690                1695

Tyr Lys Thr Ile Asp Asn Lys Asn Phe Tyr Phe Arg Asn Gly Leu
1700                1705                1710
```

```
Pro Gln  Ile Gly Val Phe Lys  Gly Ser Asn Gly Phe  Glu Tyr Phe
    1715                 1720                 1725

Ala Pro  Ala Asn Thr Asp Ala  Asn Asn Ile Glu Gly  Gln Ala Ile
    1730                 1735                 1740

Arg Tyr  Gln Asn Arg Phe Leu  His Leu Leu Gly Lys  Ile Tyr Tyr
    1745                 1750                 1755

Phe Gly  Asn Asn Ser Lys Ala  Val Thr Gly Trp Gln  Thr Ile Asn
    1760                 1765                 1770

Gly Lys  Val Tyr Tyr Phe Met  Pro Asp Thr Ala Met  Ala Ala Ala
    1775                 1780                 1785

Gly Gly  Leu Phe Glu Ile Asp  Gly Val Ile Tyr Phe  Phe Gly Val
    1790                 1795                 1800

Asp Gly  Val Lys Ala Pro Gly  Ile Tyr Gly
    1805                 1810

<210> SEQ ID NO 2
<211> LENGTH: 835
<212> TYPE: PRT
<213> ORGANISM: Clostridium difficile
<220> FEATURE:
<221> NAME/KEY: SITE
<222> LOCATION: (588)..(588)
<223> OTHER INFORMATION: Xaa can be any naturally occurring amino acid

<400> SEQUENCE: 2

Met Glu Ile Val Asn Glu Asp Ile Leu Pro Asn Asn Gly Leu Met Gly
1               5                   10                  15

Tyr Tyr Phe Thr Asp Glu His Phe Lys Asp Leu Lys Leu Met Ala Pro
            20                  25                  30

Ile Lys Asp Gly Asn Leu Lys Phe Glu Glu Lys Lys Val Asp Lys Leu
        35                  40                  45

Leu Asp Lys Asp Lys Ser Asp Val Lys Ser Ile Arg Trp Thr Gly Arg
    50                  55                  60

Ile Ile Pro Ser Lys Asp Gly Glu Tyr Thr Leu Ser Thr Asp Arg Asp
65                  70                  75                  80

Asp Val Leu Met Gln Val Asn Thr Glu Ser Thr Ile Ser Asn Thr Leu
                85                  90                  95

Lys Val Asn Met Lys Lys Gly Lys Glu Tyr Lys Val Arg Ile Glu Leu
            100                 105                 110

Gln Asp Lys Asn Leu Gly Ser Ile Asp Asn Leu Ser Ser Pro Asn Leu
        115                 120                 125

Tyr Trp Glu Leu Asp Gly Met Lys Lys Ile Ile Pro Glu Glu Asn Leu
    130                 135                 140

Phe Leu Arg Asp Tyr Ser Asn Ile Glu Lys Asp Asp Pro Phe Ile Pro
145                 150                 155                 160

Asn Asn Asn Phe Phe Asp Pro Lys Leu Met Ser Asp Trp Glu Asp Glu
                165                 170                 175

Asp Leu Asp Thr Asp Asn Asp Asn Ile Pro Asp Ser Tyr Glu Arg Asn
            180                 185                 190

Gly Tyr Thr Ile Lys Asp Leu Ile Ala Val Lys Trp Glu Asp Ser Phe
        195                 200                 205

Ala Glu Gln Gly Tyr Lys Lys Tyr Val Ser Asn Tyr Leu Glu Ser Asn
    210                 215                 220

Thr Ala Gly Asp Pro Tyr Thr Asp Tyr Glu Lys Ala Ser Gly Ser Phe
225                 230                 235                 240

Asp Lys Ala Ile Lys Thr Glu Ala Arg Asp Pro Leu Val Ala Ala Tyr
```

-continued

```
                245                 250                 255
Pro Ile Val Gly Val Gly Met Glu Lys Leu Ile Ile Ser Thr Asn Glu
            260                 265                 270

His Ala Ser Thr Asp Gln Gly Lys Thr Val Ser Arg Ala Thr Thr Asn
        275                 280                 285

Ser Lys Thr Glu Ser Asn Thr Ala Gly Val Ser Val Asn Val Gly Tyr
    290                 295                 300

Gln Asn Gly Phe Thr Ala Asn Val Thr Thr Asn Tyr Ser His Thr Thr
305                 310                 315                 320

Asp Asn Ser Thr Ala Val Gln Asp Ser Asn Gly Glu Ser Trp Asn Thr
                325                 330                 335

Gly Leu Ser Ile Asn Lys Gly Glu Ser Ala Tyr Ile Asn Ala Asn Val
            340                 345                 350

Arg Tyr Tyr Asn Thr Gly Thr Ala Pro Met Tyr Lys Val Thr Pro Thr
        355                 360                 365

Thr Asn Leu Val Leu Asp Gly Asp Thr Leu Ser Thr Ile Lys Ala Gln
    370                 375                 380

Glu Asn Gln Ile Gly Asn Asn Leu Ser Pro Gly Asp Thr Tyr Pro Lys
385                 390                 395                 400

Lys Gly Leu Ser Pro Leu Ala Leu Asn Thr Met Asp Gln Phe Ser Ser
                405                 410                 415

Arg Leu Ile Pro Ile Asn Tyr Asp Gln Leu Lys Lys Leu Asp Ala Gly
            420                 425                 430

Lys Gln Ile Lys Leu Glu Thr Thr Gln Val Ser Gly Asn Phe Gly Thr
        435                 440                 445

Lys Asn Ser Ser Gly Gln Ile Val Thr Glu Gly Asn Ser Trp Ser Asp
    450                 455                 460

Tyr Ile Ser Gln Ile Asp Ser Ile Ser Ala Ser Ile Ile Leu Asp Thr
465                 470                 475                 480

Glu Asn Glu Ser Tyr Glu Arg Arg Val Thr Ala Lys Asn Leu Gln Asp
                485                 490                 495

Pro Glu Asp Lys Thr Pro Glu Leu Thr Ile Gly Glu Ala Ile Glu Lys
            500                 505                 510

Ala Phe Gly Ala Thr Lys Lys Asp Gly Leu Leu Tyr Phe Asn Asp Ile
        515                 520                 525

Pro Ile Asp Glu Ser Cys Val Glu Leu Ile Phe Asp Asp Asn Thr Ala
    530                 535                 540

Asn Lys Ile Lys Asp Ser Leu Lys Thr Leu Ser Asp Lys Lys Ile Tyr
545                 550                 555                 560

Asn Val Lys Leu Glu Arg Gly Met Asn Ile Leu Ile Lys Thr Pro Thr
                565                 570                 575

Tyr Phe Thr Asn Phe Asp Asp Tyr Asn Asn Tyr Xaa Ser Thr Trp Ser
            580                 585                 590

Asn Val Asn Thr Thr Asn Gln Asp Gly Leu Gln Gly Ser Ala Asn Lys
        595                 600                 605

Leu Asn Gly Glu Thr Lys Ile Lys Ile Pro Met Ser Glu Leu Lys Pro
    610                 615                 620

Tyr Lys Arg Tyr Val Phe Ser Gly Tyr Ser Lys Asp Pro Leu Thr Ser
625                 630                 635                 640

Asn Ser Ile Ile Val Lys Ile Lys Ala Lys Glu Glu Lys Thr Asp Tyr
                645                 650                 655

Leu Val Pro Glu Gln Gly Tyr Thr Lys Phe Ser Tyr Glu Phe Glu Thr
            660                 665                 670
```

-continued

```
Thr Glu Lys Asp Ser Ser Asn Ile Glu Ile Thr Leu Ile Gly Ser Gly
        675                 680                 685

Thr Thr Tyr Leu Asp Asn Leu Ser Ile Thr Glu Leu Asn Ser Thr Pro
    690                 695                 700

Glu Ile Leu Asp Glu Pro Glu Val Lys Ile Pro Thr Asp Gln Glu Ile
705                 710                 715                 720

Met Asp Ala His Lys Ile Tyr Phe Ala Asp Leu Asn Phe Asn Pro Ser
                725                 730                 735

Thr Gly Asn Thr Tyr Ile Asn Gly Met Tyr Phe Ala Pro Thr Gln Thr
            740                 745                 750

Asn Lys Glu Ala Leu Asp Tyr Ile Gln Lys Tyr Arg Val Glu Ala Thr
        755                 760                 765

Leu Gln Tyr Ser Gly Phe Lys Asp Ile Gly Thr Lys Asp Lys Glu Met
    770                 775                 780

Arg Asn Tyr Leu Gly Asp Pro Asn Gln Pro Lys Thr Asn Tyr Val Asn
785                 790                 795                 800

Leu Arg Ser Tyr Phe Thr Gly Gly Glu Asn Ile Met Thr Tyr Lys Lys
                805                 810                 815

Leu Arg Ile Tyr Ala Ile Thr Pro Asp Asp Arg Glu Leu Leu Val Leu
            820                 825                 830

Ser Val Asp
        835

<210> SEQ ID NO 3
<211> LENGTH: 536
<212> TYPE: PRT
<213> ORGANISM: Clostridium difficile

<400> SEQUENCE: 3

Met Val Ser Gly Leu Ile Tyr Ile Asn Asp Ser Leu Tyr Tyr Phe Lys
1               5                   10                  15

Pro Pro Val Asn Asn Leu Ile Thr Gly Phe Val Thr Val Gly Asp Asp
            20                  25                  30

Lys Tyr Tyr Phe Asn Pro Ile Asn Gly Gly Ala Ala Ser Ile Gly Glu
        35                  40                  45

Thr Ile Ile Asp Asp Lys Asn Tyr Tyr Phe Asn Gln Ser Gly Val Leu
    50                  55                  60

Gln Thr Gly Val Phe Ser Thr Glu Asp Gly Phe Lys Tyr Phe Ala Pro
65                  70                  75                  80

Ala Asn Thr Leu Asp Glu Asn Leu Glu Gly Glu Ala Ile Asp Phe Thr
                85                  90                  95

Gly Lys Leu Ile Ile Asp Glu Asn Ile Tyr Tyr Phe Asp Asp Asn Tyr
            100                 105                 110

Arg Gly Ala Val Glu Trp Lys Glu Leu Asp Gly Glu Met His Tyr Phe
        115                 120                 125

Ser Pro Glu Thr Gly Lys Ala Phe Lys Gly Leu Asn Gln Ile Gly Asp
    130                 135                 140

Tyr Lys Tyr Tyr Phe Asn Ser Asp Gly Val Met Gln Lys Gly Phe Val
145                 150                 155                 160

Ser Ile Asn Asp Asn Lys His Tyr Phe Asp Asp Ser Gly Val Met Lys
                165                 170                 175

Val Gly Tyr Thr Glu Ile Asp Gly Lys His Phe Tyr Phe Ala Glu Asn
            180                 185                 190

Gly Glu Met Gln Ile Gly Val Phe Asn Thr Glu Asp Gly Phe Lys Tyr
```

```
                195                 200                 205
Phe Ala His His Asn Glu Asp Leu Gly Asn Glu Glu Gly Glu Glu Ile
210                 215                 220
Ser Tyr Ser Gly Ile Leu Asn Phe Asn Asn Lys Ile Tyr Tyr Phe Asp
225                 230                 235                 240
Asp Ser Phe Thr Ala Val Val Gly Trp Lys Asp Leu Glu Asp Gly Ser
                245                 250                 255
Lys Tyr Tyr Phe Asp Glu Asp Thr Ala Glu Ala Tyr Ile Gly Leu Ser
                260                 265                 270
Leu Ile Asn Asp Gly Gln Tyr Tyr Phe Asn Asp Asp Gly Ile Met Gln
                275                 280                 285
Val Gly Phe Val Thr Ile Asn Asp Lys Val Phe Tyr Phe Ser Asp Ser
290                 295                 300
Gly Ile Ile Glu Ser Gly Val Gln Asn Ile Asp Asp Asn Tyr Phe Tyr
305                 310                 315                 320
Ile Asp Asp Asn Gly Ile Val Gln Ile Gly Val Phe Asp Thr Ser Asp
                325                 330                 335
Gly Tyr Lys Tyr Phe Ala Pro Ala Asn Thr Val Asn Asp Asn Ile Tyr
                340                 345                 350
Gly Gln Ala Val Glu Tyr Ser Gly Leu Val Arg Val Gly Glu Asp Val
                355                 360                 365
Tyr Tyr Phe Gly Glu Thr Tyr Thr Ile Glu Thr Gly Trp Ile Tyr Asp
                370                 375                 380
Met Glu Asn Glu Ser Asp Lys Tyr Tyr Phe Asn Pro Glu Thr Lys Lys
385                 390                 395                 400
Ala Cys Lys Gly Ile Asn Leu Ile Asp Asp Ile Lys Tyr Tyr Phe Asp
                405                 410                 415
Glu Lys Gly Ile Met Arg Thr Gly Leu Ile Ser Phe Glu Asn Asn Asn
                420                 425                 430
Tyr Tyr Phe Asn Glu Asn Gly Glu Met Gln Phe Gly Tyr Ile Asn Ile
                435                 440                 445
Glu Asp Lys Met Phe Tyr Phe Gly Glu Asp Gly Val Met Gln Ile Gly
450                 455                 460
Val Phe Asn Thr Pro Asp Gly Phe Lys Tyr Phe Ala His Gln Asn Thr
465                 470                 475                 480
Leu Asp Glu Asn Phe Glu Gly Glu Ser Ile Asn Tyr Thr Gly Trp Leu
                485                 490                 495
Asp Leu Asp Glu Lys Arg Tyr Tyr Phe Thr Asp Glu Tyr Ile Ala Ala
                500                 505                 510
Thr Gly Ser Val Ile Ile Asp Gly Glu Glu Tyr Tyr Phe Asp Pro Asp
                515                 520                 525
Thr Ala Gln Leu Val Ile Ser Glu
                530                 535

<210> SEQ ID NO 4
<211> LENGTH: 438
<212> TYPE: PRT
<213> ORGANISM: Clostridium difficile

<400> SEQUENCE: 4

Met Val Thr Gly Val Phe Lys Gly Pro Asn Gly Phe Glu Tyr Phe Ala
1               5                   10                  15
Pro Ala Asn Thr His Asn Asn Asn Ile Glu Gly Gln Ala Ile Val Tyr
                20                  25                  30
```

-continued

```
Gln Asn Lys Phe Leu Thr Leu Asn Gly Lys Lys Tyr Tyr Phe Asp Asn
             35                  40                  45
Asp Ser Lys Ala Val Thr Gly Trp Gln Thr Ile Asp Gly Lys Lys Tyr
 50                  55                  60
Tyr Phe Asn Leu Asn Thr Ala Glu Ala Ala Thr Gly Trp Gln Thr Ile
 65                  70                  75                  80
Asp Gly Lys Lys Tyr Tyr Phe Asn Leu Asn Thr Ala Glu Ala Ala Thr
                 85                  90                  95
Gly Trp Gln Thr Ile Asp Gly Lys Lys Tyr Tyr Phe Asn Thr Asn Thr
            100                 105                 110
Phe Ile Ala Ser Thr Gly Tyr Thr Ser Ile Asn Gly Lys His Phe Tyr
            115                 120                 125
Phe Asn Thr Asp Gly Ile Met Gln Ile Gly Val Phe Lys Gly Pro Asn
            130                 135                 140
Gly Phe Glu Tyr Phe Ala Pro Ala Asn Thr Asp Ala Asn Asn Ile Glu
145                 150                 155                 160
Gly Gln Ala Ile Leu Tyr Gln Asn Lys Phe Leu Thr Leu Asn Gly Lys
                165                 170                 175
Lys Tyr Tyr Phe Gly Ser Asp Ser Lys Ala Val Thr Gly Leu Arg Thr
            180                 185                 190
Ile Asp Gly Lys Lys Tyr Tyr Phe Asn Thr Asn Thr Ala Val Ala Val
            195                 200                 205
Thr Gly Trp Gln Thr Ile Asn Gly Lys Lys Tyr Tyr Phe Asn Thr Asn
            210                 215                 220
Thr Ser Ile Ala Ser Thr Gly Tyr Thr Ile Ile Ser Gly Lys His Phe
225                 230                 235                 240
Tyr Phe Asn Thr Asp Gly Ile Met Gln Ile Gly Val Phe Lys Gly Pro
            245                 250                 255
Asp Gly Phe Glu Tyr Phe Ala Pro Ala Asn Thr Asp Ala Asn Asn Ile
            260                 265                 270
Glu Gly Gln Ala Ile Arg Tyr Gln Asn Arg Phe Leu Tyr Leu His Asp
            275                 280                 285
Asn Ile Tyr Tyr Phe Gly Asn Asn Ser Lys Ala Ala Thr Gly Trp Val
290                 295                 300
Thr Ile Asp Gly Asn Arg Tyr Tyr Phe Glu Pro Asn Thr Ala Met Gly
305                 310                 315                 320
Ala Asn Gly Tyr Lys Thr Ile Asp Asn Lys Asn Phe Tyr Phe Arg Asn
                325                 330                 335
Gly Leu Pro Gln Ile Gly Val Phe Lys Gly Ser Asn Gly Phe Glu Tyr
            340                 345                 350
Phe Ala Pro Ala Asn Thr Asp Ala Asn Asn Ile Glu Gly Gln Ala Ile
            355                 360                 365
Arg Tyr Gln Asn Arg Phe Leu His Leu Leu Gly Lys Ile Tyr Tyr Phe
            370                 375                 380
Gly Asn Asn Ser Lys Ala Val Thr Gly Trp Gln Thr Ile Asn Gly Lys
385                 390                 395                 400
Val Tyr Tyr Phe Met Pro Asp Thr Ala Met Ala Ala Ala Gly Gly Leu
                405                 410                 415
Phe Glu Ile Asp Gly Val Ile Tyr Phe Phe Gly Val Asp Gly Val Lys
            420                 425                 430
Ala Pro Gly Ile Tyr Gly
            435
```

-continued

<210> SEQ ID NO 5
<211> LENGTH: 5442
<212> TYPE: DNA
<213> ORGANISM: Artificial Sequence
<220> FEATURE:
<223> OTHER INFORMATION: Triple toxin vaccine BV1470
<220> FEATURE:
<221> NAME/KEY: SITE
<222> LOCATION: (1763)..(1763)
<223> OTHER INFORMATION: n is a, c, g, or t

<400> SEQUENCE: 5

```
atggaaatcg tcaacgaaga catcctgccg aacaacggtt tgatgggcta ctacttcacc     60
gatgagcact tcaaggacct gaagctcatg gctcctatca aggacggaaa cctgaagttc    120
gaggaaaaga aggtcgataa gctgctcgac aaggataaga gcgacgttaa gtcaatcagg    180
tggaccggca gaatcatccc atccaaggat ggagagtaca ctctctctac agaccgtgac    240
gatgtcttga tgcaggtgaa caccgaatcg actatctcca acactctgaa ggtgaacatg    300
aagaagggaa aggagtacaa ggtgcgcatc gaactgcaag ataagaacct cggttctatc    360
gacaacctct cctctccaaa cctctactgg gagttggatg gcatgaagaa gatcatcccg    420
gaggaaaact tgttcctgcg tgactacagc aacatcgaaa aggacgatcc cttcatccct    480
aacaacaact tcttcgatcc caagctgatg tctgactggg aggacgaaga tctcgacacc    540
gataacgaca acatccctga cagctacgag cgcaacggat acactatcaa ggatctcatc    600
gctgtgaagt gggaggactc cttcgccgaa cagggttaca agaagtacgt ctcaaactac    660
ttggagtcga acacagctgg tgacccctac accgactacg aaaaggcctc cggctctttc    720
gataaggcta tcaagaccga ggctagggac ccactcgtcg ctgcttaccc catcgtggga    780
gtcggtatgg agaagttgat catcagcact aacgaacacg cttcaactga ccagggcaag    840
acagtttcaa gagccaccac taactcgaag accgagtcca acactgctgg cgtttccgtg    900
aacgtcggct accagaacgg attcaccgcc aacgttacaa ccaactactc gcacactaca    960
gataactcca ccgctgtgca agactctaac ggagagagct ggaacactgg tctgtctatc   1020
aacaagggcg aaagcgctta catcaacgcc aacgtccgct actacaacac tggcacagcc   1080
cccatgtaca aggtgacccc taccactaac ctcgtcttgg atggagacac actgtctacc   1140
atcaaggctc aggagaacca aatcggaaac aacctcagcc ccggtgacac ataccctaag   1200
aagggattgt caccactggc cctcaacact atggaccagt tcagctcaag gttgatcccg   1260
atcaactacg atcaactcaa gaagttggac gctggcaagc agatcaagct ggagacaacc   1320
caagtctccg gtaacttcgg caccaagaac tcgtccggcc agatcgttac tgaaggaaac   1380
agctggtcag attacatctc acaaatcgac tcgatctccg cctctatcat cctggacaca   1440
gagaacgaat cctacgagcg tcgcgtgacc gctaagaact tgcaggaccc cgaggacaag   1500
acaccggaac tgaccatcgg cgaggccatc gaaaaggctt tcggtgccac caagaaggac   1560
ggcttgctgt acttcaacga tatccctatc gacgagtcct gcgttgaact gatcttcgac   1620
gataacactg ctaacaagat caaggattcc ctgaagacac tctctgacaa gaagatctac   1680
aacgtgaagc tcgagagggg tatgaacatc ttgatcaaga cccccactta cttcacaaac   1740
ttcgacgatt acaacaacta ccnttctacc tggagcaacg tcaacactac aaaccaggac   1800
ggactgcaag gttcggccaa caagctcaac ggcgagacca agatcaagat cccaatgagc   1860
gaactgaagc cgtacaagag atacgtgttc tcaggctact cgaaggaccc actcactagc   1920
aactcaatca tcgtgaagat caaggctaag gaggaaaaga ccgactacct ggtccccgag   1980
```

```
cagggctaca ctaagttctc ttacgagttc gaaaccactg agaaggactc tagcaacatc    2040
gaaatcaccc tcatcggcag cggaacaacc tacttggaca acctgtcaat caccgagttg    2100
aactcgactc ccgaaatcct ggacgagccc gaagtcaaga tccctaccga tcaggagatc    2160
atggacgctc acaagatcta cttcgccgac ctgaacttca acccctctac tggaaacaca    2220
tacatcaacg gcatgtactt cgctcctaca caaaccaaca aggaggccct ggactacatc    2280
cagaagtacc gtgtcgaagc cactctccaa tactccggtt tcaaggatat cggcacaaag    2340
gacaaggaga tgaggaacta cttgggtgac ccaaaccagc cgaagaccaa ctacgtgaac    2400
ctgagatcat acttcactgg tggcgagaac atcatgacat acaagaagct gcgtatctac    2460
gctatcaccc ctgacgaccg tgaactcttg gttttgtccg tggacgctag catggtcagc    2520
ggtctcatct acatcaacga ctcgttgtac tacttcaagc ccctgtgaa caacctgatc     2580 acaggtttcg ttaccgtggg cgacgataag tactacttca acccaatcaa cggtggcgct    2640
gcctccatcg gcgagaccat catcgacgat aagaactact acttcaacca gagcggagtt    2700
ctccaaactg gtgtgttctc aacagaggac ggtttcaagt acttcgctcc ggccaacacc    2760
ttggacgaaa acctggaggg tgaagccatc gacttcactg gcaagttgat catcgatgag    2820
aacatctact acttcgacga taactaccgc ggtgctgtgg agtggaagga actcgacggc    2880
gagatgcact acttctctcc agaaaccggc aaggccttca agggattgaa ccagatcggt    2940
gactacaagt actacttcaa ctcggatggc gtgatgcaaa agggattcgt ctccatcaac    3000
gacaacaagc actacttcga cgattccggt gttatgaaag tgggctacac agagatcgac    3060
ggcaagcact tctacttcgc tgagaacgga gaaatgcaga tcggtgtctt caacactgaa    3120
gatggtttca gtacttcgc ccaccacaac gaagatttgg gcaacgagga aggagaggaa     3180
atcagctact caggcatcct gaacttcaac aacaagatct actacttcga tgactctttc    3240
accgctgtgg tcggatggaa ggacctggag gatggtagca agtactactt cgacgaggat    3300
actgctgaag cctacatcgg cctgtcgctc atcaacgacg acagtacta cttcaacgac     3360 gatggcatca tgcaagtcgg attcgttacc atcaacgaca aggtgttcta cttctcggat    3420
tccggtatca tcgagtctgg cgtccagaac atcgacgata actacttcta catcgacgat    3480
aacggaatcg tgcaaatcgg tgtcttcgac acaagcgatg gctacaagta cttcgctccc    3540
gccaacaccg tgaacgacaa catctacgga caggctgtgg agtactcagg cctggtccgt    3600
gttggagaag acgtgtacta cttcggcgag acctacacta tcgaaactgg atggatctac    3660
gacatggaga cgaatctga caagtactac ttcaaccctg agacaaagaa ggcctgcaag     3720
ggtatcaacc tgatcgacga tatcaagtac tacttcgatg aaaagggtat catgcgcacc    3780
ggcctcatct cattcgaaaa caacaactac tacttcaacg agaacggaga atgcaattc     3840 ggttacatca acatcgagga caagatgttc tacttcggag aagatggtgt catgcagatc    3900
ggtgttttca acactccaga cggcttcaag tacttcgctc accaaaacac actcgacgag    3960
aacttcgagg gagaatccat caactacact ggttggttgg acctggatga aagaggtac    4020 tacttcaccg acgaatacat cgctgccact ggctccgtca tcatcgacgg agaggaatac    4080
tacttcgacc cggatacagc ccagctggtc atctctgaat ctagaatggt gaccggtgtc    4140
ttcaagggtc ccaacggctt cgagtacttc gctcccgcca acactcacaa caacaacatc    4200
gaaggtcaag ctatcgtcta ccaaaacaag ttcttgaccc tgaacggcaa gaagtattat    4260
tttgacaacg attctaaggc cgttactggc tggcaaacaa tcgacggaaa gaagtattat    4320
ttcaatctga acactgccga ggctgccacc ggttggcaga ctatcgatgg caagaagtac    4380
```

-continued

```
tactttaacc tcaacactgc cgaagctgcc acaggatggc aaaccatcga cggcaagaag    4440
tactatttta acacaaacac cttcatcgct tctactggct acacaagcat caacggaaag    4500 cattttatt tcaacaccga tggaatcatg cagatcggtg tgttcaaggg accaaacggt    4560
ttcgaatact tcgctccggc taacacagac gctaacaaca tcgagggcca ggctatcttg    4620
taccaaaaca agttcctcac tttgaacggc aagaagtact attttggctc tgacagcaag    4680
gccgtcactg gactgaggac aatcgatggc aagaagtact actttaatac taacacagcc    4740
gttgctgtga ccggctggca gactatcaac ggaaagaagt attatttcaa taccaacact    4800
tcaatcgctt cgaccggtta cactatcatc tctggcaagc attttatttt aacaccgac    4860 ggcatcatgc aaatcggtgt cttcaagggc cccgatggct cgaatactt cgccccgct    4920 aacactgatg ctaacaacat cgagggacag gctatccgtt accaaaaccg cttcctgtac    4980
ctccacgaca acatctacta cttcggcaac aactcaaagg ctgccacagg atgggtgacc    5040
atcgatggta accgttacta cttcgagccc aacactgcca tgggtgctaa cggctacaag    5100
acaatcgaca acaagaactt ctacttccgc aacggtctcc cacagatcgg cgtcttcaag    5160
ggatcaaacg gtttcgagta cttcgctcct gccaacaccg acgccaacaa catcgagggc    5220
caagctatca ggtaccaaaa cagattcctg cacctgctcg gcaagatcta ctacttcgga    5280
aacaactcga aggccgttac tggttggcag acaatcaacg gcaaggtgta ctacttcatg    5340
ccagacaccg ctatggctgc cgctggtggc ctcttcgaaa tcgacggcgt gatctacttc    5400
ttcggcgttg atggagtgaa ggctccgggt atctacggct aa                      5442
```

<210> SEQ ID NO 6
<211> LENGTH: 2505
<212> TYPE: DNA
<213> ORGANISM: Clostridium difficile
<220> FEATURE:
<221> NAME/KEY: misc_feature
<222> LOCATION: (1763)..(1763)
<223> OTHER INFORMATION: n is a, c, g, or t

<400> SEQUENCE: 6

```
atggaaatcg tcaacgaaga catcctgccg aacaacggtt tgatgggcta ctacttcacc      60
gatgagcact tcaaggacct gaagctcatg gctcctatca aggacggaaa cctgaagttc     120
gaggaaaaga aggtcgataa gctgctcgac aaggataaga gcgacgttaa gtcaatcagg     180
tggaccggca gaatcatccc atccaaggat ggagagtaca ctctctctac agaccgtgac     240
gatgtcttga tgcaggtgaa caccgaatcg actatctcca acactctgaa ggtgaacatg     300
aagaagggaa aggagtacaa ggtgcgcatc gaactgcaag ataagaaccct cggttctatc     360 gacaacctct cctctccaaa cctctactgg gagttggatg gcatgaagaa gatcatcccg     420
gaggaaaact tgttcctgcg tgactacagc aacatcgaaa aggacgatcc cttcatccct     480
aacaacaact tcttcgatcc caagctgatg tctgactggg aggacgaaga tctcgacacc     540
gataacgaca acatccctga cagctacgag cgcaacggat acactatcaa ggatctcatc     600
gctgtgaagt gggaggactc cttcgccgaa cagggttaca agaagtacgt ctcaaactac     660
ttggagtcga acacagctgg tgaccccgtac accgactacg aaaaggcctc cggctctttc     720
gataaggcta tcaagaccga ggctagggac ccactcgtcg ctgcttaccc catcgtggga     780
gtcggtatgg agaagttgat catcagcact aacgaacacg cttcaactga ccagggcaag     840
acagtttcaa gagccaccac taactcgaag accgagtcca cactgctgg cgtttccgtg      900
```

```
aacgtcggct accagaacgg attcaccgcc aacgttacaa ccaactactc gcacactaca        960
gataactcca ccgctgtgca agactctaac ggagagagct ggaacactgg tctgtctatc       1020
aacaagggcg aaagcgctta catcaacgcc aacgtccgct actacaacac tggcacagcc       1080
cccatgtaca aggtgacccc taccactaac ctcgtcttgg atggagacac actgtctacc       1140
atcaaggctc aggagaacca atcggaaac aacctcagcc ccggtgacac ataccctaag        1200
aagggattgt caccactggc cctcaacact atggaccagt tcagctcaag gttgatcccg       1260
atcaactacg atcaactcaa gaagttggac gctggcaagc agatcaagct ggagacaacc       1320
caagtctccg gtaacttcgg caccaagaac tcgtccggcc agatcgttac tgaaggaaac       1380
agctggtcag attacatctc acaaatcgac tcgatctccg cctctatcat cctggacaca       1440
gagaacgaat cctacgagcg tcgcgtgacc gctaagaact gcaggaccc cgaggacaag        1500
acaccggaac tgaccatcgg cgaggccatc gaaaaggctt tcggtgccac caagaaggac       1560
ggcttgctgt acttcaacga tatccctatc gacgagtcct gcgttgaact gatcttcgac       1620
gataacactg ctaacaagat caaggattcc ctgaagacac tctctgacaa gaagatctac       1680
aacgtgaagc tcgagagggg tatgaacatc ttgatcaaga cccccactta cttcacaaac       1740
ttcgacgatt acaacaacta ccnttctacc tggagcaacg tcaacactac aaaccaggac       1800
ggactgcaag gttcggccaa caagctcaac ggcgagacca agatcaagat cccaatgagc       1860
gaactgaagc cgtacaagag atacgtgttc tcaggctact cgaaggaccc actcactagc       1920
aactcaatca tcgtgaagat caaggctaag gaggaaaaga ccgactacct ggtccccgag       1980
cagggctaca ctaagttctc ttacgagttc gaaaccactg agaaggactc tagcaacatc       2040
gaaatcaccc tcatcggcag cggaacaacc tacttggaca acctgtcaat caccgagttg       2100
aactcgactc ccgaaatcct ggacgagccc gaagtcaaga tccctaccga tcaggagatc       2160
atggacgctc acaagatcta cttcgccgac ctgaacttca cccctctac tggaaacaca       2220
tacatcaacg gcatgtactt cgctcctaca caaaccaaca aggaggccct ggactacatc       2280
cagaagtacc gtgtcgaagc cactctccaa tactccggtt tcaaggatat cggcacaaag       2340
gacaaggaga tgaggaacta cttgggtgac ccaaaccagc cgaagaccaa ctacgtgaac       2400
ctgagatcat acttcactgg tggcgagaac atcatgacat acaagaagct gcgtatctac       2460
gctatcaccc ctgacgaccg tgaactcttg gttttgtccg tggac                      2505

<210> SEQ ID NO 7
<211> LENGTH: 1608
<212> TYPE: DNA
<213> ORGANISM: Clostridium difficile

<400> SEQUENCE: 7
atggtcagcg gtctcatcta catcaacgac tcgttgtact acttcaagcc ccctgtgaac        60
aacctgatca caggtttcgt taccgtgggc gacgataagt actacttcaa cccaatcaac       120
ggtggcgctg cctccatcgg cgagaccatc atcgacgata agaactacta cttcaaccag       180
agcggagttc tccaaactgg tgtgttctca acagaggacg gtttcaagta cttcgctccg       240
gccaacacct tggacgaaaa cctggagggt gaagccatcg acttcactgg caagttgatc       300
atcgatgaga acatctacta cttcgacgat aactaccgcg tgctgtgga gtggaaggaa        360
ctcgacggcg agatgcacta cttctctcca gaaaccggca aggccttcaa gggattgaac       420
cagatcggtg actacaagta ctacttcaac tcggatggcg tgatgcaaaa gggattcgtc       480
tccatcaacg acaacaagca ctacttcgac gattccggtg ttatgaaagt gggctacaca       540
```

-continued

```
gagatcgacg gcaagcactt ctacttcgct gagaacggag aaatgcagat cggtgtcttc      600
aacactgaag atggtttcaa gtacttcgcc caccacaacg aagatttggg caacgaggaa      660
ggagaggaaa tcagctactc aggcatcctg aacttcaaca acaagatcta ctacttcgat      720
gactctttca ccgctgtggt cggatggaag gacctggagg atggtagcaa gtactacttc      780
gacgaggata ctgctgaagc ctacatcggc ctgtcgctca tcaacgacgg acagtactac      840
ttcaacgacg atggcatcat gcaagtcgga ttcgttacca tcaacgacaa ggtgttctac      900
ttctcggatt ccggtatcat cgagtctggc gtccagaaca tcgacgataa ctacttctac      960
atcgacgata acgaatcgt gcaaatcggt gtcttcgaca caagcgatgg ctacaagtac     1020
ttcgctcccg ccaacaccgt gaacgacaac atctacggac aggctgtgga gtactcaggc     1080
ctggtccgtg ttggagaaga cgtgtactac ttcggcgaga cctacactat cgaaactgga     1140
tggatctacg acatggagaa cgaatctgac aagtactact tcaaccctga caaagaag      1200 gcctgcaagg gtatcaacct gatcgacgat atcaagtact acttcgatga aaagggtatc     1260
atgcgcaccg gcctcatctc attcgaaaac aacaactact acttcaacga gaacggagaa     1320
atgcaattcg gttacatcaa catcgaggac aagatgttct acttcggaga gatggtgtc     1380 atgcagatcg gtgttttcaa cactccagac ggcttcaagt acttcgctca ccaaaacaca     1440
ctcgacgaga acttcgaggg agaatccatc aactacactg ttggttgga cctggatgag     1500 aagaggtact acttcaccga cgaatacatc gctgccactg gctccgtcat catcgacgga     1560
gaggaatact acttcgaccc ggatacagcc cagctggtca tctctgaa              1608
```

<210> SEQ ID NO 8
<211> LENGTH: 1317
<212> TYPE: DNA
<213> ORGANISM: Clostridium difficile

<400> SEQUENCE: 8

```
atggtgaccg gtgtcttcaa gggtcccaac ggcttcgagt acttcgctcc cgccaacact       60
cacaacaaca catcgaagg tcaagctatc gtctaccaaa acaagttctt gaccctgaac      120
ggcaagaagt attattttga caacgattct aaggccgtta ctggctggca acaatcgac      180 ggaaagaagt attatttcaa tctgaacact gccgaggctg ccaccggttg cagactatc      240 gatggcaaga agtactactt taacctcaac actgccgaag ctgccacagg atggcaaacc     300
atcgacggca agaagtacta ttttaacaca aacaccttca tcgcttctac tggctacaca      360
agcatcaacg gaaagcattt ttatttcaac accgatggaa tcatgcagat cggtgtgttc      420
aagggaccaa acggtttcga atacttcgct ccggctaaca cagacgctaa caacatcgag      480
ggccaggcta tcttgtacca aaacaagttc ctcactttga acggcaagaa gtactatttt      540
ggctctgaca gcaaggccgt cactggactg aggacaatcg atggcaagaa gtactacttt      600
aatactaaca cagccgttgc tgtgaccggc tggcagacta tcaacggaaa gaagtattat      660
ttcaatacca acacttcaat cgcttcgacc ggttacacta tcatctctgg caagcatttt      720
tattttaaca ccgacggcat catgcaaatc ggtgtcttca agggccccga tggcttcgaa      780
tacttcgccc ccgctaacac tgatgctaac aacatcgagg acaggctat ccgttaccaa      840 aaccgcttcc tgtacctcca cgacaacatc tactacttcg caacaactc aaaggctgcc      900 acaggatggg tgaccatcga tggtaaccgt tactacttcg agcccaacac tgccatgggt      960
gctaacggct acaagacaat cgacaacaag aacttctact ccgcaacgg tctcccacag     1020
```

```
atcggcgtct tcaagggatc aaacggtttc gagtacttcg ctcctgccaa caccgacgcc   1080
aacaacatcg agggccaagc tatcaggtac caaaacagat tcctgcacct gctcggcaag   1140
atctactact tcggaaacaa ctcgaaggcc gttactggtt ggcagacaat caacggcaag   1200
gtgtactact tcatgccaga caccgctatg gctgccgctg gtggcctctt cgaaatcgac   1260
ggcgtgatct acttcttcgg cgttgatgga gtgaaggctc cgggtatcta cggctaa      1317

<210> SEQ ID NO 9
<211> LENGTH: 1820
<212> TYPE: PRT
<213> ORGANISM: Artificial Sequence
<220> FEATURE:
<223> OTHER INFORMATION: Triple toxin vaccine BV1420
<220> FEATURE:
<221> NAME/KEY: SITE
<222> LOCATION: (595)..(595)
<223> OTHER INFORMATION: Xaa can be any naturally occurring amino acid

<400> SEQUENCE: 9

Met Glu Ile Val Asn Glu Asp Ile Leu Pro Asn Asn Gly Leu Met Gly
1               5                   10                  15

Tyr Tyr Phe Thr Asp Glu His Phe Lys Asp Leu Lys Leu Met Ala Pro
            20                  25                  30

Ile Lys Asp Gly Asn Leu Lys Phe Glu Glu Lys Lys Val Asp Lys Leu
        35                  40                  45

Leu Asp Lys Asp Lys Ser Asp Val Lys Ser Ile Arg Trp Thr Gly Arg
    50                  55                  60

Ile Ile Pro Ser Lys Asp Gly Glu Tyr Thr Leu Ser Thr Asp Arg Asp
65                  70                  75                  80

Asp Val Leu Met Gln Val Asn Thr Glu Ser Thr Ile Ser Asn Thr Leu
                85                  90                  95

Lys Val Asn Met Lys Lys Gly Lys Glu Tyr Lys Val Arg Ile Glu Leu
            100                 105                 110

Gln Asp Lys Asn Leu Gly Ser Ile Asp Asn Leu Ser Ser Pro Asn Leu
        115                 120                 125

Tyr Trp Glu Leu Asp Gly Met Lys Lys Ile Ile Pro Glu Glu Asn Leu
    130                 135                 140

Phe Leu Arg Asp Tyr Ser Asn Ile Glu Lys Asp Asp Pro Phe Ile Pro
145                 150                 155                 160

Asn Asn Asn Phe Phe Asp Pro Lys Leu Arg Ala Arg Arg Arg Lys Lys
                165                 170                 175

Arg Met Ser Asp Trp Glu Asp Glu Asp Leu Asp Thr Asp Asn Asp Asn
            180                 185                 190

Ile Pro Asp Ser Tyr Glu Arg Asn Gly Tyr Thr Ile Lys Asp Leu Ile
        195                 200                 205

Ala Val Lys Trp Glu Asp Ser Phe Ala Glu Gln Gly Tyr Lys Lys Tyr
    210                 215                 220

Val Ser Asn Tyr Leu Glu Ser Asn Thr Ala Gly Asp Pro Tyr Asp Tyr
225                 230                 235                 240

Glu Lys Ala Ser Gly Ser Phe Asp Lys Ala Ile Lys Thr Glu Ala Arg
                245                 250                 255

Asp Pro Leu Val Ala Ala Tyr Pro Ile Val Gly Val Gly Met Glu Lys
            260                 265                 270

Leu Ile Ile Ser Thr Asn Glu His Ala Ser Thr Asp Gln Gly Lys Thr
        275                 280                 285

Val Ser Arg Ala Thr Thr Asn Ser Lys Thr Glu Ser Asn Thr Ala Gly
```

```
                    290                 295                 300
Val Ser Val Asn Val Gly Tyr Gln Asn Gly Phe Thr Ala Asn Val Thr
305                 310                 315                 320

Thr Asn Tyr Ser His Thr Thr Asp Asn Ser Thr Ala Val Gln Asp Ser
                    325                 330                 335

Asn Gly Glu Ser Trp Asn Thr Gly Leu Ser Ile Asn Lys Gly Glu Ser
                340                 345                 350

Ala Tyr Ile Asn Ala Asn Val Arg Tyr Tyr Asn Thr Gly Thr Ala Pro
                355                 360                 365

Met Tyr Lys Val Thr Pro Thr Thr Asn Leu Val Leu Asp Gly Asp Thr
            370                 375                 380

Leu Ser Thr Ile Lys Ala Gln Glu Asn Gln Ile Gly Asn Asn Leu Ser
385                 390                 395                 400

Pro Gly Asp Thr Tyr Pro Lys Lys Gly Leu Ser Pro Leu Ala Leu Asn
                405                 410                 415

Thr Met Asp Gln Phe Ser Ser Arg Leu Ile Pro Ile Asn Tyr Asp Gln
                420                 425                 430

Leu Lys Lys Leu Asp Ala Gly Lys Gln Ile Lys Leu Glu Thr Thr Gln
                435                 440                 445

Val Ser Gly Asn Phe Gly Thr Lys Asn Ser Ser Gly Gln Ile Val Thr
450                 455                 460

Glu Gly Asn Ser Trp Ser Asp Tyr Ile Ser Gln Ile Asp Ser Ile Ser
465                 470                 475                 480

Ala Ser Ile Ile Leu Asp Thr Glu Asn Glu Ser Tyr Glu Arg Arg Val
                485                 490                 495

Thr Ala Lys Asn Leu Gln Asp Pro Glu Asp Lys Thr Pro Glu Leu Thr
                500                 505                 510

Ile Gly Glu Ala Ile Glu Lys Ala Phe Gly Ala Thr Lys Lys Asp Gly
                515                 520                 525

Leu Leu Tyr Phe Asn Asp Ile Pro Ile Asp Glu Ser Cys Val Glu Leu
                530                 535                 540

Ile Phe Asp Asp Asn Thr Ala Asn Lys Ile Lys Asp Ser Leu Lys Thr
545                 550                 555                 560

Leu Ser Asp Lys Lys Ile Tyr Asn Val Lys Leu Glu Arg Gly Met Asn
                565                 570                 575

Ile Leu Ile Lys Thr Pro Thr Tyr Phe Thr Asn Phe Asp Asp Tyr Asn
                580                 585                 590

Asn Tyr Xaa Ser Thr Trp Ser Asn Val Asn Thr Thr Asn Gln Asp Gly
                595                 600                 605

Leu Gln Gly Ser Ala Asn Lys Leu Asn Gly Glu Thr Lys Ile Lys Ile
            610                 615                 620

Pro Met Ser Glu Leu Lys Pro Tyr Lys Arg Tyr Val Phe Ser Gly Tyr
625                 630                 635                 640

Ser Lys Asp Pro Leu Thr Ser Asn Ser Ile Ile Val Lys Ile Lys Ala
                645                 650                 655

Lys Glu Glu Lys Thr Asp Tyr Leu Val Pro Glu Gln Gly Tyr Thr Lys
                660                 665                 670

Phe Ser Tyr Glu Phe Glu Thr Thr Glu Lys Asp Ser Ser Asn Ile Glu
                675                 680                 685

Ile Thr Leu Ile Gly Ser Gly Thr Thr Tyr Leu Asp Asn Leu Ser Ile
            690                 695                 700

Thr Glu Leu Asn Ser Thr Pro Glu Ile Leu Asp Glu Pro Glu Val Lys
705                 710                 715                 720
```

```
Ile Pro Thr Asp Gln Glu Ile Met Asp Ala His Lys Ile Tyr Phe Ala
            725                 730                 735

Asp Leu Asn Phe Asn Pro Ser Thr Gly Asn Thr Tyr Ile Asn Gly Met
            740                 745                 750

Tyr Phe Ala Pro Thr Gln Thr Asn Lys Glu Ala Leu Asp Tyr Ile Gln
            755                 760                 765

Lys Tyr Arg Val Glu Ala Thr Leu Gln Tyr Ser Gly Phe Lys Asp Ile
770                 775                 780

Gly Thr Lys Asp Lys Glu Met Arg Asn Tyr Leu Gly Asp Pro Asn Gln
785                 790                 795                 800

Pro Lys Thr Asn Tyr Val Asn Leu Arg Ser Tyr Phe Thr Gly Gly Glu
            805                 810                 815

Asn Ile Met Thr Tyr Lys Lys Leu Arg Ile Tyr Ala Ile Thr Pro Asp
            820                 825                 830

Asp Arg Glu Leu Leu Val Leu Ser Val Asp Ala Ser Met Val Ser Gly
            835                 840                 845

Leu Ile Tyr Ile Asn Asp Ser Leu Tyr Tyr Phe Lys Pro Pro Val Asn
850                 855                 860

Asn Leu Ile Thr Gly Phe Val Thr Val Gly Asp Asp Lys Tyr Tyr Phe
865                 870                 875                 880

Asn Pro Ile Asn Gly Gly Ala Ala Ser Ile Gly Glu Thr Ile Ile Asp
            885                 890                 895

Asp Lys Asn Tyr Tyr Phe Asn Gln Ser Gly Val Leu Gln Thr Gly Val
            900                 905                 910

Phe Ser Thr Glu Asp Gly Phe Lys Tyr Phe Ala Pro Ala Asn Thr Leu
            915                 920                 925

Asp Glu Asn Leu Glu Gly Glu Ala Ile Asp Phe Thr Gly Lys Leu Ile
            930                 935                 940

Ile Asp Glu Asn Ile Tyr Tyr Phe Asp Asp Asn Tyr Arg Gly Ala Val
945                 950                 955                 960

Glu Trp Lys Glu Leu Asp Gly Glu Met His Tyr Phe Ser Pro Glu Thr
            965                 970                 975

Gly Lys Ala Phe Lys Gly Leu Asn Gln Ile Gly Asp Tyr Lys Tyr Tyr
            980                 985                 990

Phe Asn Ser Asp Gly Val Met Gln Lys Gly Phe Val Ser Ile Asn Asp
            995                 1000                1005

Asn Lys His Tyr Phe Asp Asp Ser Gly Val Met Lys Val Gly Tyr
    1010                1015                1020

Thr Glu Ile Asp Gly Lys His Phe Tyr Phe Ala Glu Asn Gly Glu
    1025                1030                1035

Met Gln Ile Gly Val Phe Asn Thr Glu Asp Gly Phe Lys Tyr Phe
    1040                1045                1050

Ala His His Asn Glu Asp Leu Gly Asn Glu Glu Gly Glu Glu Ile
    1055                1060                1065

Ser Tyr Ser Gly Ile Leu Asn Phe Asn Asn Lys Ile Tyr Tyr Phe
    1070                1075                1080

Asp Asp Ser Phe Thr Ala Val Val Gly Trp Lys Asp Leu Glu Asp
    1085                1090                1095

Gly Ser Lys Tyr Tyr Phe Asp Glu Asp Thr Ala Glu Ala Tyr Ile
    1100                1105                1110

Gly Leu Ser Leu Ile Asn Asp Gly Gln Tyr Tyr Phe Asn Asp Asp
    1115                1120                1125
```

-continued

```
Gly Ile Met Gln Val Gly Phe Val Thr Ile Asn Asp Lys Val Phe
1130                1135                1140

Tyr Phe Ser Asp Ser Gly Ile Ile Glu Ser Gly Val Gln Asn Ile
    1145                1150                1155

Asp Asp Asn Tyr Phe Tyr Ile Asp Asp Asn Gly Ile Val Gln Ile
    1160                1165                1170

Gly Val Phe Asp Thr Ser Asp Gly Tyr Lys Tyr Phe Ala Pro Ala
1175                1180                1185

Asn Thr Val Asn Asp Asn Ile Tyr Gly Gln Ala Val Glu Tyr Ser
    1190                1195                1200

Gly Leu Val Arg Val Gly Glu Asp Val Tyr Tyr Phe Gly Glu Thr
1205                1210                1215

Tyr Thr Ile Glu Thr Gly Trp Ile Tyr Asp Met Glu Asn Glu Ser
    1220                1225                1230

Asp Lys Tyr Tyr Phe Asn Pro Glu Thr Lys Lys Ala Cys Lys Gly
    1235                1240                1245

Ile Asn Leu Ile Asp Asp Ile Lys Tyr Tyr Phe Asp Glu Lys Gly
1250                1255                1260

Ile Met Arg Thr Gly Leu Ile Ser Phe Glu Asn Asn Asn Tyr Tyr
1265                1270                1275

Phe Asn Glu Asn Gly Glu Met Gln Phe Gly Tyr Ile Asn Ile Glu
    1280                1285                1290

Asp Lys Met Phe Tyr Phe Gly Glu Asp Gly Val Met Gln Ile Gly
    1295                1300                1305

Val Phe Asn Thr Pro Asp Gly Phe Lys Tyr Phe Ala His Gln Asn
    1310                1315                1320

Thr Leu Asp Glu Asn Phe Glu Gly Glu Ser Ile Asn Tyr Thr Gly
    1325                1330                1335

Trp Leu Asp Leu Asp Glu Lys Arg Tyr Tyr Phe Thr Asp Glu Tyr
    1340                1345                1350

Ile Ala Ala Thr Gly Ser Val Ile Ile Asp Gly Glu Glu Tyr Tyr
    1355                1360                1365

Phe Asp Pro Asp Thr Ala Gln Leu Val Ile Ser Glu Ser Arg Met
    1370                1375                1380

Val Thr Gly Val Phe Lys Gly Pro Asn Gly Phe Glu Tyr Phe Ala
    1385                1390                1395

Pro Ala Asn Thr His Asn Asn Asn Ile Glu Gly Gln Ala Ile Val
    1400                1405                1410

Tyr Gln Asn Lys Phe Leu Thr Leu Asn Gly Lys Lys Tyr Tyr Phe
    1415                1420                1425

Asp Asn Asp Ser Lys Ala Val Thr Gly Trp Gln Thr Ile Asp Gly
    1430                1435                1440

Lys Lys Tyr Tyr Phe Asn Leu Asn Thr Ala Glu Ala Ala Thr Gly
1445                1450                1455

Trp Gln Thr Ile Asp Gly Lys Lys Tyr Tyr Phe Asn Leu Asn Thr
    1460                1465                1470

Ala Glu Ala Ala Thr Gly Trp Gln Thr Ile Asp Gly Lys Lys Tyr
    1475                1480                1485

Tyr Phe Asn Thr Asn Thr Phe Ile Ala Ser Thr Gly Tyr Thr Ser
    1490                1495                1500

Ile Asn Gly Lys His Phe Tyr Phe Asn Thr Asp Gly Ile Met Gln
    1505                1510                1515

Ile Gly Val Phe Lys Gly Pro Asn Gly Phe Glu Tyr Phe Ala Pro
```

```
                1520                1525                1530
Ala Asn Thr Asp Ala Asn Asn Ile Glu Gly Gln Ala Ile Leu Tyr
        1535                1540                1545

Gln Asn Lys Phe Leu Thr Leu Asn Gly Lys Lys Tyr Tyr Phe Gly
        1550                1555                1560

Ser Asp Ser Lys Ala Val Thr Gly Leu Arg Thr Ile Asp Gly Lys
        1565                1570                1575

Lys Tyr Tyr Phe Asn Thr Asn Thr Ala Val Ala Val Thr Gly Trp
        1580                1585                1590

Gln Thr Ile Asn Gly Lys Lys Tyr Tyr Phe Asn Thr Asn Thr Ser
        1595                1600                1605

Ile Ala Ser Thr Gly Tyr Thr Ile Ile Ser Gly Lys His Phe Tyr
        1610                1615                1620

Phe Asn Thr Asp Gly Ile Met Gln Ile Gly Val Phe Lys Gly Pro
        1625                1630                1635

Asp Gly Phe Glu Tyr Phe Ala Pro Ala Asn Thr Asp Ala Asn Asn
        1640                1645                1650

Ile Glu Gly Gln Ala Ile Arg Tyr Gln Asn Arg Phe Leu Tyr Leu
        1655                1660                1665

His Asp Asn Ile Tyr Tyr Phe Gly Asn Asn Ser Lys Ala Ala Thr
        1670                1675                1680

Gly Trp Val Thr Ile Asp Gly Asn Arg Tyr Tyr Phe Glu Pro Asn
        1685                1690                1695

Thr Ala Met Gly Ala Asn Gly Tyr Lys Thr Ile Asp Asn Lys Asn
        1700                1705                1710

Phe Tyr Phe Arg Asn Gly Leu Pro Gln Ile Gly Val Phe Lys Gly
        1715                1720                1725

Ser Asn Gly Phe Glu Tyr Phe Ala Pro Ala Asn Thr Asp Ala Asn
        1730                1735                1740

Asn Ile Glu Gly Gln Ala Ile Arg Tyr Gln Asn Arg Phe Leu His
        1745                1750                1755

Leu Leu Gly Lys Ile Tyr Tyr Phe Gly Asn Asn Ser Lys Ala Val
        1760                1765                1770

Thr Gly Trp Gln Thr Ile Asn Gly Lys Val Tyr Tyr Phe Met Pro
        1775                1780                1785

Asp Thr Ala Met Ala Ala Ala Gly Gly Leu Phe Glu Ile Asp Gly
        1790                1795                1800

Val Ile Tyr Phe Phe Gly Val Asp Gly Val Lys Ala Pro Gly Ile
        1805                1810                1815

Tyr Gly
    1820

<210> SEQ ID NO 10
<211> LENGTH: 842
<212> TYPE: PRT
<213> ORGANISM: Clostridium difficile
<220> FEATURE:
<221> NAME/KEY: SITE
<222> LOCATION: (595)..(595)
<223> OTHER INFORMATION: Xaa can be any naturally occurring amino acid

<400> SEQUENCE: 10

Met Glu Ile Val Asn Glu Asp Ile Leu Pro Asn Asn Gly Leu Met Gly
1               5                   10                  15

Tyr Tyr Phe Thr Asp Glu His Phe Lys Asp Leu Lys Leu Met Ala Pro
            20                  25                  30
```

```
Ile Lys Asp Gly Asn Leu Lys Phe Glu Glu Lys Val Asp Lys Leu
         35                  40                  45

Leu Asp Lys Asp Lys Ser Asp Val Lys Ser Ile Arg Trp Thr Gly Arg
 50                  55                  60

Ile Ile Pro Ser Lys Asp Gly Glu Tyr Thr Leu Ser Thr Asp Arg Asp
 65                  70                  75                  80

Asp Val Leu Met Gln Val Asn Thr Glu Ser Thr Ile Ser Asn Thr Leu
                 85                  90                  95

Lys Val Asn Met Lys Lys Gly Lys Glu Tyr Lys Val Arg Ile Glu Leu
                100                 105                 110

Gln Asp Lys Asn Leu Gly Ser Ile Asp Asn Leu Ser Ser Pro Asn Leu
             115                 120                 125

Tyr Trp Glu Leu Asp Gly Met Lys Lys Ile Ile Pro Glu Glu Asn Leu
         130                 135                 140

Phe Leu Arg Asp Tyr Ser Asn Ile Glu Lys Asp Asp Pro Phe Ile Pro
145                 150                 155                 160

Asn Asn Asn Phe Phe Asp Pro Lys Leu Arg Ala Arg Arg Lys Lys
                 165                 170                 175

Arg Met Ser Asp Trp Glu Asp Glu Asp Leu Asp Thr Asp Asn Asp Asn
             180                 185                 190

Ile Pro Asp Ser Tyr Glu Arg Asn Gly Tyr Thr Ile Lys Asp Leu Ile
         195                 200                 205

Ala Val Lys Trp Glu Asp Ser Phe Ala Glu Gln Gly Tyr Lys Lys Tyr
         210                 215                 220

Val Ser Asn Tyr Leu Glu Ser Asn Thr Ala Gly Asp Pro Tyr Asp Tyr
225                 230                 235                 240

Glu Lys Ala Ser Gly Ser Phe Asp Lys Ala Ile Lys Thr Glu Ala Arg
                 245                 250                 255

Asp Pro Leu Val Ala Ala Tyr Pro Ile Val Gly Val Gly Met Glu Lys
             260                 265                 270

Leu Ile Ile Ser Thr Asn Glu His Ala Ser Thr Asp Gln Gly Lys Thr
         275                 280                 285

Val Ser Arg Ala Thr Thr Asn Ser Lys Thr Glu Ser Asn Thr Ala Gly
         290                 295                 300

Val Ser Val Asn Val Gly Tyr Gln Asn Gly Phe Thr Ala Asn Val Thr
305                 310                 315                 320

Thr Asn Tyr Ser His Thr Thr Asp Asn Ser Thr Ala Val Gln Asp Ser
                 325                 330                 335

Asn Gly Glu Ser Trp Asn Thr Gly Leu Ser Ile Asn Lys Gly Glu Ser
             340                 345                 350

Ala Tyr Ile Asn Ala Asn Val Arg Tyr Tyr Asn Thr Gly Thr Ala Pro
         355                 360                 365

Met Tyr Lys Val Thr Pro Thr Thr Asn Leu Val Leu Asp Gly Asp Thr
         370                 375                 380

Leu Ser Thr Ile Lys Ala Gln Glu Asn Gln Ile Gly Asn Asn Leu Ser
385                 390                 395                 400

Pro Gly Asp Thr Tyr Pro Lys Lys Gly Leu Ser Pro Leu Ala Leu Asn
                 405                 410                 415

Thr Met Asp Gln Phe Ser Ser Arg Leu Ile Pro Ile Asn Tyr Asp Gln
             420                 425                 430

Leu Lys Lys Leu Asp Ala Gly Lys Gln Ile Lys Leu Glu Thr Thr Gln
         435                 440                 445
```

Val Ser Gly Asn Phe Gly Thr Lys Asn Ser Ser Gly Gln Ile Val Thr
450                 455                 460

Glu Gly Asn Ser Trp Ser Asp Tyr Ile Ser Gln Ile Asp Ser Ile Ser
465                 470                 475                 480

Ala Ser Ile Ile Leu Asp Thr Glu Asn Glu Ser Tyr Glu Arg Arg Val
                485                 490                 495

Thr Ala Lys Asn Leu Gln Asp Pro Glu Asp Lys Thr Pro Glu Leu Thr
            500                 505                 510

Ile Gly Glu Ala Ile Glu Lys Ala Phe Gly Ala Thr Lys Lys Asp Gly
        515                 520                 525

Leu Leu Tyr Phe Asn Asp Ile Pro Ile Asp Glu Ser Cys Val Glu Leu
530                 535                 540

Ile Phe Asp Asp Asn Thr Ala Asn Lys Ile Lys Asp Ser Leu Lys Thr
545                 550                 555                 560

Leu Ser Asp Lys Lys Ile Tyr Asn Val Lys Leu Glu Arg Gly Met Asn
                565                 570                 575

Ile Leu Ile Lys Thr Pro Thr Tyr Phe Thr Asn Phe Asp Tyr Asn
            580                 585                 590

Asn Tyr Xaa Ser Thr Trp Ser Asn Val Asn Thr Thr Asn Gln Asp Gly
        595                 600                 605

Leu Gln Gly Ser Ala Asn Lys Leu Asn Gly Glu Thr Lys Ile Lys Ile
610                 615                 620

Pro Met Ser Glu Leu Lys Pro Tyr Lys Arg Tyr Val Phe Ser Gly Tyr
625                 630                 635                 640

Ser Lys Asp Pro Leu Thr Ser Asn Ser Ile Ile Val Lys Ile Lys Ala
                645                 650                 655

Lys Glu Glu Lys Thr Asp Tyr Leu Val Pro Glu Gln Gly Tyr Thr Lys
            660                 665                 670

Phe Ser Tyr Glu Phe Glu Thr Thr Glu Lys Asp Ser Ser Asn Ile Glu
        675                 680                 685

Ile Thr Leu Ile Gly Ser Gly Thr Thr Tyr Leu Asp Asn Leu Ser Ile
690                 695                 700

Thr Glu Leu Asn Ser Thr Pro Glu Ile Leu Asp Glu Pro Glu Val Lys
705                 710                 715                 720

Ile Pro Thr Asp Gln Glu Ile Met Asp Ala His Lys Ile Tyr Phe Ala
                725                 730                 735

Asp Leu Asn Phe Asn Pro Ser Thr Gly Asn Thr Tyr Ile Asn Gly Met
            740                 745                 750

Tyr Phe Ala Pro Thr Gln Thr Asn Lys Glu Ala Leu Asp Tyr Ile Gln
        755                 760                 765

Lys Tyr Arg Val Glu Ala Thr Leu Gln Tyr Ser Gly Phe Lys Asp Ile
770                 775                 780

Gly Thr Lys Asp Lys Glu Met Arg Asn Tyr Leu Gly Asp Pro Asn Gln
785                 790                 795                 800

Pro Lys Thr Asn Tyr Val Asn Leu Arg Ser Tyr Phe Thr Gly Gly Glu
                805                 810                 815

Asn Ile Met Thr Tyr Lys Lys Leu Arg Ile Tyr Ala Ile Thr Pro Asp
            820                 825                 830

Asp Arg Glu Leu Leu Val Leu Ser Val Asp
        835                 840

<210> SEQ ID NO 11
<211> LENGTH: 536
<212> TYPE: PRT

<213> ORGANISM: Clostridium difficile

<400> SEQUENCE: 11

```
Met Val Ser Gly Leu Ile Tyr Ile Asn Asp Ser Leu Tyr Tyr Phe Lys
1               5                   10                  15

Pro Pro Val Asn Asn Leu Ile Thr Gly Phe Val Thr Gly Asp Asp
            20                  25                  30

Lys Tyr Tyr Phe Asn Pro Ile Asn Gly Gly Ala Ala Ser Ile Gly Glu
            35                  40                  45

Thr Ile Ile Asp Asp Lys Asn Tyr Tyr Phe Asn Gln Ser Gly Val Leu
50                  55                  60

Gln Thr Gly Val Phe Ser Thr Glu Asp Gly Phe Lys Tyr Phe Ala Pro
65                  70                  75                  80

Ala Asn Thr Leu Asp Glu Asn Leu Glu Gly Glu Ala Ile Asp Phe Thr
                85                  90                  95

Gly Lys Leu Ile Ile Asp Glu Asn Ile Tyr Tyr Phe Asp Asp Asn Tyr
            100                 105                 110

Arg Gly Ala Val Glu Trp Lys Glu Leu Asp Gly Glu Met His Tyr Phe
            115                 120                 125

Ser Pro Glu Thr Gly Lys Ala Phe Lys Gly Leu Asn Gln Ile Gly Asp
        130                 135                 140

Tyr Lys Tyr Tyr Phe Asn Ser Asp Gly Val Met Gln Lys Gly Phe Val
145                 150                 155                 160

Ser Ile Asn Asp Asn Lys His Tyr Phe Asp Asp Ser Gly Val Met Lys
                165                 170                 175

Val Gly Tyr Thr Glu Ile Asp Gly Lys His Phe Tyr Phe Ala Glu Asn
            180                 185                 190

Gly Glu Met Gln Ile Gly Val Phe Asn Thr Glu Asp Gly Phe Lys Tyr
        195                 200                 205

Phe Ala His His Asn Glu Asp Leu Gly Asn Glu Glu Gly Glu Glu Ile
    210                 215                 220

Ser Tyr Ser Gly Ile Leu Asn Phe Asn Asn Lys Ile Tyr Tyr Phe Asp
225                 230                 235                 240

Asp Ser Phe Thr Ala Val Val Gly Trp Lys Asp Leu Glu Asp Gly Ser
                245                 250                 255

Lys Tyr Tyr Phe Asp Glu Asp Thr Ala Glu Ala Tyr Ile Gly Leu Ser
            260                 265                 270

Leu Ile Asn Asp Gly Gln Tyr Tyr Phe Asn Asp Asp Gly Ile Met Gln
        275                 280                 285

Val Gly Phe Val Thr Ile Asn Asp Lys Val Phe Tyr Phe Ser Asp Ser
290                 295                 300

Gly Ile Ile Glu Ser Gly Val Gln Asn Ile Asp Asp Asn Tyr Phe Tyr
305                 310                 315                 320

Ile Asp Asp Asn Gly Ile Val Gln Ile Gly Val Phe Asp Thr Ser Asp
                325                 330                 335

Gly Tyr Lys Tyr Phe Ala Pro Ala Asn Thr Val Asn Asp Asn Ile Tyr
            340                 345                 350

Gly Gln Ala Val Glu Tyr Ser Gly Leu Val Arg Val Gly Glu Asp Val
        355                 360                 365

Tyr Tyr Phe Gly Glu Thr Tyr Thr Ile Glu Thr Gly Trp Ile Tyr Asp
    370                 375                 380

Met Glu Asn Glu Ser Asp Lys Tyr Tyr Phe Asn Pro Glu Thr Lys Lys
385                 390                 395                 400
```

```
Ala Cys Lys Gly Ile Asn Leu Ile Asp Asp Ile Lys Tyr Tyr Phe Asp
                405                 410                 415

Glu Lys Gly Ile Met Arg Thr Gly Leu Ile Ser Phe Glu Asn Asn Asn
            420                 425                 430

Tyr Tyr Phe Asn Glu Asn Gly Glu Met Gln Phe Gly Tyr Ile Asn Ile
        435                 440                 445

Glu Asp Lys Met Phe Tyr Phe Gly Glu Asp Gly Val Met Gln Ile Gly
    450                 455                 460

Val Phe Asn Thr Pro Asp Gly Phe Lys Tyr Phe Ala His Gln Asn Thr
465                 470                 475                 480

Leu Asp Glu Asn Phe Glu Gly Glu Ser Ile Asn Tyr Thr Gly Trp Leu
                485                 490                 495

Asp Leu Asp Glu Lys Arg Tyr Tyr Phe Thr Asp Glu Tyr Ile Ala Ala
            500                 505                 510

Thr Gly Ser Val Ile Ile Asp Gly Glu Glu Tyr Tyr Phe Asp Pro Asp
        515                 520                 525

Thr Ala Gln Leu Val Ile Ser Glu
    530                 535

<210> SEQ ID NO 12
<211> LENGTH: 438
<212> TYPE: PRT
<213> ORGANISM: Clostridium difficile

<400> SEQUENCE: 12

Met Val Thr Gly Val Phe Lys Gly Pro Asn Gly Phe Glu Tyr Phe Ala
1               5                   10                  15

Pro Ala Asn Thr His Asn Asn Ile Glu Gly Gln Ala Ile Val Tyr
            20                  25                  30

Gln Asn Lys Phe Leu Thr Leu Asn Gly Lys Lys Tyr Tyr Phe Asp Asn
        35                  40                  45

Asp Ser Lys Ala Val Thr Gly Trp Gln Thr Ile Asp Gly Lys Lys Tyr
    50                  55                  60

Tyr Phe Asn Leu Asn Thr Ala Glu Ala Ala Thr Gly Trp Gln Thr Ile
65                  70                  75                  80

Asp Gly Lys Lys Tyr Tyr Phe Asn Leu Asn Thr Ala Glu Ala Ala Thr
                85                  90                  95

Gly Trp Gln Thr Ile Asp Gly Lys Lys Tyr Tyr Phe Asn Thr Asn Thr
            100                 105                 110

Phe Ile Ala Ser Thr Gly Tyr Thr Ser Ile Asn Gly Lys His Phe Tyr
        115                 120                 125

Phe Asn Thr Asp Gly Ile Met Gln Ile Gly Val Phe Lys Gly Pro Asn
    130                 135                 140

Gly Phe Glu Tyr Phe Ala Pro Ala Asn Thr Asp Ala Asn Asn Ile Glu
145                 150                 155                 160

Gly Gln Ala Ile Leu Tyr Gln Asn Lys Phe Leu Thr Leu Asn Gly Lys
                165                 170                 175

Lys Tyr Tyr Phe Gly Ser Asp Ser Lys Ala Val Thr Gly Leu Arg Thr
            180                 185                 190

Ile Asp Gly Lys Lys Tyr Tyr Phe Asn Thr Asn Thr Ala Val Ala Val
        195                 200                 205

Thr Gly Trp Gln Thr Ile Asn Gly Lys Lys Tyr Tyr Phe Asn Thr Asn
    210                 215                 220

Thr Ser Ile Ala Ser Thr Gly Tyr Thr Ile Ile Ser Gly Lys His Phe
225                 230                 235                 240
```

```
Tyr Phe Asn Thr Asp Gly Ile Met Gln Ile Gly Val Phe Lys Gly Pro
                245                 250                 255

Asp Gly Phe Glu Tyr Phe Ala Pro Ala Asn Thr Asp Ala Asn Asn Ile
            260                 265                 270

Glu Gly Gln Ala Ile Arg Tyr Gln Asn Arg Phe Leu Tyr Leu His Asp
        275                 280                 285

Asn Ile Tyr Tyr Phe Gly Asn Asn Ser Lys Ala Ala Thr Gly Trp Val
    290                 295                 300

Thr Ile Asp Gly Asn Arg Tyr Tyr Phe Glu Pro Asn Thr Ala Met Gly
305                 310                 315                 320

Ala Asn Gly Tyr Lys Thr Ile Asp Asn Lys Asn Phe Tyr Phe Arg Asn
                325                 330                 335

Gly Leu Pro Gln Ile Gly Val Phe Lys Gly Ser Asn Gly Phe Glu Tyr
            340                 345                 350

Phe Ala Pro Ala Asn Thr Asp Ala Asn Asn Ile Glu Gly Gln Ala Ile
        355                 360                 365

Arg Tyr Gln Asn Arg Phe Leu His Leu Leu Gly Lys Ile Tyr Tyr Phe
    370                 375                 380

Gly Asn Asn Ser Lys Ala Val Thr Gly Trp Gln Thr Ile Asn Gly Lys
385                 390                 395                 400

Val Tyr Tyr Phe Met Pro Asp Thr Ala Met Ala Ala Ala Gly Gly Leu
                405                 410                 415

Phe Glu Ile Asp Gly Val Ile Tyr Phe Phe Gly Val Asp Gly Val Lys
            420                 425                 430

Ala Pro Gly Ile Tyr Gly
        435
```

<210> SEQ ID NO 13
<211> LENGTH: 5466
<212> TYPE: DNA
<213> ORGANISM: Artificial Sequence
<220> FEATURE:
<223> OTHER INFORMATION: Triple toxin vaccine BV1470
<220> FEATURE:
<221> NAME/KEY: misc_feature
<222> LOCATION: (1787)..(1787)
<223> OTHER INFORMATION: n is a, c, g, or t

<400> SEQUENCE: 13

```
atggaaatcg tcaacgaaga catcctgccg aacaacggtt tgatgggcta ctacttcacc     60
gatgagcact tcaaggacct gaagctcatg gctcctatca aggacggaaa cctgaagttc    120
gaggaaaaga aggtcgataa gctgctcgac aaggataaga gcgacgttaa gtcaatcagg    180
tggaccggca gaatcatccc atccaaggat ggagagtaca ctctctctac agaccgtgac    240
gatgtcttga tgcaggtgaa caccgaatcg actatctcca acactctgaa ggtgaacatg    300
aagaagggaa aggagtacaa ggtgcgcatc gaactgcaag ataagaacct cggttctatc    360
gacaacctct cctctccaaa cctctactgg gagttggatg gcatgaagaa gatcatcccg    420
gaggaaaact tgttcctgcg tgactacagc aacatcgaaa aggacgatcc cttcatccct    480
aacaacaact tcttcgatcc caagctgcgc gctcgccgcc gcaagaagcg catgtctgac    540
tgggaggacg aagatctcga caccgataac gacaacatcc ctgacagcta cgagcgcaac    600
ggatacacta tcaaggatct catcgctgtg aagtgggagg actccttcgc cgaacagggt    660
tacaagaagt acgtctcaaa ctacttggag tcgaacacag ctggtgaccc ctacaccgac    720
tacgaaaagg cctccggctc tttcgataag gctatcaaga ccgaggctag ggacccactc    780
```

```
gtcgctgctt accccatcgt gggagtcggt atggagaagt tgatcatcag cactaacgaa     840
cacgcttcaa ctgaccaggg caagacagtt tcaagagcca ccactaactc gaagaccgag     900
tccaacactg ctggcgtttc cgtgaacgtc ggctaccaga acggattcac cgccaacgtt     960
acaaccaact actcgcacac tacagataac tccaccgctg tgcaagactc taacggagag    1020
agctggaaca ctggtctgtc tatcaacaag ggcgaaagcg cttacatcaa cgccaacgtc    1080
cgctactaca acactggcac agcccccatg tacaaggtga cccctaccac taacctcgtc    1140
ttggatggag acacactgtc taccatcaag gctcaggaga accaaatcgg aaacaacctc    1200
agccccggtg acacataccc taagaaggga ttgtcaccac tggccctcaa cactatggac    1260
cagttcagct caaggttgat cccgatcaac tacgatcaac tcaagaagtt ggacgctggc    1320
aagcagatca agctggagac aacccaagtc tccggtaact tcggcaccaa gaactcgtcc    1380
ggccagatcg ttactgaagg aaacagctgg tcagattaca tctcacaaat cgactcgatc    1440
tccgcctcta tcatcctgga cacagagaac gaatcctacg agcgtcgcgt gaccgctaag    1500
aacttgcagg accccgagga caagacaccg gaactgacca tcggcgaggc catcgaaaag    1560
gctttcggtg ccaccaagaa ggacggcttg ctgtacttca acgatatccc tatcgacgag    1620
tcctgcgttg aactgatctt cgacgataac actgctaaca agatcaagga ttccctgaag    1680
acactctctg acaagaagat ctacaacgtg aagctcgaga ggggtatgaa catcttgatc    1740 aagacccca cttacttcac aaacttcgac gattacaaca actaccnttc tacctggagc    1800
aacgtcaaca ctacaaacca ggacggactg caaggttcgg ccaacaagct caacggcgag    1860
accaagatca agatcccaat gagcgaactg aagccgtaca agagatacgt gttctcaggc    1920
tactcgaagg acccactcac tagcaactca atcatcgtga agatcaaggc taaggaggaa    1980
aagaccgact acctggtccc cgagcagggc tacactaagt tctcttacga gttcgaaacc    2040
actgagaagg actctagcaa catcgaaatc accctcatcg gcagcggaac aacctacttg    2100
gacaacctgt caatcaccga gttgaactcg actcccgaaa tcctggacga gcccgaagtc    2160
aagatcccta ccgatcagga gatcatggac gctcacaaga tctacttcgc cgacctgaac    2220 ttcaaccct ctactggaaa cacatacatc aacggcatgt acttcgctcc tacacaaacc    2280
aacaaggagg ccctggacta catccagaag taccgtgtcg aagccactct ccaatactcc    2340
ggtttcaagg atatcggcac aaaggacaag gagatgagga actacttggg tgacccaaac    2400
cagccgaaga ccaactacgt gaacctgaga tcatacttca ctggtggcga gaacatcatg    2460
acatacaaga agctgcgtat ctacgctatc acccctgacg accgtgaact cttggttttg    2520
tccgtggacg ctagcatggt cagcggtctc atctacatca cgactcgtt gtactacttc    2580 aagcccctg tgaacaacct gatcacaggt tcgttaccg tgggcgacga taagtactac    2640
ttcaacccaa tcaacggtgg cgctgcctcc atcggcgaga ccatcatcga cgataagaac    2700
tactacttca accagagcgg agttctccaa actggtgtgt tctcaacaga ggacggtttc    2760
aagtacttcg ctccggccaa caccttggac gaaaacctgg agggtgaagc catcgacttc    2820
actggcaagt tgatcatcga tgagaacatc tactacttcg acgataacta ccgcggtgct    2880
gtggagtgga aggaactcga cggcgagtg cactacttct ctccagaaac cggcaaggcc    2940
ttcaagggat tgaaccagat cggtgactac aagtactact tcaactcgga tggcgtgatg    3000
caaaagggat tcgtctccat caacgacaac aagcactact tcgacgattc cggtgttatg    3060
aaagtgggct acacagagat cgacggcaag cacttctact tcgctgagaa cggagaaatg    3120
```

```
cagatcggtg tcttcaacac tgaagatggt ttcaagtact tcgcccacca caacgaagat    3180
ttgggcaacg aggaaggaga ggaaatcagc tactcaggca tcctgaactt caacaacaag    3240
atctactact tcgatgactc tttcaccgct gtggtcggat ggaaggacct ggaggatggt    3300
agcaagtact acttcgacga ggatactgct gaagcctaca tcggcctgtc gctcatcaac    3360
gacggacagt actacttcaa cgacgatggc atcatgcaag tcggattcgt taccatcaac    3420
gacaaggtgt tctacttctc ggattccggt atcatcgagt ctggcgtcca gaacatcgac    3480
gataactact tctacatcga cgataacgga atcgtgcaaa tcggtgtctt cgacacaagc    3540
gatggctaca agtacttcgc tcccgccaac accgtgaacg acaacatcta cggacaggct    3600
gtggagtact caggcctggt ccgtgttgga gaagacgtgt actacttcgg cgagacctac    3660
actatcgaaa ctggatggat ctacgacatg gagaacgaat ctgacaagta ctacttcaac    3720
cctgagacaa agaaggcctg caagggtatc aacctgatcg acgatatcaa gtactacttc    3780
gatgaaaagg gtatcatgcg caccggcctc atctcattcg aaaacaacaa ctactacttc    3840
aacgagaacg agaaatgca attcggttac atcaacatcg aggacaagat gttctacttc    3900
ggagaagatg gtgtcatgca gatcggtgtt ttcaacactc cagacggctt caagtacttc    3960
gctcaccaaa acacactcga cgagaacttc gagggagaat ccatcaacta cactggttgg    4020
ttggacctgg atgagaagag gtactacttc accgacgaat acatcgctgc cactggctcc    4080
gtcatcatcg acggagagga atactacttc gacccggata cagcccagct ggtcatctct    4140
gaatctagaa tggtgaccgg tgtcttcaag ggtcccaacg gcttcgagta cttcgctccc    4200
gccaacactc acaacaacaa catcgaaggt caagctatcg tctaccaaaa caagttcttg    4260
accctgaacg gcaagaagta ttattttgac aacgattcta aggccgttac tggctggcaa    4320
acaatcgacg gaaagaagta ttatttcaat ctgaacactg ccgaggctgc caccggttgg    4380
cagactatcg atggcaagaa gtactacttt aacctcaaca ctgccgaagc tgccacagga    4440
tggcaaacca tcgacggcaa gaagtactat tttaacacaa acaccttcat cgcttctact    4500
ggctacacaa gcatcaacgg aaagcatttt tatttcaaca ccgatggaat catgcagatc    4560
ggtgtgttca agggaccaaa cggtttcgaa tacttcgctc cggctaacac agacgctaac    4620
aacatcgagg gccaggctat cttgtaccaa aacaagttcc tcactttgaa cggcaagaag    4680
tactattttg gctctgacag caaggccgtc actggactga ggacaatcga tggcaagaag    4740
tactacttta atactaacac agccgttgct gtgaccggct ggcagactat caacggaaag    4800
aagtattatt tcaataccaa cacttcaatc gcttcgaccg gttacactat catctctggc    4860
aagcattttt attttaacac cgacggcatc atgcaaatcg gtgtcttcaa gggccccgat    4920
ggcttcgaat acttcgcccc cgctaacact gatgctaaca acatcgaggg acaggctatc    4980
cgttaccaaa accgcttcct gtacctccac gacaacatct actacttcgg caacaactca    5040
aaggctgcca caggatgggt gaccatcgat ggtaaccgtt actacttcga gcccaacact    5100
gccatgggtg ctaacggcta caagacaatc gacaacaaga acttctactt ccgcaacggt    5160
ctcccacaga tcggcgtctt caagggatca aacggtttcg agtacttcgc tcctgccaac    5220
accgacgcca acaacatcga gggccaagct atcaggtacc aaaacagatt cctgcacctg    5280
ctcggcaaga tctactactt cggaaacaac tcgaaggccg ttactggttg gcagacaatc    5340
aacggcaagg tgtactactt catgccagac accgctatgg ctgccgctgg tggcctcttc    5400
gaaatcgacg gcgtgatcta cttcttcggc gttgatggag tgaaggctcc gggtatctac    5460
ggctaa                                                               5466
```

<210> SEQ ID NO 14
<211> LENGTH: 2529
<212> TYPE: DNA
<213> ORGANISM: Clostridium difficile
<220> FEATURE:
<221> NAME/KEY: misc_feature
<222> LOCATION: (1787)..(1787)
<223> OTHER INFORMATION: n is a, c, g, or t

<400> SEQUENCE: 14
atggaaatcg tcaacgaaga catcctgccg aacaacggtt tgatgggcta ctacttcacc 60
gatgagcact tcaaggacct gaagctcatg gctcctatca aggacggaaa cctgaagttc 120
gaggaaaaga aggtcgataa gctgctcgac aaggataaga gcgacgttaa gtcaatcagg 180
tggaccggca gaatcatccc atccaaggat ggagagtaca ctctctctac agaccgtgac 240
gatgtcttga tgcaggtgaa caccgaatcg actatctcca acactctgaa ggtgaacatg 300
aagaagggaa aggagtacaa ggtgcgcatc gaactgcaag ataagaacct cggttctatc 360
gacaacctct cctctccaaa cctctactgg gagttggatg gcatgaagaa gatcatcccg 420
gaggaaaact tgttcctgcg tgactacagc aacatcgaaa aggacgatcc cttcatccct 480
aacaacaact tcttcgatcc caagctgcgc gctcgccgcc gcaagaagcg catgtctgac 540
tgggaggacg aagatctcga caccgataac gacaacatcc ctgacagcta cgagcgcaac 600
ggatacacta tcaaggatct catcgctgtg aagtgggagg actccttcgc cgaacagggt 660
tacaagaagt acgtctcaaa ctacttggag tcgaacacag ctggtgaccc ctacaccgac 720
tacgaaaagg cctccggctc tttcgataag gctatcaaga ccgaggctag ggacccactc 780
gtcgctgctt accccatcgt gggagtcggt atggagaagt tgatcatcag cactaacgaa 840
cacgcttcaa ctgaccaggg caagacagtt tcaagagcca ccactaactc gaagaccgag 900
tccaacactg ctggcgtttc cgtgaacgtc ggctaccaga acggattcac cgccaacgtt 960
acaaccaact actcgcacac tacagataac tccaccgctg tgcaagactc taacggagag 1020
agctggaaca ctggtctgtc tatcaacaag ggcgaaagcg cttacatcaa cgccaacgtc 1080
cgctactaca acactggcac agcccccatg tacaaggtga cccctaccac taacctcgtc 1140
ttggatggag acacactgtc taccatcaag gctcaggaga accaaatcgg aaacaacctc 1200
agccccggtg acacataccc taagaaggga ttgtcaccac tggccctcaa cactatggac 1260
cagttcagct caaggttgat cccgatcaac tacgatcaac tcaagaagtt ggacgctggc 1320
aagcagatca agctggagac aacccaagtc tccggtaact tcggcaccaa gaactcgtcc 1380
ggccagatcg ttactgaagg aaacagctgg tcagattaca tctcacaaat cgactcgatc 1440
tccgcctcta tcatcctgga cacagagaac gaatcctacg agcgtcgcgt gaccgctaag 1500
aacttgcagg accccgagga caagacaccg gaactgacca tcggcgaggc catcgaaaag 1560
gctttcggtg ccaccaagaa ggacggcttg ctgtacttca acgatatccc tatcgacgag 1620
tcctgcgttg aactgatctt cgacgataac actgctaaca agatcaagga ttccctgaag 1680
acactctctg acaagaagat ctacaacgtg aagctcgaga ggggtatgaa catcttgatc 1740 aagacccccca cttacttcac aaacttcgac gattacaaca actaccnttc tacctggagc 1800
aacgtcaaca ctacaaacca ggacggactg caaggttcgg ccaacaagct caacggcgag 1860
accaagatca agatcccaat gagcgaactg aagccgtaca agagatacgt gttctcaggc 1920
tactcgaagg acccactcac tagcaactca atcatcgtga agatcaaggc taaggaggaa 1980

-continued

```
aagaccgact acctggtccc cgagcagggc tacactaagt tctcttacga gttcgaaacc   2040
actgagaagg actctagcaa catcgaaatc accctcatcg gcagcggaac aacctacttg   2100
gacaacctgt caatcaccga gttgaactcg actcccgaaa tcctggacga gcccgaagtc   2160
aagatcccta ccgatcagga gatcatggac gctcacaaga tctacttcgc cgacctgaac   2220
ttcaacccct ctactggaaa cacatacatc aacggcatgt acttcgctcc tacacaaacc   2280
aacaaggagg ccctggacta catccagaag taccgtgtcg aagccactct ccaatactcc   2340
ggtttcaagg atatcggcac aaaggacaag gagatgagga actacttggg tgacccaaac   2400
cagccgaaga ccaactacgt gaacctgaga tcatacttca ctggtggcga gaacatcatg   2460
acatacaaga agctgcgtat ctacgctatc acccctgacg accgtgaact cttggttttg   2520
tccgtggac                                                           2529
```

<210> SEQ ID NO 15
<211> LENGTH: 1608
<212> TYPE: DNA
<213> ORGANISM: Clostridium difficile

<400> SEQUENCE: 15

```
atggtcagcg gtctcatcta catcaacgac tcgttgtact acttcaagcc ccctgtgaac     60
aacctgatca caggtttcgt taccgtgggc gacgataagt actacttcaa cccaatcaac    120
ggtggcgctg cctccatcgg cgagaccatc atcgacgata agaactacta cttcaaccag    180
agcggagttc tccaaactgg tgtgttctca acagaggacg gtttcaagta cttcgctccg    240
gccaacacct tggacgaaaa cctggagggt gaagccatcg acttcactgg caagttgatc    300
atcgatgaga acatctacta cttcgacgat aactaccgcg gtgctgtgga gtggaaggaa    360
ctcgacggcg agatgcacta cttctctcca gaaaccggca aggccttcaa gggattgaac    420
cagatcggtg actacaagta ctacttcaac tcggatggcg tgatgcaaaa gggattcgtc    480
tccatcaacg acaacaagca ctacttcgac gattccggtg ttatgaaagt gggctacaca    540
gagatcgacg gcaagcactt ctacttcgct gagaacggag aaatgcagat cggtgtcttc    600
aacactgaag atggtttcaa gtacttcgcc caccacaacg aagatttggg caacgaggaa    660
ggagaggaaa tcagctactc aggcatcctg aacttcaaca acaagatcta ctacttcgat    720
gactctttca ccgctgtggt cggatggaag gacctggagg atggtagcaa gtactacttc    780
gacgaggata ctgctgaagc ctacatcggc ctgtcgctca tcaacgacgg acagtactac    840
ttcaacgacg atggcatcat gcaagtcgga ttcgttacca tcaacgacaa ggtgttctac    900
ttctcggatt ccggtatcat cgagtctggc gtccagaaca tcgacgataa ctacttctac    960
atcgacgata acggaatcgt gcaaatcggt gtcttcgaca caagcgatgg ctacaagtac   1020
ttcgctcccg ccaacaccgt gaacgacaac atctacggac aggctgtgga gtactcaggc   1080
ctggtccgtg ttggagaaga cgtgtactac ttcggcgaga cctacactat cgaaactgga   1140
tggatctacg acatggagaa cgaatctgac aagtactact tcaaccctga gacaaagaag   1200
gcctgcaagg gtatcaacct gatcgacgat atcaagtact acttcgatga aaagggtatc   1260
atgcgcaccg gcctcatctc attcgaaaac aacaactact acttcaacga gaacggagaa   1320
atgcaattcg gttacatcaa catcgaggac aagatgttct acttcggaga agatggtgtc   1380
atgcagatcg gtgttttcaa cactccagac ggcttcaagt acttcgctca ccaaaacaca   1440
ctcgacgaga acttcgaggg agaatccatc aactacactg gttggttgga cctggatgag   1500
aagaggtact acttcaccga cgaatacatc gctgccactg gctccgtcat catcgacgga   1560
```

```
gaggaatact acttcgaccc ggatacagcc cagctggtca tctctgaa               1608

<210> SEQ ID NO 16
<211> LENGTH: 1317
<212> TYPE: DNA
<213> ORGANISM: Clostridium difficile

<400> SEQUENCE: 16
atggtgaccg gtgtcttcaa gggtcccaac ggcttcgagt acttcgctcc cgccaacact     60
cacaacaaca acatcgaagg tcaagctatc gtctaccaaa acaagttctt gaccctgaac    120
ggcaagaagt attattttga caacgattct aaggccgtta ctggctggca aacaatcgac    180
ggaaagaagt attatttcaa tctgaacact gccgaggctg ccaccggttg gcagactatc    240
gatggcaaga agtactactt taacctcaac actgccgaag ctgccacagg atggcaaacc    300
atcgacggca agaagtacta ttttaacaca aacaccttca tcgcttctac tggctacaca    360
agcatcaacg gaaagcattt ttatttcaac accgatggaa tcatgcagat cggtgtgttc    420
aagggaccaa acggtttcga atacttcgct ccggctaaca cagacgctaa caacatcgag    480
ggccaggcta tcttgtacca aaacaagttc ctcactttga acggcaagaa gtactatttt    540
ggctctgaca gcaaggccgt cactggactg aggacaatcg atggcaagaa gtactacttt    600
aatactaaca cagccgttgc tgtgaccggc tggcagacta tcaacggaaa gaagtattat    660
ttcaatacca acacttcaat cgcttcgacc ggttacacta tcatctctgg caagcatttt    720
tattttaaca ccgacggcat catgcaaatc ggtgtcttca agggccccga tggcttcgaa    780
tacttcgccc ccgctaacac tgatgctaac aacatcgagg gacaggctat ccgttaccaa    840
aaccgcttcc tgtacctcca cgacaacatc tactacttcg gcaacaactc aaaggctgcc    900
acaggatggg tgaccatcga tggtaaccgt tactacttcg agcccaacac tgccatgggt    960
gctaacggct acaagacaat cgacaacaag aacttctact tccgcaacgg tctcccacag   1020
atcggcgtct tcaagggatc aaacggtttc gagtacttcg ctcctgccaa caccgacgcc   1080
aacaacatcg agggccaagc tatcaggtac caaaacagat tcctgcacct gctcggcaag   1140
atctactact tcggaaacaa ctcgaaggcc gttactggtt ggcagacaat caacggcaag   1200
gtgtactact tcatgccaga caccgctatg gctgccgctg gtggcctctt cgaaatcgac   1260
ggcgtgatct acttcttcgg cgttgatgga gtgaaggctc cgggtatcta cggctaa      1317

<210> SEQ ID NO 17
<211> LENGTH: 2307
<212> TYPE: PRT
<213> ORGANISM: Artificial Sequence
<220> FEATURE:
<223> OTHER INFORMATION: Triple toxin vaccine BV1512
<220> FEATURE:
<221> NAME/KEY: SITE
<222> LOCATION: (588)..(588)
<223> OTHER INFORMATION: Xaa can be any naturally occurring amino acid

<400> SEQUENCE: 17

Met Glu Ile Val Asn Glu Asp Ile Leu Pro Asn Asn Gly Leu Met Gly
1               5                   10                  15

Tyr Tyr Phe Thr Asp Glu His Phe Lys Asp Leu Lys Leu Met Ala Pro
            20                  25                  30

Ile Lys Asp Gly Asn Leu Lys Phe Glu Glu Lys Lys Val Asp Lys Leu
        35                  40                  45

Leu Asp Lys Asp Lys Ser Asp Val Lys Ser Ile Arg Trp Thr Gly Arg
```

```
                50                  55                  60
Ile Ile Pro Ser Lys Asp Gly Glu Tyr Thr Leu Ser Thr Asp Arg Asp
 65                  70                  75                  80

Asp Val Leu Met Gln Val Asn Thr Glu Ser Thr Ile Ser Asn Thr Leu
                 85                  90                  95

Lys Val Asn Met Lys Lys Gly Lys Glu Tyr Lys Val Arg Ile Glu Leu
                100                 105                 110

Gln Asp Lys Asn Leu Gly Ser Ile Asp Asn Leu Ser Ser Pro Asn Leu
                115                 120                 125

Tyr Trp Glu Leu Asp Gly Met Lys Lys Ile Ile Pro Glu Glu Asn Leu
            130                 135                 140

Phe Leu Arg Asp Tyr Ser Asn Ile Glu Lys Asp Asp Pro Phe Ile Pro
145                 150                 155                 160

Asn Asn Asn Phe Phe Asp Pro Lys Leu Met Ser Asp Trp Glu Asp Glu
                165                 170                 175

Asp Leu Asp Thr Asp Asn Asp Asn Ile Pro Asp Ser Tyr Glu Arg Asn
                180                 185                 190

Gly Tyr Thr Ile Lys Asp Leu Ile Ala Val Lys Trp Glu Asp Ser Phe
            195                 200                 205

Ala Glu Gln Gly Tyr Lys Lys Tyr Val Ser Asn Tyr Leu Glu Ser Asn
210                 215                 220

Thr Ala Gly Asp Pro Tyr Thr Asp Tyr Glu Lys Ala Ser Gly Ser Phe
225                 230                 235                 240

Asp Lys Ala Ile Lys Thr Glu Ala Arg Asp Pro Leu Val Ala Ala Tyr
                245                 250                 255

Pro Ile Val Gly Val Gly Met Glu Lys Leu Ile Ile Ser Thr Asn Glu
            260                 265                 270

His Ala Ser Thr Asp Gln Gly Lys Thr Val Ser Arg Ala Thr Thr Asn
            275                 280                 285

Ser Lys Thr Glu Ser Asn Thr Ala Gly Val Ser Val Asn Val Gly Tyr
            290                 295                 300

Gln Asn Gly Phe Thr Ala Asn Val Thr Thr Asn Tyr Ser His Thr Thr
305                 310                 315                 320

Asp Asn Ser Thr Ala Val Gln Asp Ser Asn Gly Glu Ser Trp Asn Thr
                325                 330                 335

Gly Leu Ser Ile Asn Lys Gly Glu Ser Ala Tyr Ile Asn Ala Asn Val
            340                 345                 350

Arg Tyr Tyr Asn Thr Gly Thr Ala Pro Met Tyr Lys Val Thr Pro Thr
            355                 360                 365

Thr Asn Leu Val Leu Asp Gly Asp Thr Leu Ser Thr Ile Lys Ala Gln
    370                 375                 380

Glu Asn Gln Ile Gly Asn Leu Ser Pro Gly Asp Thr Tyr Pro Lys
385                 390                 395                 400

Lys Gly Leu Ser Pro Leu Ala Leu Asn Thr Met Asp Gln Phe Ser Ser
                405                 410                 415

Arg Leu Ile Pro Ile Asn Tyr Asp Gln Leu Lys Lys Leu Asp Ala Gly
            420                 425                 430

Lys Gln Ile Lys Leu Glu Thr Thr Gln Val Ser Gly Asn Phe Gly Thr
            435                 440                 445

Lys Asn Ser Ser Gly Gln Ile Val Thr Glu Gly Asn Ser Trp Ser Asp
    450                 455                 460

Tyr Ile Ser Gln Ile Asp Ser Ile Ser Ala Ser Ile Ile Leu Asp Thr
465                 470                 475                 480
```

```
Glu Asn Glu Ser Tyr Glu Arg Val Thr Ala Lys Asn Leu Gln Asp
            485                 490                 495

Pro Glu Asp Lys Thr Pro Glu Leu Thr Ile Gly Glu Ala Ile Glu Lys
            500                 505                 510

Ala Phe Gly Ala Thr Lys Lys Asp Gly Leu Leu Tyr Phe Asn Asp Ile
            515                 520                 525

Pro Ile Asp Glu Ser Cys Val Glu Leu Ile Phe Asp Asp Asn Thr Ala
            530                 535                 540

Asn Lys Ile Lys Asp Ser Leu Lys Thr Leu Ser Asp Lys Lys Ile Tyr
545                 550                 555                 560

Asn Val Lys Leu Glu Arg Gly Met Asn Ile Leu Ile Lys Thr Pro Thr
            565                 570                 575

Tyr Phe Thr Asn Phe Asp Asp Tyr Asn Asn Tyr Xaa Ser Thr Trp Ser
            580                 585                 590

Asn Val Asn Thr Thr Asn Gln Asp Gly Leu Gln Gly Ser Ala Asn Lys
            595                 600                 605

Leu Asn Gly Glu Thr Lys Ile Lys Ile Pro Met Ser Glu Leu Lys Pro
610                 615                 620

Tyr Lys Arg Tyr Val Phe Ser Gly Tyr Ser Lys Asp Pro Leu Thr Ser
625                 630                 635                 640

Asn Ser Ile Ile Val Lys Ile Lys Ala Lys Glu Glu Lys Thr Asp Tyr
            645                 650                 655

Leu Val Pro Glu Gln Gly Tyr Thr Lys Phe Ser Tyr Glu Phe Glu Thr
            660                 665                 670

Thr Glu Lys Asp Ser Ser Asn Ile Glu Ile Thr Leu Ile Gly Ser Gly
            675                 680                 685

Thr Thr Tyr Leu Asp Asn Leu Ser Ile Thr Glu Leu Asn Ser Thr Pro
            690                 695                 700

Glu Ile Leu Asp Glu Pro Glu Val Lys Ile Pro Thr Asp Gln Glu Ile
705                 710                 715                 720

Met Asp Ala His Lys Ile Tyr Phe Ala Asp Leu Asn Phe Asn Pro Ser
            725                 730                 735

Thr Gly Asn Thr Tyr Ile Asn Gly Met Tyr Phe Ala Pro Thr Gln Thr
            740                 745                 750

Asn Lys Glu Ala Leu Asp Tyr Ile Gln Lys Tyr Arg Val Glu Ala Thr
            755                 760                 765

Leu Gln Tyr Ser Gly Phe Lys Asp Ile Gly Thr Lys Asp Lys Glu Met
            770                 775                 780

Arg Asn Tyr Leu Gly Asp Pro Asn Gln Pro Lys Thr Asn Tyr Val Asn
785                 790                 795                 800

Leu Arg Ser Tyr Phe Thr Gly Gly Glu Asn Ile Met Thr Tyr Lys Lys
            805                 810                 815

Leu Arg Ile Tyr Ala Ile Thr Pro Asp Asp Arg Glu Leu Leu Val Leu
            820                 825                 830

Ser Val Asp Ala Ser Met Gln Glu Ile Arg Asn Asn Ser Asn Ser Ser
            835                 840                 845

Asp Ile Glu Leu Glu Glu Lys Val Met Leu Thr Glu Cys Glu Ile Asn
            850                 855                 860

Val Ile Ser Asn Ile Asp Thr Gln Ile Val Glu Glu Arg Ile Glu Glu
865                 870                 875                 880

Ala Lys Asn Leu Thr Ser Asp Ser Ile Asn Tyr Ile Lys Asp Glu Phe
            885                 890                 895
```

-continued

Lys Leu Ile Glu Ser Ile Ser Asp Ala Leu Cys Asp Leu Lys Gln Gln
                900                 905                 910

Asn Glu Leu Glu Asp Ser His Phe Ile Ser Phe Glu Asp Ile Ser Glu
        915                 920                 925

Thr Asp Glu Gly Phe Ser Ile Arg Phe Ile Asn Lys Glu Thr Gly Glu
    930                 935                 940

Ser Ile Phe Val Glu Thr Glu Lys Thr Ile Phe Ser Glu Tyr Ala Asn
945                 950                 955                 960

His Ile Thr Glu Glu Ile Ser Lys Ile Lys Gly Thr Ile Phe Asp Thr
                965                 970                 975

Val Asn Gly Lys Leu Val Lys Lys Val Asn Leu Asp Thr Thr His Glu
            980                 985                 990

Val Asn Thr Leu Asn Ala Ala Phe Phe Ile Gln Ser Leu Ile Glu Tyr
        995                 1000                1005

Asn Ser Ser Lys Glu Ser Leu Ser Asn Leu Ser Val Ala Met Lys
    1010                1015                1020

Val Gln Val Tyr Ala Gln Leu Phe Ser Thr Gly Leu Asn Thr Ile
    1025                1030                1035

Thr Asp Ala Ala Lys Val Val Glu Leu Val Ser Thr Ala Leu Asp
    1040                1045                1050

Glu Thr Ile Asp Leu Leu Pro Thr Leu Ser Glu Gly Leu Pro Ile
    1055                1060                1065

Ile Ala Thr Ile Ile Asp Gly Val Ser Leu Gly Ala Ala Ile Lys
    1070                1075                1080

Glu Leu Ser Glu Thr Ser Asp Pro Leu Leu Arg Gln Glu Ile Glu
    1085                1090                1095

Ala Lys Ile Gly Ile Met Ala Val Asn Leu Thr Thr Ala Thr Thr
    1100                1105                1110

Ala Ile Ile Thr Ser Ser Leu Gly Ile Ala Ser Gly Phe Ser Ile
    1115                1120                1125

Leu Leu Val Pro Leu Ala Gly Ile Ser Ala Gly Ile Pro Ser Leu
    1130                1135                1140

Val Asn Asn Glu Leu Val Leu Arg Asp Lys Ala Thr Lys Val Val
    1145                1150                1155

Asp Tyr Phe Lys His Val Ser Leu Val Glu Thr Glu Gly Val Phe
    1160                1165                1170

Thr Leu Leu Asp Asp Lys Ile Met Met Pro Gln Asp Asp Leu Val
    1175                1180                1185

Ile Ser Glu Ile Asp Phe Asn Asn Asn Ser Ile Val Leu Gly Lys
    1190                1195                1200

Cys Glu Ile Trp Arg Met Glu Gly Gly Ser Gly His Thr Val Thr
    1205                1210                1215

Asp Asp Ile Asp His Phe Phe Ser Ala Pro Ser Ile Thr Tyr Arg
    1220                1225                1230

Glu Pro His Leu Ser Ile Tyr Asp Val Leu Glu Val Gln Lys Glu
    1235                1240                1245

Glu Leu Asp Leu Ser Lys Asp Leu Met Val Leu Pro Asn Ala Pro
    1250                1255                1260

Asn Arg Val Phe Ala Trp Glu Thr Gly Trp Thr Pro Gly Leu Arg
    1265                1270                1275

Ser Leu Glu Asn Asp Gly Thr Lys Leu Leu Asp Arg Ile Arg Asp
    1280                1285                1290

Asn Tyr Glu Gly Glu Phe Tyr Trp Arg Tyr Phe Ala Phe Ile Ala

```
            1295                1300                1305

Asp Ala Leu Ile Thr Thr Leu Lys Pro Arg Tyr Glu Asp Thr Asn
        1310                1315                1320

Ile Arg Ile Asn Leu Asp Ser Asn Thr Arg Ser Phe Ile Val Pro
    1325                1330                1335

Ile Ile Thr Thr Glu Tyr Ile Arg Glu Lys Leu Ser Tyr Ser Phe
    1340                1345                1350

Tyr Gly Ser Gly Gly Thr Tyr Ala Leu Ser Leu Ser Gln Tyr Asn
    1355                1360                1365

Met Gly Ile Asn Ile Glu Leu Ser Glu Ser Asp Val Trp Ile Ile
    1370                1375                1380

Asp Val Asp Asn Val Val Arg Asp Val Thr Ile Glu Ser Asp Lys
    1385                1390                1395

Ile Lys Lys Gly Asp Leu Ile Glu Gly Ile Leu Ser Thr Leu Ser
    1400                1405                1410

Ile Glu Glu Asn Lys Ile Ile Leu Asn Ser His Glu Ile Asn Phe
    1415                1420                1425

Ser Gly Glu Val Asn Gly Ser Asn Gly Phe Val Ser Leu Thr Phe
    1430                1435                1440

Ser Ile Leu Glu Gly Ile Asn Ala Ile Glu Val Asp Leu Leu
    1445                1450                1455

Ser Lys Ser Tyr Lys Leu Leu Ile Ser Gly Glu Leu Lys Ile Leu
    1460                1465                1470

Met Leu Asn Ser Asn His Ile Gln Gln Lys Ile Asp Tyr Ile Gly
    1475                1480                1485

Phe Asn Ser Glu Leu Gln Lys Asn Ile Pro Tyr Ser Phe Val Asp
    1490                1495                1500

Ser Glu Gly Lys Glu Asn Gly Phe Ile Asn Gly Ser Thr Lys Glu
    1505                1510                1515

Gly Leu Phe Val Ser Glu Leu Pro Asp Val Val Leu Ile Ser Lys
    1520                1525                1530

Val Tyr Met Asp Asp Ser Lys Pro Ser Phe Gly Tyr Tyr Ser Asn
    1535                1540                1545

Asn Leu Lys Asp Val Lys Val Ile Thr Lys Asp Asn Val Asn Ile
    1550                1555                1560

Leu Thr Gly Tyr Tyr Leu Lys Asp Asp Ile Lys Ile Ser Leu Ser
    1565                1570                1575

Leu Thr Leu Gln Asp Glu Lys Thr Ile Lys Leu Asn Ser Val His
    1580                1585                1590

Leu Asp Glu Ser Gly Val Ala Glu Ile Leu Lys Phe Met Asn Arg
    1595                1600                1605

Lys Gly Asn Thr Asn Thr Ser Asp Ser Leu Met Ser Phe Leu Glu
    1610                1615                1620

Ser Met Asn Ile Lys Ser Ile Phe Val Asn Phe Leu Gln Ser Asn
    1625                1630                1635

Ile Lys Phe Ile Leu Asp Ala Asn Phe Ile Ile Ser Gly Thr Thr
    1640                1645                1650

Ser Ile Gly Gln Phe Glu Phe Ile Cys Asp Glu Asn Asp Asn Ile
    1655                1660                1665

Gln Pro Tyr Phe Ile Lys Phe Asn Thr Leu Glu Thr Asn Tyr Thr
    1670                1675                1680

Leu Tyr Val Gly Asn Arg Gln Asn Met Ile Val Glu Pro Asn Tyr
    1685                1690                1695
```

```
Asp Leu Asp Asp Ser Gly Asp Ile Ser Ser Thr Val Ile Asn Phe
    1700                1705                1710

Ser Gln Lys Tyr Leu Tyr Gly Ile Asp Ser Cys Val Asn Lys Val
    1715                1720                1725

Val Ile Ser Pro Asn Ile Tyr Thr Asp Glu Ile Asn Ile Thr Pro
    1730                1735                1740

Val Tyr Glu Thr Asn Asn Thr Tyr Pro Glu Val Ile Val Leu Asp
    1745                1750                1755

Ala Asn Tyr Ile Asn Glu Lys Ile Asn Val Asn Ile Asn Asp Leu
    1760                1765                1770

Ser Ile Arg Tyr Val Trp Ser Asn Asp Gly Asn Asp Phe Ile Leu
    1775                1780                1785

Met Ser Thr Ser Glu Glu Asn Lys Val Ser Gln Val Lys Ile Arg
    1790                1795                1800

Phe Val Asn Val Phe Lys Asp Lys Thr Leu Ala Asn Lys Leu Ser
    1805                1810                1815

Phe Asn Phe Ser Asp Lys Gln Asp Val Pro Val Ser Glu Ile Ile
    1820                1825                1830

Leu Ser Phe Thr Pro Ser Tyr Tyr Glu Asp Gly Leu Ile Gly Tyr
    1835                1840                1845

Asp Leu Gly Leu Val Ser Leu Tyr Asn Glu Lys Phe Tyr Ile Asn
    1850                1855                1860

Asn Phe Gly Met Ser Arg Met Val Thr Gly Val Phe Lys Gly Pro
    1865                1870                1875

Asn Gly Phe Glu Tyr Phe Ala Pro Ala Asn Thr His Asn Asn Asn
    1880                1885                1890

Ile Glu Gly Gln Ala Ile Val Tyr Gln Asn Lys Phe Leu Thr Leu
    1895                1900                1905

Asn Gly Lys Lys Tyr Tyr Phe Asp Asn Asp Ser Lys Ala Val Thr
    1910                1915                1920

Gly Trp Gln Thr Ile Asp Gly Lys Lys Tyr Tyr Phe Asn Leu Asn
    1925                1930                1935

Thr Ala Glu Ala Ala Thr Gly Trp Gln Thr Ile Asp Gly Lys Lys
    1940                1945                1950

Tyr Tyr Phe Asn Leu Asn Thr Ala Glu Ala Ala Thr Gly Trp Gln
    1955                1960                1965

Thr Ile Asp Gly Lys Lys Tyr Tyr Phe Asn Thr Asn Thr Phe Ile
    1970                1975                1980

Ala Ser Thr Gly Tyr Thr Ser Ile Asn Gly Lys His Phe Tyr Phe
    1985                1990                1995

Asn Thr Asp Gly Ile Met Gln Ile Gly Val Phe Lys Gly Pro Asn
    2000                2005                2010

Gly Phe Glu Tyr Phe Ala Pro Ala Asn Thr Asp Ala Asn Asn Ile
    2015                2020                2025

Glu Gly Gln Ala Ile Leu Tyr Gln Asn Lys Phe Leu Thr Leu Asn
    2030                2035                2040

Gly Lys Lys Tyr Tyr Phe Gly Ser Asp Ser Lys Ala Val Thr Gly
    2045                2050                2055

Leu Arg Thr Ile Asp Gly Lys Lys Tyr Tyr Phe Asn Thr Asn Thr
    2060                2065                2070

Ala Val Ala Val Thr Gly Trp Gln Thr Ile Asn Gly Lys Lys Tyr
    2075                2080                2085
```

```
Tyr Phe Asn Thr Asn Thr Ser Ile Ala Ser Thr Gly Tyr Thr Ile
    2090                2095                2100

Ile Ser Gly Lys His Phe Tyr Phe Asn Thr Asp Gly Ile Met Gln
    2105                2110                2115

Ile Gly Val Phe Lys Gly Pro Asp Gly Phe Glu Tyr Phe Ala Pro
    2120                2125                2130

Ala Asn Thr Asp Ala Asn Asn Ile Glu Gly Gln Ala Ile Arg Tyr
    2135                2140                2145

Gln Asn Arg Phe Leu Tyr Leu His Asp Asn Ile Tyr Tyr Phe Gly
    2150                2155                2160

Asn Asn Ser Lys Ala Ala Thr Gly Trp Val Thr Ile Asp Gly Asn
    2165                2170                2175

Arg Tyr Tyr Phe Glu Pro Asn Thr Ala Met Gly Ala Asn Gly Tyr
    2180                2185                2190

Lys Thr Ile Asp Asn Lys Asn Phe Tyr Phe Arg Asn Gly Leu Pro
    2195                2200                2205

Gln Ile Gly Val Phe Lys Gly Ser Asn Gly Phe Glu Tyr Phe Ala
    2210                2215                2220

Pro Ala Asn Thr Asp Ala Asn Asn Ile Glu Gly Gln Ala Ile Arg
    2225                2230                2235

Tyr Gln Asn Arg Phe Leu His Leu Leu Gly Lys Ile Tyr Tyr Phe
    2240                2245                2250

Gly Asn Asn Ser Lys Ala Val Thr Gly Trp Gln Thr Ile Asn Gly
    2255                2260                2265

Lys Val Tyr Tyr Phe Met Pro Asp Thr Ala Met Ala Ala Ala Gly
    2270                2275                2280

Gly Leu Phe Glu Ile Asp Gly Val Ile Tyr Phe Phe Gly Val Asp
    2285                2290                2295

Gly Val Lys Ala Pro Gly Ile Tyr Gly
    2300                2305

<210> SEQ ID NO 18
<211> LENGTH: 835
<212> TYPE: PRT
<213> ORGANISM: Clostridium difficile
<220> FEATURE:
<221> NAME/KEY: SITE
<222> LOCATION: (588)..(588)
<223> OTHER INFORMATION: Xaa can be any naturally occurring amino acid

<400> SEQUENCE: 18

Met Glu Ile Val Asn Glu Asp Ile Leu Pro Asn Asn Gly Leu Met Gly
1               5                   10                  15

Tyr Tyr Phe Thr Asp Glu His Phe Lys Asp Leu Lys Leu Met Ala Pro
            20                  25                  30

Ile Lys Asp Gly Asn Leu Lys Phe Glu Glu Lys Lys Val Asp Lys Leu
        35                  40                  45

Leu Asp Lys Asp Lys Ser Asp Val Lys Ser Ile Arg Trp Thr Gly Arg
    50                  55                  60

Ile Ile Pro Ser Lys Asp Gly Glu Tyr Thr Leu Ser Thr Asp Arg Asp
65                  70                  75                  80

Asp Val Leu Met Gln Val Asn Thr Glu Ser Thr Ile Ser Asn Thr Leu
                85                  90                  95

Lys Val Asn Met Lys Lys Gly Lys Glu Tyr Lys Val Arg Ile Glu Leu
            100                 105                 110

Gln Asp Lys Asn Leu Gly Ser Ile Asp Asn Leu Ser Ser Pro Asn Leu
```

-continued

```
            115                 120                 125
Tyr Trp Glu Leu Asp Gly Met Lys Lys Ile Ile Pro Glu Glu Asn Leu
        130                 135                 140

Phe Leu Arg Asp Tyr Ser Asn Ile Glu Lys Asp Asp Pro Phe Ile Pro
145                 150                 155                 160

Asn Asn Asn Phe Phe Asp Pro Lys Leu Met Ser Asp Trp Glu Asp Glu
                165                 170                 175

Asp Leu Asp Thr Asp Asn Asp Ile Pro Asp Ser Tyr Glu Arg Asn
            180                 185                 190

Gly Tyr Thr Ile Lys Asp Leu Ile Ala Val Lys Trp Glu Asp Ser Phe
        195                 200                 205

Ala Glu Gln Gly Tyr Lys Lys Tyr Val Ser Asn Tyr Leu Glu Ser Asn
        210                 215                 220

Thr Ala Gly Asp Pro Tyr Thr Asp Tyr Glu Lys Ala Ser Gly Ser Phe
225                 230                 235                 240

Asp Lys Ala Ile Lys Thr Glu Ala Arg Asp Pro Leu Val Ala Ala Tyr
                245                 250                 255

Pro Ile Val Gly Val Gly Met Glu Lys Leu Ile Ile Ser Thr Asn Glu
                260                 265                 270

His Ala Ser Thr Asp Gln Gly Lys Thr Val Ser Arg Ala Thr Thr Asn
            275                 280                 285

Ser Lys Thr Glu Ser Asn Thr Ala Gly Val Ser Val Asn Val Gly Tyr
        290                 295                 300

Gln Asn Gly Phe Thr Ala Asn Val Thr Asn Tyr Ser His Thr Thr
305                 310                 315                 320

Asp Asn Ser Thr Ala Val Gln Asp Ser Asn Gly Glu Ser Trp Asn Thr
                325                 330                 335

Gly Leu Ser Ile Asn Lys Gly Glu Ser Ala Tyr Ile Asn Ala Asn Val
            340                 345                 350

Arg Tyr Tyr Asn Thr Gly Thr Ala Pro Met Tyr Lys Val Thr Pro Thr
        355                 360                 365

Thr Asn Leu Val Leu Asp Gly Asp Thr Leu Ser Thr Ile Lys Ala Gln
        370                 375                 380

Glu Asn Gln Ile Gly Asn Asn Leu Ser Pro Gly Asp Thr Tyr Pro Lys
385                 390                 395                 400

Lys Gly Leu Ser Pro Leu Ala Leu Asn Thr Met Asp Gln Phe Ser Ser
                405                 410                 415

Arg Leu Ile Pro Ile Asn Tyr Asp Gln Leu Lys Lys Leu Asp Ala Gly
                420                 425                 430

Lys Gln Ile Lys Leu Glu Thr Thr Gln Val Ser Gly Asn Phe Gly Thr
        435                 440                 445

Lys Asn Ser Ser Gly Gln Ile Val Thr Glu Gly Asn Ser Trp Ser Asp
        450                 455                 460

Tyr Ile Ser Gln Ile Asp Ser Ile Ser Ala Ser Ile Ile Leu Asp Thr
465                 470                 475                 480

Glu Asn Glu Ser Tyr Glu Arg Arg Val Thr Ala Lys Asn Leu Gln Asp
                485                 490                 495

Pro Glu Asp Lys Thr Pro Glu Leu Thr Ile Gly Glu Ala Ile Glu Lys
            500                 505                 510

Ala Phe Gly Ala Thr Lys Lys Asp Gly Leu Leu Tyr Phe Asn Asp Ile
        515                 520                 525

Pro Ile Asp Glu Ser Cys Val Glu Leu Ile Phe Asp Asp Asn Thr Ala
        530                 535                 540
```

```
Asn Lys Ile Lys Asp Ser Leu Lys Thr Leu Ser Asp Lys Lys Ile Tyr
545                 550                 555                 560

Asn Val Lys Leu Glu Arg Gly Met Asn Ile Leu Ile Lys Thr Pro Thr
                565                 570                 575

Tyr Phe Thr Asn Phe Asp Asp Tyr Asn Asn Tyr Xaa Ser Thr Trp Ser
            580                 585                 590

Asn Val Asn Thr Thr Asn Gln Asp Gly Leu Gln Gly Ser Ala Asn Lys
        595                 600                 605

Leu Asn Gly Glu Thr Lys Ile Lys Ile Pro Met Ser Glu Leu Lys Pro
    610                 615                 620

Tyr Lys Arg Tyr Val Phe Ser Gly Tyr Ser Lys Asp Pro Leu Thr Ser
625                 630                 635                 640

Asn Ser Ile Ile Val Lys Ile Lys Ala Lys Glu Glu Lys Thr Asp Tyr
                645                 650                 655

Leu Val Pro Glu Gln Gly Tyr Thr Lys Phe Ser Tyr Glu Phe Glu Thr
            660                 665                 670

Thr Glu Lys Asp Ser Ser Asn Ile Glu Ile Thr Leu Ile Gly Ser Gly
        675                 680                 685

Thr Thr Tyr Leu Asp Asn Leu Ser Ile Thr Glu Leu Asn Ser Thr Pro
    690                 695                 700

Glu Ile Leu Asp Glu Pro Glu Val Lys Ile Pro Thr Asp Gln Glu Ile
705                 710                 715                 720

Met Asp Ala His Lys Ile Tyr Phe Ala Asp Leu Asn Phe Asn Pro Ser
                725                 730                 735

Thr Gly Asn Thr Tyr Ile Asn Gly Met Tyr Phe Ala Pro Thr Gln Thr
            740                 745                 750

Asn Lys Glu Ala Leu Asp Tyr Ile Gln Lys Tyr Arg Val Glu Ala Thr
        755                 760                 765

Leu Gln Tyr Ser Gly Phe Lys Asp Ile Gly Thr Lys Asp Lys Glu Met
    770                 775                 780

Arg Asn Tyr Leu Gly Asp Pro Asn Gln Pro Lys Thr Asn Tyr Val Asn
785                 790                 795                 800

Leu Arg Ser Tyr Phe Thr Gly Gly Glu Asn Ile Met Thr Tyr Lys Lys
                805                 810                 815

Leu Arg Ile Tyr Ala Ile Thr Pro Asp Asp Arg Glu Leu Leu Val Leu
            820                 825                 830

Ser Val Asp
        835

<210> SEQ ID NO 19
<211> LENGTH: 1030
<212> TYPE: PRT
<213> ORGANISM: Clostridium difficile

<400> SEQUENCE: 19

Met Gln Glu Ile Arg Asn Asn Ser Asn Ser Ser Asp Ile Glu Leu Glu
1               5                   10                  15

Glu Lys Val Met Leu Thr Glu Cys Glu Ile Asn Val Ile Ser Asn Ile
            20                  25                  30

Asp Thr Gln Ile Val Glu Glu Arg Ile Glu Glu Ala Lys Asn Leu Thr
        35                  40                  45

Ser Asp Ser Ile Asn Tyr Ile Lys Asp Glu Phe Lys Leu Ile Glu Ser
    50                  55                  60

Ile Ser Asp Ala Leu Cys Asp Leu Lys Gln Gln Asn Glu Leu Glu Asp
```

```
                65                  70                  75                  80
        Ser His Phe Ile Ser Phe Glu Asp Ile Ser Glu Thr Asp Gly Phe
                        85                  90                  95

Ser Ile Arg Phe Ile Asn Lys Glu Thr Gly Glu Ser Ile Phe Val Glu
                        100                 105                 110

Thr Glu Lys Thr Ile Phe Ser Glu Tyr Ala Asn His Ile Thr Glu Glu
                        115                 120                 125

Ile Ser Lys Ile Lys Gly Thr Ile Phe Asp Thr Val Asn Gly Lys Leu
                        130                 135                 140

Val Lys Lys Val Asn Leu Asp Thr Thr His Glu Val Asn Thr Leu Asn
        145                 150                 155                 160

Ala Ala Phe Phe Ile Gln Ser Leu Ile Glu Tyr Asn Ser Ser Lys Glu
                        165                 170                 175

Ser Leu Ser Asn Leu Ser Val Ala Met Lys Val Gln Val Tyr Ala Gln
                        180                 185                 190

Leu Phe Ser Thr Gly Leu Asn Thr Ile Thr Asp Ala Ala Lys Val Val
                        195                 200                 205

Glu Leu Val Ser Thr Ala Leu Asp Glu Thr Ile Asp Leu Leu Pro Thr
        210                 215                 220

Leu Ser Glu Gly Leu Pro Ile Ile Ala Thr Ile Ile Asp Gly Val Ser
        225                 230                 235                 240

Leu Gly Ala Ala Ile Lys Glu Leu Ser Glu Thr Ser Asp Pro Leu Leu
                        245                 250                 255

Arg Gln Glu Ile Glu Ala Lys Ile Gly Ile Met Ala Val Asn Leu Thr
                        260                 265                 270

Thr Ala Thr Thr Ala Ile Ile Thr Ser Ser Leu Gly Ile Ala Ser Gly
                        275                 280                 285

Phe Ser Ile Leu Leu Val Pro Leu Ala Gly Ile Ser Ala Gly Ile Pro
                        290                 295                 300

Ser Leu Val Asn Asn Glu Leu Val Leu Arg Asp Lys Ala Thr Lys Val
        305                 310                 315                 320

Val Asp Tyr Phe Lys His Val Ser Leu Val Glu Thr Glu Gly Val Phe
                        325                 330                 335

Thr Leu Leu Asp Asp Lys Ile Met Met Pro Gln Asp Asp Leu Val Ile
                        340                 345                 350

Ser Glu Ile Asp Phe Asn Asn Asn Ser Ile Val Leu Gly Lys Cys Glu
                        355                 360                 365

Ile Trp Arg Met Glu Gly Gly Ser Gly His Thr Val Thr Asp Asp Ile
                        370                 375                 380

Asp His Phe Phe Ser Ala Pro Ser Ile Thr Tyr Arg Glu Pro His Leu
        385                 390                 395                 400

Ser Ile Tyr Asp Val Leu Glu Val Gln Lys Glu Glu Leu Asp Leu Ser
                        405                 410                 415

Lys Asp Leu Met Val Leu Pro Asn Ala Pro Asn Arg Val Phe Ala Trp
                        420                 425                 430

Glu Thr Gly Trp Thr Pro Gly Leu Arg Ser Leu Glu Asn Asp Gly Thr
                        435                 440                 445

Lys Leu Leu Asp Arg Ile Arg Asp Asn Tyr Glu Gly Glu Phe Tyr Trp
                        450                 455                 460

Arg Tyr Phe Ala Phe Ile Ala Asp Ala Leu Ile Thr Thr Leu Lys Pro
        465                 470                 475                 480

Arg Tyr Glu Asp Thr Asn Ile Arg Ile Asn Leu Asp Ser Asn Thr Arg
                        485                 490                 495
```

```
Ser Phe Ile Val Pro Ile Ile Thr Thr Glu Tyr Ile Arg Glu Lys Leu
            500                 505                 510

Ser Tyr Ser Phe Tyr Gly Ser Gly Thr Tyr Ala Leu Ser Leu Ser
            515                 520                 525

Gln Tyr Asn Met Gly Ile Asn Ile Glu Leu Ser Glu Ser Asp Val Trp
            530                 535                 540

Ile Ile Asp Val Asp Asn Val Val Arg Asp Val Thr Ile Glu Ser Asp
545                 550                 555                 560

Lys Ile Lys Lys Gly Asp Leu Ile Glu Gly Ile Leu Ser Thr Leu Ser
                565                 570                 575

Ile Glu Glu Asn Lys Ile Ile Leu Asn Ser His Glu Ile Asn Phe Ser
            580                 585                 590

Gly Glu Val Asn Gly Ser Asn Gly Phe Val Ser Leu Thr Phe Ser Ile
            595                 600                 605

Leu Glu Gly Ile Asn Ala Ile Ile Glu Val Asp Leu Leu Ser Lys Ser
            610                 615                 620

Tyr Lys Leu Leu Ile Ser Gly Glu Leu Lys Ile Leu Met Leu Asn Ser
625                 630                 635                 640

Asn His Ile Gln Gln Lys Ile Asp Tyr Ile Gly Phe Asn Ser Glu Leu
                645                 650                 655

Gln Lys Asn Ile Pro Tyr Ser Phe Val Asp Ser Glu Gly Lys Glu Asn
            660                 665                 670

Gly Phe Ile Asn Gly Ser Thr Lys Glu Gly Leu Phe Val Ser Glu Leu
            675                 680                 685

Pro Asp Val Val Leu Ile Ser Lys Val Tyr Met Asp Asp Ser Lys Pro
690                 695                 700

Ser Phe Gly Tyr Tyr Ser Asn Asn Leu Lys Asp Val Lys Val Ile Thr
705                 710                 715                 720

Lys Asp Asn Val Asn Ile Leu Thr Gly Tyr Tyr Leu Lys Asp Asp Ile
                725                 730                 735

Lys Ile Ser Leu Ser Leu Thr Leu Gln Asp Glu Lys Thr Ile Lys Leu
            740                 745                 750

Asn Ser Val His Leu Asp Glu Ser Gly Val Ala Glu Ile Leu Lys Phe
            755                 760                 765

Met Asn Arg Lys Gly Asn Thr Asn Thr Ser Asp Ser Leu Met Ser Phe
770                 775                 780

Leu Glu Ser Met Asn Ile Lys Ser Ile Phe Val Asn Phe Leu Gln Ser
785                 790                 795                 800

Asn Ile Lys Phe Ile Leu Asp Ala Asn Phe Ile Ile Ser Gly Thr Thr
                805                 810                 815

Ser Ile Gly Gln Phe Glu Phe Ile Cys Asp Glu Asn Asp Asn Ile Gln
            820                 825                 830

Pro Tyr Phe Ile Lys Phe Asn Thr Leu Glu Thr Asn Tyr Thr Leu Tyr
            835                 840                 845

Val Gly Asn Arg Gln Asn Met Ile Val Glu Pro Asn Tyr Asp Leu Asp
            850                 855                 860

Asp Ser Gly Asp Ile Ser Ser Thr Val Ile Asn Phe Ser Gln Lys Tyr
865                 870                 875                 880

Leu Tyr Gly Ile Asp Ser Cys Val Asn Lys Val Val Ile Ser Pro Asn
                885                 890                 895

Ile Tyr Thr Asp Glu Ile Asn Ile Thr Pro Val Tyr Glu Thr Asn Asn
            900                 905                 910
```

```
Thr Tyr Pro Glu Val Ile Val Leu Asp Ala Asn Tyr Ile Asn Glu Lys
            915                 920                 925

Ile Asn Val Asn Ile Asn Asp Leu Ser Ile Arg Tyr Val Trp Ser Asn
        930                 935                 940

Asp Gly Asn Asp Phe Ile Leu Met Ser Thr Ser Glu Glu Asn Lys Val
945                 950                 955                 960

Ser Gln Val Lys Ile Arg Phe Val Asn Val Phe Lys Asp Lys Thr Leu
            965                 970                 975

Ala Asn Lys Leu Ser Phe Asn Phe Ser Asp Lys Gln Asp Val Pro Val
        980                 985                 990

Ser Glu Ile Ile Leu Ser Phe Thr Pro Ser Tyr Tyr Glu Asp Gly Leu
            995                 1000                1005

Ile Gly Tyr Asp Leu Gly Leu Val Ser Leu Tyr Asn Glu Lys Phe
    1010                1015                1020

Tyr Ile Asn Asn Phe Gly Met
    1025                1030

<210> SEQ ID NO 20
<211> LENGTH: 438
<212> TYPE: PRT
<213> ORGANISM: Clostridium difficile

<400> SEQUENCE: 20

Met Val Thr Gly Val Phe Lys Gly Pro Asn Gly Phe Glu Tyr Phe Ala
1               5                   10                  15

Pro Ala Asn Thr His Asn Asn Ile Glu Gly Gln Ala Ile Val Tyr
            20                  25                  30

Gln Asn Lys Phe Leu Thr Leu Asn Gly Lys Lys Tyr Tyr Phe Asp Asn
        35                  40                  45

Asp Ser Lys Ala Val Thr Gly Trp Gln Thr Ile Asp Gly Lys Lys Tyr
50                  55                  60

Tyr Phe Asn Leu Asn Thr Ala Glu Ala Ala Thr Gly Trp Gln Thr Ile
65                  70                  75                  80

Asp Gly Lys Lys Tyr Tyr Phe Asn Leu Asn Thr Ala Glu Ala Ala Thr
            85                  90                  95

Gly Trp Gln Thr Ile Asp Gly Lys Lys Tyr Tyr Phe Asn Thr Asn Thr
            100                 105                 110

Phe Ile Ala Ser Thr Gly Tyr Thr Ser Ile Asn Gly Lys His Phe Tyr
        115                 120                 125

Phe Asn Thr Asp Gly Ile Met Gln Ile Gly Val Phe Lys Gly Pro Asn
130                 135                 140

Gly Phe Glu Tyr Phe Ala Pro Ala Asn Thr Asp Ala Asn Asn Ile Glu
145                 150                 155                 160

Gly Gln Ala Ile Leu Tyr Gln Asn Lys Phe Leu Thr Leu Asn Gly Lys
            165                 170                 175

Lys Tyr Tyr Phe Gly Ser Asp Ser Lys Ala Val Thr Gly Leu Arg Thr
        180                 185                 190

Ile Asp Gly Lys Lys Tyr Tyr Phe Asn Thr Asn Thr Ala Val Ala Val
    195                 200                 205

Thr Gly Trp Gln Thr Ile Asn Gly Lys Lys Tyr Tyr Phe Asn Thr Asn
210                 215                 220

Thr Ser Ile Ala Ser Thr Gly Tyr Thr Ile Ile Ser Gly Lys His Phe
225                 230                 235                 240

Tyr Phe Asn Thr Asp Gly Ile Met Gln Ile Gly Val Phe Lys Gly Pro
            245                 250                 255
```

-continued

Asp Gly Phe Glu Tyr Phe Ala Pro Ala Asn Thr Asp Ala Asn Asn Ile
            260                 265                 270

Glu Gly Gln Ala Ile Arg Tyr Gln Asn Arg Phe Leu Tyr Leu His Asp
        275                 280                 285

Asn Ile Tyr Tyr Phe Gly Asn Asn Ser Lys Ala Ala Thr Gly Trp Val
290                 295                 300

Thr Ile Asp Gly Asn Arg Tyr Tyr Phe Glu Pro Asn Thr Ala Met Gly
305                 310                 315                 320

Ala Asn Gly Tyr Lys Thr Ile Asp Asn Lys Asn Phe Tyr Phe Arg Asn
                325                 330                 335

Gly Leu Pro Gln Ile Gly Val Phe Lys Gly Ser Asn Gly Phe Glu Tyr
            340                 345                 350

Phe Ala Pro Ala Asn Thr Asp Ala Asn Asn Ile Glu Gly Gln Ala Ile
        355                 360                 365

Arg Tyr Gln Asn Arg Phe Leu His Leu Leu Gly Lys Ile Tyr Tyr Phe
    370                 375                 380

Gly Asn Asn Ser Lys Ala Val Thr Gly Trp Gln Thr Ile Asn Gly Lys
385                 390                 395                 400

Val Tyr Tyr Phe Met Pro Asp Thr Ala Met Ala Ala Gly Gly Leu
                405                 410                 415

Phe Glu Ile Asp Gly Val Ile Tyr Phe Phe Gly Val Asp Gly Val Lys
        420                 425                 430

Ala Pro Gly Ile Tyr Gly
            435

<210> SEQ ID NO 21
<211> LENGTH: 2351
<212> TYPE: PRT
<213> ORGANISM: Artificial Sequence
<220> FEATURE:
<223> OTHER INFORMATION: Q-Toxin fusion protein
<220> FEATURE:
<221> NAME/KEY: SITE
<222> LOCATION: (588)..(588)
<223> OTHER INFORMATION: Xaa can be any naturally occurring amino acid

<400> SEQUENCE: 21

Met Glu Ile Val Asn Glu Asp Ile Leu Pro Asn Asn Gly Leu Met Gly
1 5 10 15

Tyr Tyr Phe Thr Asp Glu His Phe Lys Asp Leu Lys Leu Met Ala Pro
20 25 30

Ile Lys Asp Gly Asn Leu Lys Phe Glu Glu Lys Lys Val Asp Lys Leu
35 40 45

Leu Asp Lys Asp Lys Ser Asp Val Lys Ser Ile Arg Trp Thr Gly Arg
50 55 60

Ile Ile Pro Ser Lys Asp Gly Glu Tyr Thr Leu Ser Thr Asp Arg Asp
65 70 75 80

Asp Val Leu Met Gln Val Asn Thr Glu Ser Thr Ile Ser Asn Thr Leu
85 90 95

Lys Val Asn Met Lys Lys Gly Lys Glu Tyr Lys Val Arg Ile Glu Leu
100 105 110

Gln Asp Lys Asn Leu Gly Ser Ile Asp Asn Leu Ser Ser Pro Asn Leu
115 120 125

Tyr Trp Glu Leu Asp Gly Met Lys Lys Ile Ile Pro Glu Glu Asn Leu
130 135 140

Phe Leu Arg Asp Tyr Ser Asn Ile Glu Lys Asp Asp Pro Phe Ile Pro

```
            145                 150                 155                 160
Asn Asn Asn Phe Phe Asp Pro Lys Leu Met Ser Asp Trp Glu Asp Glu
                    165                 170                 175

Asp Leu Asp Thr Asp Asn Asp Asn Ile Pro Asp Ser Tyr Glu Arg Asn
                    180                 185                 190

Gly Tyr Thr Ile Lys Asp Leu Ile Ala Val Lys Trp Glu Asp Ser Phe
                195                 200                 205

Ala Glu Gln Gly Tyr Lys Lys Tyr Val Ser Asn Tyr Leu Glu Ser Asn
    210                 215                 220

Thr Ala Gly Asp Pro Tyr Thr Asp Tyr Glu Lys Ala Ser Gly Ser Phe
225                 230                 235                 240

Asp Lys Ala Ile Lys Thr Glu Ala Arg Asp Pro Leu Val Ala Ala Tyr
                245                 250                 255

Pro Ile Val Gly Val Gly Met Glu Lys Leu Ile Ile Ser Thr Asn Glu
                260                 265                 270

His Ala Ser Thr Asp Gln Gly Lys Thr Val Ser Arg Ala Thr Thr Asn
                275                 280                 285

Ser Lys Thr Glu Ser Asn Thr Ala Gly Val Ser Val Asn Val Gly Tyr
    290                 295                 300

Gln Asn Gly Phe Thr Ala Asn Val Thr Thr Asn Tyr Ser His Thr Thr
305                 310                 315                 320

Asp Asn Ser Thr Ala Val Gln Asp Ser Asn Gly Glu Ser Trp Asn Thr
                325                 330                 335

Gly Leu Ser Ile Asn Lys Gly Glu Ser Ala Tyr Ile Asn Ala Asn Val
                340                 345                 350

Arg Tyr Tyr Asn Thr Gly Thr Ala Pro Met Tyr Lys Val Thr Pro Thr
                355                 360                 365

Thr Asn Leu Val Leu Asp Gly Asp Thr Leu Ser Thr Ile Lys Ala Gln
    370                 375                 380

Glu Asn Gln Ile Gly Asn Asn Leu Ser Pro Gly Asp Thr Tyr Pro Lys
385                 390                 395                 400

Lys Gly Leu Ser Pro Leu Ala Leu Asn Thr Met Asp Gln Phe Ser Ser
                405                 410                 415

Arg Leu Ile Pro Ile Asn Tyr Asp Gln Leu Lys Lys Leu Asp Ala Gly
                420                 425                 430

Lys Gln Ile Lys Leu Glu Thr Thr Gln Val Ser Gly Asn Phe Gly Thr
                435                 440                 445

Lys Asn Ser Ser Gly Gln Ile Val Thr Glu Gly Asn Ser Trp Ser Asp
    450                 455                 460

Tyr Ile Ser Gln Ile Asp Ser Ile Ser Ala Ser Ile Ile Leu Asp Thr
465                 470                 475                 480

Glu Asn Glu Ser Tyr Glu Arg Arg Val Thr Ala Lys Asn Leu Gln Asp
                485                 490                 495

Pro Glu Asp Lys Thr Pro Glu Leu Thr Ile Gly Glu Ala Ile Glu Lys
                500                 505                 510

Ala Phe Gly Ala Thr Lys Lys Asp Gly Leu Leu Tyr Phe Asn Asp Ile
    515                 520                 525

Pro Ile Asp Glu Ser Cys Val Glu Leu Ile Phe Asp Asp Asn Thr Ala
    530                 535                 540

Asn Lys Ile Lys Asp Ser Leu Lys Thr Leu Ser Asp Lys Lys Ile Tyr
545                 550                 555                 560

Asn Val Lys Leu Glu Arg Gly Met Asn Ile Leu Ile Lys Thr Pro Thr
                565                 570                 575
```

```
Tyr Phe Thr Asn Phe Asp Asp Tyr Asn Asn Tyr Xaa Ser Thr Trp Ser
                580                 585                 590

Asn Val Asn Thr Thr Asn Gln Asp Gly Leu Gln Gly Ser Ala Asn Lys
                595                 600                 605

Leu Asn Gly Glu Thr Lys Ile Lys Ile Pro Met Ser Glu Leu Lys Pro
610                 615                 620

Tyr Lys Arg Tyr Val Phe Ser Gly Tyr Ser Lys Asp Pro Leu Thr Ser
625                 630                 635                 640

Asn Ser Ile Ile Val Lys Ile Lys Ala Lys Glu Lys Thr Asp Tyr
                645                 650                 655

Leu Val Pro Glu Gln Gly Tyr Thr Lys Phe Ser Tyr Glu Phe Glu Thr
                660                 665                 670

Thr Glu Lys Asp Ser Ser Asn Ile Glu Ile Thr Leu Ile Gly Ser Gly
                675                 680                 685

Thr Thr Tyr Leu Asp Asn Leu Ser Ile Thr Glu Leu Asn Ser Thr Pro
                690                 695                 700

Glu Ile Leu Asp Glu Pro Glu Val Lys Ile Pro Thr Asp Gln Glu Ile
705                 710                 715                 720

Met Asp Ala His Lys Ile Tyr Phe Ala Asp Leu Asn Phe Asn Pro Ser
                725                 730                 735

Thr Gly Asn Thr Tyr Ile Asn Gly Met Tyr Phe Ala Pro Thr Gln Thr
                740                 745                 750

Asn Lys Glu Ala Leu Asp Tyr Ile Gln Lys Tyr Arg Val Glu Ala Thr
                755                 760                 765

Leu Gln Tyr Ser Gly Phe Lys Asp Ile Gly Thr Lys Asp Lys Glu Met
                770                 775                 780

Arg Asn Tyr Leu Gly Asp Pro Asn Gln Pro Lys Thr Asn Tyr Val Asn
785                 790                 795                 800

Leu Arg Ser Tyr Phe Thr Gly Gly Glu Asn Ile Met Thr Tyr Lys Lys
                805                 810                 815

Leu Arg Ile Tyr Ala Ile Thr Pro Asp Asp Arg Glu Leu Leu Val Leu
                820                 825                 830

Ser Val Asp Ala Ser Met Val Ser Gly Leu Ile Tyr Ile Asn Asp Ser
                835                 840                 845

Leu Tyr Tyr Phe Lys Pro Pro Val Asn Asn Leu Ile Thr Gly Phe Val
                850                 855                 860

Thr Val Gly Asp Asp Lys Tyr Tyr Phe Asn Pro Ile Asn Gly Gly Ala
865                 870                 875                 880

Ala Ser Ile Gly Glu Thr Ile Ile Asp Asp Lys Asn Tyr Tyr Phe Asn
                885                 890                 895

Gln Ser Gly Val Leu Gln Thr Gly Val Phe Ser Thr Glu Asp Gly Phe
                900                 905                 910

Lys Tyr Phe Ala Pro Ala Asn Thr Leu Asp Glu Asn Leu Glu Gly Glu
                915                 920                 925

Ala Ile Asp Phe Thr Gly Lys Leu Ile Ile Asp Glu Asn Ile Tyr Tyr
                930                 935                 940

Phe Asp Asp Asn Tyr Arg Gly Ala Val Glu Trp Lys Glu Leu Asp Gly
945                 950                 955                 960

Glu Met His Tyr Phe Ser Pro Glu Thr Gly Lys Ala Phe Lys Gly Leu
                965                 970                 975

Asn Gln Ile Gly Asp Tyr Lys Tyr Tyr Phe Asn Ser Asp Gly Val Met
                980                 985                 990
```

```
Gln Lys Gly Phe Val Ser Ile Asn Asp Asn Lys His Tyr Phe Asp Asp
            995                 1000                1005

Ser Gly Val Met Lys Val Gly Tyr Thr Glu Ile Asp Gly Lys His
    1010                1015                1020

Phe Tyr Phe Ala Glu Asn Gly Glu Met Gln Ile Gly Val Phe Asn
    1025                1030                1035

Thr Glu Asp Gly Phe Lys Tyr Phe Ala His His Asn Glu Asp Leu
    1040                1045                1050

Gly Asn Glu Glu Gly Glu Ile Ser Tyr Ser Gly Ile Leu Asn
    1055                1060                1065

Phe Asn Asn Lys Ile Tyr Tyr Phe Asp Asp Ser Phe Thr Ala Val
    1070                1075                1080

Val Gly Trp Lys Asp Leu Glu Asp Gly Ser Lys Tyr Tyr Phe Asp
    1085                1090                1095

Glu Asp Thr Ala Glu Ala Tyr Ile Gly Leu Ser Leu Ile Asn Asp
    1100                1105                1110

Gly Gln Tyr Tyr Phe Asn Asp Asp Gly Ile Met Gln Val Gly Phe
    1115                1120                1125

Val Thr Ile Asn Asp Lys Val Phe Tyr Phe Ser Asp Ser Gly Ile
    1130                1135                1140

Ile Glu Ser Gly Val Gln Asn Ile Asp Asp Asn Tyr Phe Tyr Ile
    1145                1150                1155

Asp Asp Asn Gly Ile Val Gln Ile Gly Val Phe Asp Thr Ser Asp
    1160                1165                1170

Gly Tyr Lys Tyr Phe Ala Pro Ala Asn Thr Val Asn Asp Asn Ile
    1175                1180                1185

Tyr Gly Gln Ala Val Glu Tyr Ser Gly Leu Val Arg Val Gly Glu
    1190                1195                1200

Asp Val Tyr Tyr Phe Gly Glu Thr Tyr Thr Ile Glu Thr Gly Trp
    1205                1210                1215

Ile Tyr Asp Met Glu Asn Glu Ser Asp Lys Tyr Tyr Phe Asn Pro
    1220                1225                1230

Glu Thr Lys Lys Ala Cys Lys Gly Ile Asn Leu Ile Asp Asp Ile
    1235                1240                1245

Lys Tyr Tyr Phe Asp Glu Lys Gly Ile Met Arg Thr Gly Leu Ile
    1250                1255                1260

Ser Phe Glu Asn Asn Asn Tyr Tyr Phe Asn Glu Asn Gly Glu Met
    1265                1270                1275

Gln Phe Gly Tyr Ile Asn Ile Glu Asp Lys Met Phe Tyr Phe Gly
    1280                1285                1290

Glu Asp Gly Val Met Gln Ile Gly Val Phe Asn Thr Pro Asp Gly
    1295                1300                1305

Phe Lys Tyr Phe Ala His Gln Asn Thr Leu Asp Glu Asn Phe Glu
    1310                1315                1320

Gly Glu Ser Ile Asn Tyr Thr Gly Trp Leu Asp Leu Asp Glu Lys
    1325                1330                1335

Arg Tyr Tyr Phe Thr Asp Glu Tyr Ile Ala Ala Thr Gly Ser Val
    1340                1345                1350

Ile Ile Asp Gly Glu Glu Tyr Tyr Phe Asp Pro Asp Thr Ala Gln
    1355                1360                1365

Leu Val Ile Ser Glu Ser Arg Met Val Thr Gly Val Phe Lys Gly
    1370                1375                1380

Pro Asn Gly Phe Glu Tyr Phe Ala Pro Ala Asn Thr His Asn Asn
```

-continued

```
                1385                1390                1395

Asn Ile Glu Gly Gln Ala Ile Val Tyr Gln Asn Lys Phe Leu Thr
                1400                1405                1410

Leu Asn Gly Lys Lys Tyr Tyr Phe Asp Asn Asp Ser Lys Ala Val
                1415                1420                1425

Thr Gly Trp Gln Thr Ile Asp Gly Lys Lys Tyr Tyr Phe Asn Leu
                1430                1435                1440

Asn Thr Ala Glu Ala Ala Thr Gly Trp Gln Thr Ile Asp Gly Lys
                1445                1450                1455

Lys Tyr Tyr Phe Asn Leu Asn Thr Ala Glu Ala Ala Thr Gly Trp
                1460                1465                1470

Gln Thr Ile Asp Gly Lys Lys Tyr Tyr Phe Asn Thr Asn Thr Phe
                1475                1480                1485

Ile Ala Ser Thr Gly Tyr Thr Ser Ile Asn Gly Lys His Phe Tyr
                1490                1495                1500

Phe Asn Thr Asp Gly Ile Met Gln Ile Gly Val Phe Lys Gly Pro
                1505                1510                1515

Asn Gly Phe Glu Tyr Phe Ala Pro Ala Asn Thr Asp Ala Asn Asn
                1520                1525                1530

Ile Glu Gly Gln Ala Ile Leu Tyr Gln Asn Lys Phe Leu Thr Leu
                1535                1540                1545

Asn Gly Lys Lys Tyr Tyr Phe Gly Ser Asp Ser Lys Ala Val Thr
                1550                1555                1560

Gly Leu Arg Thr Ile Asp Gly Lys Lys Tyr Tyr Phe Asn Thr Asn
                1565                1570                1575

Thr Ala Val Ala Val Thr Gly Trp Gln Thr Ile Asn Gly Lys Lys
                1580                1585                1590

Tyr Tyr Phe Asn Thr Asn Thr Ser Ile Ala Ser Thr Gly Tyr Thr
                1595                1600                1605

Ile Ile Ser Gly Lys His Phe Tyr Phe Asn Thr Asp Gly Ile Met
                1610                1615                1620

Gln Ile Gly Val Phe Lys Gly Pro Asp Gly Phe Glu Tyr Phe Ala
                1625                1630                1635

Pro Ala Asn Thr Asp Ala Asn Asn Ile Glu Gly Gln Ala Ile Arg
                1640                1645                1650

Tyr Gln Asn Arg Phe Leu Tyr Leu His Asp Asn Ile Tyr Tyr Phe
                1655                1660                1665

Gly Asn Asn Ser Lys Ala Ala Thr Gly Trp Val Thr Ile Asp Gly
                1670                1675                1680

Asn Arg Tyr Tyr Phe Glu Pro Asn Thr Ala Met Gly Ala Asn Gly
                1685                1690                1695

Tyr Lys Thr Ile Asp Asn Lys Asn Phe Tyr Phe Arg Asn Gly Leu
                1700                1705                1710

Pro Gln Ile Gly Val Phe Lys Gly Ser Asn Gly Phe Glu Tyr Phe
                1715                1720                1725

Ala Pro Ala Asn Thr Asp Ala Asn Asn Ile Glu Gly Gln Ala Ile
                1730                1735                1740

Arg Tyr Gln Asn Arg Phe Leu His Leu Leu Gly Lys Ile Tyr Tyr
                1745                1750                1755

Phe Gly Asn Asn Ser Lys Ala Val Thr Gly Trp Gln Thr Ile Asn
                1760                1765                1770

Gly Lys Val Tyr Tyr Phe Met Pro Asp Thr Ala Met Ala Ala Ala
                1775                1780                1785
```

-continued

```
Gly Gly Leu Phe Glu Ile Asp Gly Val Ile Tyr Phe Phe Gly Val
    1790                1795                1800

Asp Gly Val Lys Ala Pro Gly Ile Tyr Gly Thr Ser Met Val Ser
    1805                1810                1815

Gly Leu Ile Tyr Ile Asn Asp Ser Leu Tyr Tyr Phe Lys Pro Pro
    1820                1825                1830

Val Asn Asn Leu Ile Thr Gly Phe Val Thr Val Gly Asp Asp Lys
    1835                1840                1845

Tyr Tyr Phe Asn Pro Ile Asn Gly Gly Ala Ala Ser Ile Gly Glu
    1850                1855                1860

Thr Ile Ile Asp Asp Lys Asn Tyr Tyr Phe Asn Gln Ser Gly Val
    1865                1870                1875

Leu Gln Thr Gly Val Phe Ser Thr Glu Asp Gly Phe Lys Tyr Phe
    1880                1885                1890

Ala Pro Ala Asn Thr Leu Asp Glu Asn Leu Glu Gly Glu Ala Ile
    1895                1900                1905

Asp Phe Thr Gly Lys Leu Ile Ile Asp Glu Asn Ile Tyr Tyr Phe
    1910                1915                1920

Asp Asp Asn Tyr Arg Gly Ala Val Glu Trp Lys Glu Leu Asp Gly
    1925                1930                1935

Glu Met His Tyr Phe Ser Pro Glu Thr Gly Lys Ala Phe Lys Gly
    1940                1945                1950

Leu Asn Gln Ile Gly Asp Tyr Lys Tyr Tyr Phe Asn Ser Asp Gly
    1955                1960                1965

Val Met Gln Lys Gly Phe Val Ser Ile Asn Asp Asn Lys His Tyr
    1970                1975                1980

Phe Asp Asp Ser Gly Val Met Lys Val Gly Tyr Thr Glu Ile Asp
    1985                1990                1995

Gly Lys His Phe Tyr Phe Ala Glu Asn Gly Glu Met Gln Ile Gly
    2000                2005                2010

Val Phe Asn Thr Glu Asp Gly Phe Lys Tyr Phe Ala His His Asn
    2015                2020                2025

Glu Asp Leu Gly Asn Glu Glu Gly Glu Glu Ile Ser Tyr Ser Gly
    2030                2035                2040

Ile Leu Asn Phe Asn Asn Lys Ile Tyr Tyr Phe Asp Asp Ser Phe
    2045                2050                2055

Thr Ala Val Val Gly Trp Lys Asp Leu Glu Asp Gly Ser Lys Tyr
    2060                2065                2070

Tyr Phe Asp Glu Asp Thr Ala Glu Ala Tyr Ile Gly Leu Ser Leu
    2075                2080                2085

Ile Asn Asp Gly Gln Tyr Tyr Phe Asn Asp Asp Gly Ile Met Gln
    2090                2095                2100

Val Gly Phe Val Thr Ile Asn Asp Lys Val Phe Tyr Phe Ser Asp
    2105                2110                2115

Ser Gly Ile Ile Glu Ser Gly Val Gln Asn Ile Asp Asp Asn Tyr
    2120                2125                2130

Phe Tyr Ile Asp Asp Asn Gly Ile Val Gln Ile Gly Val Phe Asp
    2135                2140                2145

Thr Ser Asp Gly Tyr Lys Tyr Phe Ala Pro Ala Asn Thr Val Asn
    2150                2155                2160

Asp Asn Ile Tyr Gly Gln Ala Val Glu Tyr Ser Gly Leu Val Arg
    2165                2170                2175
```

```
Val Gly Glu Asp Val Tyr Tyr Phe Gly Glu Thr Tyr Thr Ile Glu
    2180                2185                2190

Thr Gly Trp Ile Tyr Asp Met Glu Asn Glu Ser Asp Lys Tyr Tyr
    2195                2200                2205

Phe Asn Pro Glu Thr Lys Lys Ala Cys Lys Gly Ile Asn Leu Ile
    2210                2215                2220

Asp Asp Ile Lys Tyr Tyr Phe Asp Glu Lys Gly Ile Met Arg Thr
    2225                2230                2235

Gly Leu Ile Ser Phe Glu Asn Asn Tyr Tyr Phe Asn Glu Asn
    2240                2245                2250

Gly Glu Met Gln Phe Gly Tyr Ile Asn Ile Glu Asp Lys Met Phe
    2255                2260                2265

Tyr Phe Gly Glu Asp Gly Val Met Gln Ile Gly Val Phe Asn Thr
    2270                2275                2280

Pro Asp Gly Phe Lys Tyr Phe Ala His Gln Asn Thr Leu Asp Glu
    2285                2290                2295

Asn Phe Glu Gly Glu Ser Ile Asn Tyr Thr Gly Trp Leu Asp Leu
    2300                2305                2310

Asp Glu Lys Arg Tyr Tyr Phe Thr Asp Glu Tyr Ile Ala Ala Thr
    2315                2320                2325

Gly Ser Val Ile Ile Asp Gly Glu Glu Tyr Tyr Phe Asp Pro Asp
    2330                2335                2340

Thr Ala Gln Leu Val Ile Ser Glu
    2345                2350

<210> SEQ ID NO 22
<211> LENGTH: 835
<212> TYPE: PRT
<213> ORGANISM: Clostridium difficile
<220> FEATURE:
<221> NAME/KEY: SITE
<222> LOCATION: (588)..(588)
<223> OTHER INFORMATION: Xaa can be any naturally occurring amino acid

<400> SEQUENCE: 22

Met Glu Ile Val Asn Glu Asp Ile Leu Pro Asn Asn Gly Leu Met Gly
1               5                   10                  15

Tyr Tyr Phe Thr Asp Glu His Phe Lys Asp Leu Lys Leu Met Ala Pro
            20                  25                  30

Ile Lys Asp Gly Asn Leu Lys Phe Glu Glu Lys Lys Val Asp Lys Leu
        35                  40                  45

Leu Asp Lys Asp Lys Ser Asp Val Lys Ser Ile Arg Trp Thr Gly Arg
50                  55                  60

Ile Ile Pro Ser Lys Asp Gly Glu Tyr Thr Leu Ser Thr Asp Arg Asp
65                  70                  75                  80

Asp Val Leu Met Gln Val Asn Thr Glu Ser Thr Ile Ser Asn Thr Leu
                85                  90                  95

Lys Val Asn Met Lys Lys Gly Lys Glu Tyr Lys Val Arg Ile Glu Leu
            100                 105                 110

Gln Asp Lys Asn Leu Gly Ser Ile Asp Asn Leu Ser Ser Pro Asn Leu
        115                 120                 125

Tyr Trp Glu Leu Asp Gly Met Lys Lys Ile Ile Pro Glu Glu Asn Leu
    130                 135                 140

Phe Leu Arg Asp Tyr Ser Asn Ile Glu Lys Asp Asp Pro Phe Ile Pro
145                 150                 155                 160

Asn Asn Asn Phe Phe Asp Pro Lys Leu Met Ser Asp Trp Glu Asp Glu
```

```
            165                 170                 175
Asp Leu Asp Thr Asp Asn Asp Asn Ile Pro Asp Ser Tyr Glu Arg Asn
            180                 185                 190

Gly Tyr Thr Ile Lys Asp Leu Ile Ala Val Lys Trp Glu Asp Ser Phe
            195                 200                 205

Ala Glu Gln Gly Tyr Lys Lys Tyr Val Ser Asn Tyr Leu Glu Ser Asn
            210                 215                 220

Thr Ala Gly Asp Pro Tyr Thr Asp Tyr Glu Lys Ala Ser Gly Ser Phe
225                 230                 235                 240

Asp Lys Ala Ile Lys Thr Glu Ala Arg Asp Pro Leu Val Ala Ala Tyr
            245                 250                 255

Pro Ile Val Gly Val Gly Met Glu Lys Leu Ile Ile Ser Thr Asn Glu
            260                 265                 270

His Ala Ser Thr Asp Gln Gly Lys Thr Val Ser Arg Ala Thr Thr Asn
            275                 280                 285

Ser Lys Thr Glu Ser Asn Thr Ala Gly Val Ser Val Asn Val Gly Tyr
            290                 295                 300

Gln Asn Gly Phe Thr Ala Asn Val Thr Thr Asn Tyr Ser His Thr Thr
305                 310                 315                 320

Asp Asn Ser Thr Ala Val Gln Asp Ser Asn Gly Glu Ser Trp Asn Thr
                    325                 330                 335

Gly Leu Ser Ile Asn Lys Gly Glu Ser Ala Tyr Ile Asn Ala Asn Val
                    340                 345                 350

Arg Tyr Tyr Asn Thr Gly Thr Ala Pro Met Tyr Lys Val Thr Pro Thr
            355                 360                 365

Thr Asn Leu Val Leu Asp Gly Asp Thr Leu Ser Thr Ile Lys Ala Gln
            370                 375                 380

Glu Asn Gln Ile Gly Asn Asn Leu Ser Pro Gly Asp Thr Tyr Pro Lys
385                 390                 395                 400

Lys Gly Leu Ser Pro Leu Ala Leu Asn Thr Met Asp Gln Phe Ser Ser
                    405                 410                 415

Arg Leu Ile Pro Ile Asn Tyr Asp Gln Leu Lys Lys Leu Asp Ala Gly
            420                 425                 430

Lys Gln Ile Lys Leu Glu Thr Gln Val Ser Gly Asn Phe Gly Thr
            435                 440                 445

Lys Asn Ser Ser Gly Gln Ile Val Thr Glu Gly Asn Ser Trp Ser Asp
            450                 455                 460

Tyr Ile Ser Gln Ile Asp Ser Ile Ser Ala Ser Ile Ile Leu Asp Thr
465                 470                 475                 480

Glu Asn Glu Ser Tyr Glu Arg Arg Val Thr Ala Lys Asn Leu Gln Asp
                    485                 490                 495

Pro Glu Asp Lys Thr Pro Glu Leu Thr Ile Gly Glu Ala Ile Glu Lys
            500                 505                 510

Ala Phe Gly Ala Thr Lys Lys Asp Gly Leu Leu Tyr Phe Asn Asp Ile
            515                 520                 525

Pro Ile Asp Glu Ser Cys Val Glu Leu Ile Phe Asp Asp Asn Thr Ala
            530                 535                 540

Asn Lys Ile Lys Asp Ser Leu Lys Thr Leu Ser Asp Lys Lys Ile Tyr
545                 550                 555                 560

Asn Val Lys Leu Glu Arg Gly Met Asn Ile Leu Ile Lys Thr Pro Thr
                    565                 570                 575

Tyr Phe Thr Asn Phe Asp Asp Tyr Asn Asn Tyr Xaa Ser Thr Trp Ser
                    580                 585                 590
```

```
Asn Val Asn Thr Thr Asn Gln Asp Gly Leu Gln Gly Ser Ala Asn Lys
            595                 600                 605

Leu Asn Gly Glu Thr Lys Ile Lys Ile Pro Met Ser Glu Leu Lys Pro
610                 615                 620

Tyr Lys Arg Tyr Val Phe Ser Gly Tyr Ser Lys Asp Pro Leu Thr Ser
625                 630                 635                 640

Asn Ser Ile Ile Val Lys Ile Lys Ala Lys Glu Glu Lys Thr Asp Tyr
            645                 650                 655

Leu Val Pro Glu Gln Gly Tyr Thr Lys Phe Ser Tyr Glu Phe Glu Thr
            660                 665                 670

Thr Glu Lys Asp Ser Ser Asn Ile Glu Ile Thr Leu Ile Gly Ser Gly
            675                 680                 685

Thr Thr Tyr Leu Asp Asn Leu Ser Ile Thr Glu Leu Asn Ser Thr Pro
690                 695                 700

Glu Ile Leu Asp Glu Pro Glu Val Lys Ile Pro Thr Asp Gln Glu Ile
705                 710                 715                 720

Met Asp Ala His Lys Ile Tyr Phe Ala Asp Leu Asn Phe Asn Pro Ser
                725                 730                 735

Thr Gly Asn Thr Tyr Ile Asn Gly Met Tyr Phe Ala Pro Thr Gln Thr
            740                 745                 750

Asn Lys Glu Ala Leu Asp Tyr Ile Gln Lys Tyr Arg Val Glu Ala Thr
            755                 760                 765

Leu Gln Tyr Ser Gly Phe Lys Asp Ile Gly Thr Lys Asp Lys Glu Met
            770                 775                 780

Arg Asn Tyr Leu Gly Asp Pro Asn Gln Pro Lys Thr Asn Tyr Val Asn
785                 790                 795                 800

Leu Arg Ser Tyr Phe Thr Gly Gly Glu Asn Ile Met Thr Tyr Lys Lys
                805                 810                 815

Leu Arg Ile Tyr Ala Ile Thr Pro Asp Asp Arg Glu Leu Leu Val Leu
            820                 825                 830

Ser Val Asp
        835

<210> SEQ ID NO 23
<211> LENGTH: 536
<212> TYPE: PRT
<213> ORGANISM: Clostridium difficile

<400> SEQUENCE: 23

Met Val Ser Gly Leu Ile Tyr Ile Asn Asp Ser Leu Tyr Tyr Phe Lys
1               5                   10                  15

Pro Pro Val Asn Asn Leu Ile Thr Gly Phe Val Thr Val Gly Asp Asp
                20                  25                  30

Lys Tyr Tyr Phe Asn Pro Ile Asn Gly Gly Ala Ala Ser Ile Gly Glu
            35                  40                  45

Thr Ile Ile Asp Asp Lys Asn Tyr Tyr Phe Asn Gln Ser Gly Val Leu
        50                  55                  60

Gln Thr Gly Val Phe Ser Thr Glu Asp Gly Phe Lys Tyr Phe Ala Pro
65              70                  75                  80

Ala Asn Thr Leu Asp Glu Asn Leu Glu Gly Glu Ala Ile Asp Phe Thr
                85                  90                  95

Gly Lys Leu Ile Ile Asp Glu Asn Ile Tyr Tyr Phe Asp Asp Asn Tyr
            100                 105                 110

Arg Gly Ala Val Glu Trp Lys Glu Leu Asp Gly Glu Met His Tyr Phe
```

-continued

```
            115                 120                 125
Ser Pro Glu Thr Gly Lys Ala Phe Lys Gly Leu Asn Gln Ile Gly Asp
130                 135                 140

Tyr Lys Tyr Tyr Phe Asn Ser Asp Gly Val Met Gln Lys Gly Phe Val
145                 150                 155                 160

Ser Ile Asn Asp Asn Lys His Tyr Phe Asp Ser Gly Val Met Lys
                165                 170                 175

Val Gly Tyr Thr Glu Ile Asp Gly Lys His Phe Tyr Phe Ala Glu Asn
                180                 185                 190

Gly Glu Met Gln Ile Gly Val Phe Asn Thr Glu Asp Gly Phe Lys Tyr
                195                 200                 205

Phe Ala His His Asn Glu Asp Leu Gly Asn Glu Glu Gly Glu Glu Ile
210                 215                 220

Ser Tyr Ser Gly Ile Leu Asn Phe Asn Asn Lys Ile Tyr Tyr Phe Asp
225                 230                 235                 240

Asp Ser Phe Thr Ala Val Val Gly Trp Lys Asp Leu Glu Asp Gly Ser
                245                 250                 255

Lys Tyr Tyr Phe Asp Glu Asp Thr Ala Glu Ala Tyr Ile Gly Leu Ser
                260                 265                 270

Leu Ile Asn Asp Gly Gln Tyr Tyr Phe Asn Asp Gly Ile Met Gln
                275                 280                 285

Val Gly Phe Val Thr Ile Asn Asp Lys Val Phe Tyr Phe Ser Asp Ser
290                 295                 300

Gly Ile Ile Glu Ser Gly Val Gln Asn Ile Asp Asp Asn Tyr Phe Tyr
305                 310                 315                 320

Ile Asp Asp Asn Gly Ile Val Gln Ile Gly Val Phe Asp Thr Ser Asp
                325                 330                 335

Gly Tyr Lys Tyr Phe Ala Pro Ala Asn Thr Val Asn Asp Asn Ile Tyr
                340                 345                 350

Gly Gln Ala Val Glu Tyr Ser Gly Leu Val Arg Val Gly Glu Asp Val
                355                 360                 365

Tyr Tyr Phe Gly Glu Thr Tyr Thr Ile Glu Thr Gly Trp Ile Tyr Asp
370                 375                 380

Met Glu Asn Glu Ser Asp Lys Tyr Tyr Phe Asn Pro Glu Thr Lys Lys
385                 390                 395                 400

Ala Cys Lys Gly Ile Asn Leu Ile Asp Asp Ile Lys Tyr Tyr Phe Asp
                405                 410                 415

Glu Lys Gly Ile Met Arg Thr Gly Leu Ile Ser Phe Glu Asn Asn Asn
                420                 425                 430

Tyr Tyr Phe Asn Glu Asn Gly Glu Met Gln Phe Gly Tyr Ile Asn Ile
                435                 440                 445

Glu Asp Lys Met Phe Tyr Phe Gly Glu Asp Gly Val Met Gln Ile Gly
                450                 455                 460

Val Phe Asn Thr Pro Asp Gly Phe Lys Tyr Phe Ala His Gln Asn Thr
465                 470                 475                 480

Leu Asp Glu Asn Phe Glu Gly Glu Ser Ile Asn Tyr Thr Gly Trp Leu
                485                 490                 495

Asp Leu Asp Glu Lys Arg Tyr Tyr Phe Thr Asp Glu Tyr Ile Ala Ala
                500                 505                 510

Thr Gly Ser Val Ile Ile Asp Gly Glu Glu Tyr Tyr Phe Asp Pro Asp
                515                 520                 525

Thr Ala Gln Leu Val Ile Ser Glu
                530                 535
```

<210> SEQ ID NO 24
<211> LENGTH: 438
<212> TYPE: PRT
<213> ORGANISM: Clostridium difficile

<400> SEQUENCE: 24

```
Met Val Thr Gly Val Phe Lys Gly Pro Asn Gly Phe Glu Tyr Phe Ala
1               5                   10                  15

Pro Ala Asn Thr His Asn Asn Asn Ile Glu Gly Gln Ala Ile Val Tyr
            20                  25                  30

Gln Asn Lys Phe Leu Thr Leu Asn Gly Lys Lys Tyr Tyr Phe Asp Asn
        35                  40                  45

Asp Ser Lys Ala Val Thr Gly Trp Gln Thr Ile Asp Gly Lys Lys Tyr
    50                  55                  60

Tyr Phe Asn Leu Asn Thr Ala Glu Ala Ala Thr Gly Trp Gln Thr Ile
65                  70                  75                  80

Asp Gly Lys Lys Tyr Tyr Phe Asn Leu Asn Thr Ala Glu Ala Ala Thr
                85                  90                  95

Gly Trp Gln Thr Ile Asp Gly Lys Lys Tyr Tyr Phe Asn Thr Asn Thr
            100                 105                 110

Phe Ile Ala Ser Thr Gly Tyr Thr Ser Ile Asn Gly Lys His Phe Tyr
        115                 120                 125

Phe Asn Thr Asp Gly Ile Met Gln Ile Gly Val Phe Lys Gly Pro Asn
    130                 135                 140

Gly Phe Glu Tyr Phe Ala Pro Ala Asn Thr Asp Ala Asn Asn Ile Glu
145                 150                 155                 160

Gly Gln Ala Ile Leu Tyr Gln Asn Lys Phe Leu Thr Leu Asn Gly Lys
                165                 170                 175

Lys Tyr Tyr Phe Gly Ser Asp Ser Lys Ala Val Thr Gly Leu Arg Thr
            180                 185                 190

Ile Asp Gly Lys Lys Tyr Tyr Phe Asn Thr Asn Thr Ala Val Ala Val
        195                 200                 205

Thr Gly Trp Gln Thr Ile Asn Gly Lys Lys Tyr Tyr Phe Asn Thr Asn
    210                 215                 220

Thr Ser Ile Ala Ser Thr Gly Tyr Thr Ile Ile Ser Gly Lys His Phe
225                 230                 235                 240

Tyr Phe Asn Thr Asp Gly Ile Met Gln Ile Gly Val Phe Lys Gly Pro
                245                 250                 255

Asp Gly Phe Glu Tyr Phe Ala Pro Ala Asn Thr Asp Ala Asn Asn Ile
            260                 265                 270

Glu Gly Gln Ala Ile Arg Tyr Gln Asn Arg Phe Leu Tyr Leu His Asp
        275                 280                 285

Asn Ile Tyr Tyr Phe Gly Asn Asn Ser Lys Ala Ala Thr Gly Trp Val
    290                 295                 300

Thr Ile Asp Gly Asn Arg Tyr Tyr Phe Glu Pro Asn Thr Ala Met Gly
305                 310                 315                 320

Ala Asn Gly Tyr Lys Thr Ile Asp Asn Lys Asn Phe Tyr Phe Arg Asn
                325                 330                 335

Gly Leu Pro Gln Ile Gly Val Phe Lys Gly Ser Asn Gly Phe Glu Tyr
            340                 345                 350

Phe Ala Pro Ala Asn Thr Asp Ala Asn Asn Ile Glu Gly Gln Ala Ile
        355                 360                 365

Arg Tyr Gln Asn Arg Phe Leu His Leu Leu Gly Lys Ile Tyr Tyr Phe
```

```
                370                 375                 380
Gly Asn Asn Ser Lys Ala Val Thr Gly Trp Gln Thr Ile Asn Gly Lys
385                 390                 395                 400

Val Tyr Tyr Phe Met Pro Asp Thr Ala Met Ala Ala Gly Gly Leu
                405                 410                 415

Phe Glu Ile Asp Gly Val Ile Tyr Phe Gly Val Asp Gly Val Lys
                420                 425                 430

Ala Pro Gly Ile Tyr Gly
            435

<210> SEQ ID NO 25
<211> LENGTH: 536
<212> TYPE: PRT
<213> ORGANISM: Clostridium difficile

<400> SEQUENCE: 25

Met Val Ser Gly Leu Ile Tyr Ile Asn Asp Ser Leu Tyr Tyr Phe Lys
1               5                   10                  15

Pro Pro Val Asn Asn Leu Ile Thr Gly Phe Val Thr Val Gly Asp Asp
                20                  25                  30

Lys Tyr Tyr Phe Asn Pro Ile Asn Gly Gly Ala Ala Ser Ile Gly Glu
            35                  40                  45

Thr Ile Ile Asp Asp Lys Asn Tyr Tyr Phe Asn Gln Ser Gly Val Leu
        50                  55                  60

Gln Thr Gly Val Phe Ser Thr Glu Asp Gly Phe Lys Tyr Phe Ala Pro
65                  70                  75                  80

Ala Asn Thr Leu Asp Glu Asn Leu Glu Gly Glu Ala Ile Asp Phe Thr
                85                  90                  95

Gly Lys Leu Ile Ile Asp Glu Asn Ile Tyr Tyr Phe Asp Asp Asn Tyr
            100                 105                 110

Arg Gly Ala Val Glu Trp Lys Glu Leu Asp Gly Glu Met His Tyr Phe
        115                 120                 125

Ser Pro Glu Thr Gly Lys Ala Phe Lys Gly Leu Asn Gln Ile Gly Asp
    130                 135                 140

Tyr Lys Tyr Tyr Phe Asn Ser Asp Gly Val Met Gln Lys Gly Phe Val
145                 150                 155                 160

Ser Ile Asn Asp Asn Lys His Tyr Phe Asp Asp Ser Gly Val Met Lys
                165                 170                 175

Val Gly Tyr Thr Glu Ile Asp Gly Lys His Phe Tyr Phe Ala Glu Asn
            180                 185                 190

Gly Glu Met Gln Ile Gly Val Phe Asn Thr Glu Asp Gly Phe Lys Tyr
        195                 200                 205

Phe Ala His His Asn Glu Asp Leu Gly Asn Glu Glu Gly Glu Glu Ile
    210                 215                 220

Ser Tyr Ser Gly Ile Leu Asn Phe Asn Asn Lys Ile Tyr Tyr Phe Asp
225                 230                 235                 240

Asp Ser Phe Thr Ala Val Val Gly Trp Lys Asp Leu Glu Asp Gly Ser
                245                 250                 255

Lys Tyr Tyr Phe Asp Glu Asp Thr Ala Glu Ala Tyr Ile Gly Leu Ser
            260                 265                 270

Leu Ile Asn Asp Gly Gln Tyr Tyr Phe Asn Asp Asp Gly Ile Met Gln
        275                 280                 285

Val Gly Phe Val Thr Ile Asn Asp Lys Val Phe Tyr Phe Ser Asp Ser
    290                 295                 300
```

```
Gly Ile Ile Glu Ser Gly Val Gln Asn Ile Asp Asp Asn Tyr Phe Tyr
305                 310                 315                 320

Ile Asp Asp Asn Gly Ile Val Gln Ile Gly Val Phe Asp Thr Ser Asp
            325                 330                 335

Gly Tyr Lys Tyr Phe Ala Pro Ala Asn Thr Val Asn Asp Asn Ile Tyr
            340                 345                 350

Gly Gln Ala Val Glu Tyr Ser Gly Leu Val Arg Val Gly Glu Asp Val
            355                 360                 365

Tyr Tyr Phe Gly Glu Thr Tyr Thr Ile Glu Thr Gly Trp Ile Tyr Asp
370                 375                 380

Met Glu Asn Glu Ser Asp Lys Tyr Tyr Phe Asn Pro Glu Thr Lys Lys
385                 390                 395                 400

Ala Cys Lys Gly Ile Asn Leu Ile Asp Asp Ile Lys Tyr Tyr Phe Asp
            405                 410                 415

Glu Lys Gly Ile Met Arg Thr Gly Leu Ile Ser Phe Glu Asn Asn Asn
            420                 425                 430

Tyr Tyr Phe Asn Glu Asn Gly Glu Met Gln Phe Gly Tyr Ile Asn Ile
            435                 440                 445

Glu Asp Lys Met Phe Tyr Phe Gly Glu Asp Gly Val Met Gln Ile Gly
450                 455                 460

Val Phe Asn Thr Pro Asp Gly Phe Lys Tyr Phe Ala His Gln Asn Thr
465                 470                 475                 480

Leu Asp Glu Asn Phe Glu Gly Glu Ser Ile Asn Tyr Thr Gly Trp Leu
            485                 490                 495

Asp Leu Asp Glu Lys Arg Tyr Tyr Phe Thr Asp Glu Tyr Ile Ala Ala
            500                 505                 510

Thr Gly Ser Val Ile Ile Asp Gly Glu Glu Tyr Tyr Phe Asp Pro Asp
            515                 520                 525

Thr Ala Gln Leu Val Ile Ser Glu
            530                 535

<210> SEQ ID NO 26
<211> LENGTH: 4
<212> TYPE: PRT
<213> ORGANISM: Artificial Sequence
<220> FEATURE:
<223> OTHER INFORMATION: synthetically synthesized peptide linker

<400> SEQUENCE: 26

Gly Gly Gly Gly
1

<210> SEQ ID NO 27
<211> LENGTH: 8
<212> TYPE: PRT
<213> ORGANISM: Unknown
<220> FEATURE:
<223> OTHER INFORMATION: furin cleavage site sequence

<400> SEQUENCE: 27

Arg Ala Arg Arg Arg Lys Lys Arg
1               5

<210> SEQ ID NO 28
<211> LENGTH: 24
<212> TYPE: DNA
<213> ORGANISM: Unknown
<220> FEATURE:
<223> OTHER INFORMATION: furin cleavage site sequence
```

```
<400> SEQUENCE: 28
cgcgctcgcc gccgcaagaa gcgc                                              24
```

US 11,938,179 B2

METHODS AND COMPOSITIONS FOR INDUCING IMMUNE RESPONSES AGAINST *CLOSTRIDIUM DIFFICILE*

CROSS REFERENCE TO RELATED APPLICATIONS

This application is a continuation of U.S. application Ser. No. 16/494,517, filed Sep. 16, 2019, which is a national phase filing under 35 U.S.C. § 371 of International Patent Application No. PCT/US2018/022597, filed Mar. 15, 2018, which claims the benefit of priority to U.S. Provisional Application Nos. 62/471,636, filed Mar. 15, 2017 and 62/474,434, filed Mar. 21, 2017, the disclosures of which are each incorporated in its entirety herein for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: NOVV_058_03US_Seq_List_ST25, date recorded: Aug. 10, 2021, file size 172 kilobytes).

BACKGROUND

Vaccination against disease using a subunit-based vaccine is dependent on producing sufficient amounts of the protein antigen and maintaining stability of the antigen such that the protein remains effective when administered to a target population.

Complications in producing subunit vaccines arise at multiple steps during production. The target protein can be produced at low levels, or can be insoluble, resulting in economically-unfavorable production, even when the protein had particularly favorable immunogenicity profile.

Bacterial infections remain a health concern. Indeed, bacterial vaccines are increasingly sought after as bacteria evolve resistance to front-line antibiotics. Bacterial subunit vaccines rely on recombinant protein production. However, bacterial proteins can often be difficult to produce at high level due to low expression, and insolubility, and they can also suffer from reduced stability. Better approaches to producing vaccines, particularly for difficult antigen targets, would thus provide global health benefits. In particular, infection by clostridial bacteria, notably *C. dificile* remains a particular problem. *Clostridium difficile* infection (CDI) is the leading cause of nosocomial antibiotic-associated diarrhea in developed countries. Hypervirulent strains have evolved causing severe disease with increased mortality. Homologous glucosylating toxins, TcdA and TcdB, and binary ADP-ribosylating toxin (CDT) are major virulence factors causing pathogenesis. There is an unmet need for vaccines targeting these toxins.

SUMMARY OF THE INVENTION

Disclosed herein are methods and compositions of inducing immune responses against *C. difficile*. The compositions contain polypeptides containing multiple *C. difficile* toxins, which, when administered to a subject, induce advantageous immune responses. Methods for producing the multi-toxin polypeptides are also disclosed.

BRIEF DESCRIPTION OF THE FIGURES

FIG. 1. *C. difficile* triple toxin vaccine constructs. Figure shows illustration of *C. diff* triple toxin vaccine containing the binding domains of CDTb, Tcd B, and Tcd A with (construct 1420) and without (construct 1470) a furin cleavage site having the amino acid sequence of SEQ ID NO: 27 after the activation domain of CDTb.

FIG. 2. Expression and solubility of triple toxin vaccine BV1470 and BV1420. *Spodoptera frugiperda* Sf9 insect cells were infected at a MOI of 0.1 with recombinant baculovirus BV1420 and BV1470, harvested at 48 and 72 hours postinfection, and analyzed for protein expression by SDS-PAGE and coomassie staining. An equal volume of total protein (T, cells and medium) and clarified medium (M) were mixed with 2×SDS-PAGE sample buffer and run on a 4%-12% polyacrylamide NuPage gel. Pelleted, infected cells were solubilized in 1% NP9, 25 mM Tris, 50 mM NaCL, pH 8.0 buffer. Lysed cells were centrifuged at 9000×g for 40 min. Supernatant (S, soluble) was removed, pellet (I, insoluble) was suspended in buffer to original volume, and analyzed by SDS-PAGE as described above. Location of triple toxin protein marked with an arrow.

FIG. 3. Time course expression of triple toxin vaccine BV1470 and BV1420. *Spodoptera frugiperda* Sf9 insect cells were infected with recombinant baculovirus BV1420 and BV1470, as described in FIG. 6. Total protein, medium, soluble, and insoluble protein was analyzed by SDS-PAGE and coomassie staining at various timepoints postinfection. Location of triple toxin protein is marked with an arrow.

FIG. 4. Purification of triple toxin vaccine. The triple toxin vaccine was purified from total cell culture of infected Sf9 cells following the addition of NP9 to a final concentration of 0.2%. NP9 extract was clarified twice and purified on consecutive Fractogel EMD TMAE, Phenyl HP, and Source 30Q columns. The triple toxin was eluted from each column and loaded onto the next column as shown. Eluted triple toxin positive fractions from the Source 30Q column were pooled and filter sterilized through a 0.2 µM filter.

FIG. 5. Purification of triple toxin vaccine BV1470 from Sf9 cells. Triple toxin vaccine BV1470 was purified from infected cells as described in FIG. 8. Final filtered product from the Source 30Q column was analyzed for purity by SDS-PAGE and coomassie staining. Triple toxin protein was identified by western blot using anti-CDTb, anti-TcdB, and antiTcdA antibodies.

FIG. 6. Purification of triple toxin vaccine BV1420 from Sf9 cells. Triple toxin vaccine BV1420 was purified from infected cells as described in FIG. 8. Final filtered product from the Source 30Q column was analyzed for purity by SDS-PAGE and coomassie staining. Triple toxin protein was identified by western blot using anti-TcdB antibodies.

FIG. 7. Particle size distribution by volume graph for triple toxin BV1420. Particle size of triple toxin BV1420 was determined by dynamic light scattering using a Zeta Sizer Nano. Graph of size distribution by volume is shown.

FIG. 8. Particle size distribution by intensity graph for triple toxin BV1470. Particle size of triple toxin BV1420 was determined by dynamic light scattering using a Zeta Sizer Nano. Graph of size distribution by intensity is shown.

FIGS. 9A-9D. Electronmicrographs of negative stained triple toxin BV1420. Electron-micrograph of purified triple toxin BV1420 was diluted to approximately 10 ug/ml and negatively stained with uranyl acetate.

FIG. 10. BV1420 triple toxin vaccine mouse lethal toxin challenge study 1. Mice were immunized on day zero and day 14 with triple toxin vaccine BV1420 and challenged on day 35 with a lethal dose of Tcd A or CDT and monitored for 10 days post challenge. Mice were bleed as shown and serum analyzed for anti-toxin IgG and for toxin neutralizing antibodies. Animals were monitored for mortality and morbidity for 10 days after toxin challenge.

FIG. 11. BV1420 triple toxin vaccine mouse lethal toxin challenge study 1—serum anti-toxin IgG responses. Day 42 serum samples were assayed for Anti-Tcd A, anti-Tcd B, and anti-CDT IgG titers by ELISA using native toxins bound to plates.

FIG. 12. BV1420 triple toxin vaccine mouse lethal toxin challenge study 1—toxin neutralizing antibody (TNA) titers. Toxin neutralization titers were determined using a colorimetric Vero cell based assay. Titer indicated are the reciprocal of the highest dilution of serum that did not kill cells.

FIG. 13. BV1420 triple toxin vaccine mouse lethal toxin challenge study 1—animal survival. Animal survival was determined 10 days post challenge. Animals showing greater than 20% weight loss were sacrificed and recorded as dead.

FIG. 14. BV1420 triple toxin vaccine mouse lethal toxin challenge study 2—toxin B survival. Mice were immunized on day zero and day 14 with triple toxin vaccine BV1420 and challenged on day 35 with a lethal dose of Tcd B and monitored for 10 days post challenge. Mice were bled as shown and serum analyzed for anti-toxin IgG and for toxin neutralizing antibodies (TNA). Animals were monitored for mortality and morbidity for 10 days after toxin challenge.

FIG. 15. BV1420 triple toxin vaccine mouse lethal toxin challenge study 2—anti-toxin IgG levels. Day 42 serum samples were assayed for Anti-Tcd A, anti-Tcd B, and anti-CDT IgG titers by ELISA using native toxins bound to plates.

FIG. 16. BV1420 triple toxin vaccine mouse lethal toxin challenge study 2—toxin B TNA titers. Toxin neutralization titers were determined using a colorimetric Vero cell based assay. Titer indicated are the reciprocal of the highest dilution of serum that did not kill cells.

FIG. 17. BV1420 triple toxin vaccine mouse lethal toxin challenge study 2—toxin B survival. Animal survival was determined 10 days post challenge. Animals showing greater than 20% weight loss were sacrificed and recorded as dead.

FIG. 18. Additional vaccine proteins with the TcdB gene translocation domain are shown. BV1512 is shown in the bottom diagram.

FIG. 19. Multimer Protein Expression: Expression and western blot analysis of multimer protein BV1512.

FIG. 20. Quadrivalent Multimer Protein Expression: FIG. 25 illustrates two quadrivalent multimer proteins. In both cases, a peptide from a second TcdB strain is introduced to broaden immunity against multiple strains. In the upper diagram, the TcdB peptide from Strain 027 is added at the C-terminus. In the lower diagram, the peptide is introduced between the TcdB protein and the TcdA(R19) protein from the first strain, strain 630.

FIG. 21. Quadrivalent Multimer Protein Expression: Expression and western blot analysis of the quadrivalent protein shown in the upper diagram of FIG. 20.

FIG. 22. Quadrivalent Multimer Protein Expression: Expression and western blot analysis of the quadrivalent protein shown in the lower diagram of FIG. 20.

FIG. 23A shows the illustration of the functional domains of *C. difficile* toxin A (TcdA), toxin B (TcdB), and binary toxin (CDT) used to construct the chimeric trivalent and quadrivalent toxin fusion proteins. TcdA and TcdB share common functional domains including the enzymatic glucosyltransferase (GT) domain, autocatalytic cysteine protease (CP) domain, pore-forming translocation (PT) domain (orange), and receptor binding domain (RBD). The binary toxin (CDT) consists of the enzymatic ADP-ribosyltransferase component (CDTa) and receptor binding component (CDTb). CDTb contains a 42 amino acid (aa) signal sequence with two serine-type proteolytic cleavage sites (arrow) which, when cleaved, generates a 20 kDa and 75 kDa fragment. FIG. 24B shows the illustration of the chimeric trivalent toxin fusion protein (T-toxin) and a chimeric quadravalent toxin fusion protein (Q-toxin). The T-toxin fusion protein consists of the full-length coding sequence for CDTb with the RBD of TcdB$_{(003)}$ containing 24 repeats and the truncated RBD of TcdA with 19 repeats. The expressed T-toxin fusion protein consists of 1813 aa with a molecular weight (MW) of 205 kDa. The Q toxin fusion protein consists of the full-length coding sequence for CDTb to the RBD of TcdBro$_{(003)}$ containing 24 repeats, the RBD of TcdA truncated at 19 repeats, and the RBD of TcdB$_{(027)}$ containing 24 repeats. The expressed Q-toxin fusion protein consists of 2359 aa with a molecular weight of 268 kDa.

FIGS. 24A-24C. Expression and Purification of T-Toxin and Q-Toxin Fusion Proteins. SDS-PAGE of purified T-toxin (lanes 2 and 3) migrates with a molecular weight of 205 kDa and Q-toxin (lanes 4 and 5) migrates with a molecular weight of 268 kDa. Molecular weight marker (lane 1). FIG. 24A shows T-toxin and Q-toxin purity was >90% as determined by SDS-PAGE scanning densitometry. FIG. 24B shows western blot analysis as probed with rabbit anti-CDTb specific antibodies. FIG. 24C shows western blot analysis as probed with chicken anti-TcdB specific antibodies. FIG. 24D shows western blot analysis as probed with chicken anti-TcdA specific antibodies.

FIGS. 25A-25C. Immunogenicity of T-Toxin and Q-Toxin Fusion Proteins in Mice. Groups of female C57BL/6 mice (N=10/group) were immunized IM on Days 0 and 14 with T-toxin (100 μg) or Q-toxin (100 μg) adjuvanted with alum (50 μg), or PBS (control group). Serum was collected 18 days after the second vaccination. FIG. 25A shows serum IgG titers to TcdA, TcdB$_{(003)}$, and CDTb determined by ELISA. FIG. 25B shows toxin-neutralizing antibody titers for each toxin determined in the Vero cell assay. In FIG. 25C, Mice received a lethal dose (MLD$_{100\%}$=2.0 μg) of TcdB$_{(003)}$ administered IP 21 days after the second immunization. *Significance was determined by Mantel-Cox logrank test comparing the T-toxin or Q-toxin groups to the PBS control group.

FIGS. 26A-26D. Immunogenicity of T-Toxin and Q-Toxin Fusion Proteins in Hamsters. Male hamsters (N=8/group) were immunized IM 3 times at 21-day intervals with 30 μg Q-toxin adjuvanted with 120 μg alum, or PBS (control group). Two weeks after the third dose, samples were collected and analyzed. FIG. 26A shows serum IgG titers to TcdA, TcdB$_{(003)}$, and CDTb determined by ELISA. FIG. 26B shows toxin-neutralizing antibody titers for each toxin determined in the Vero cell assay. In FIGS. 26C and 26D, two weeks after the third immunization, all animals were treated with clindamycin (10 mg/kg) IP one day prior to spore challenge and were challenged by gavage with 200 cfu *C. difficile* strain 630 (C) or with 500 cfu *C. difficile* strain B1/NAP1/027 (D). Animals were observed for 8 days post challenge.

DETAILED DESCRIPTION OF THE INVENTION

Definitions

Figure 9B:
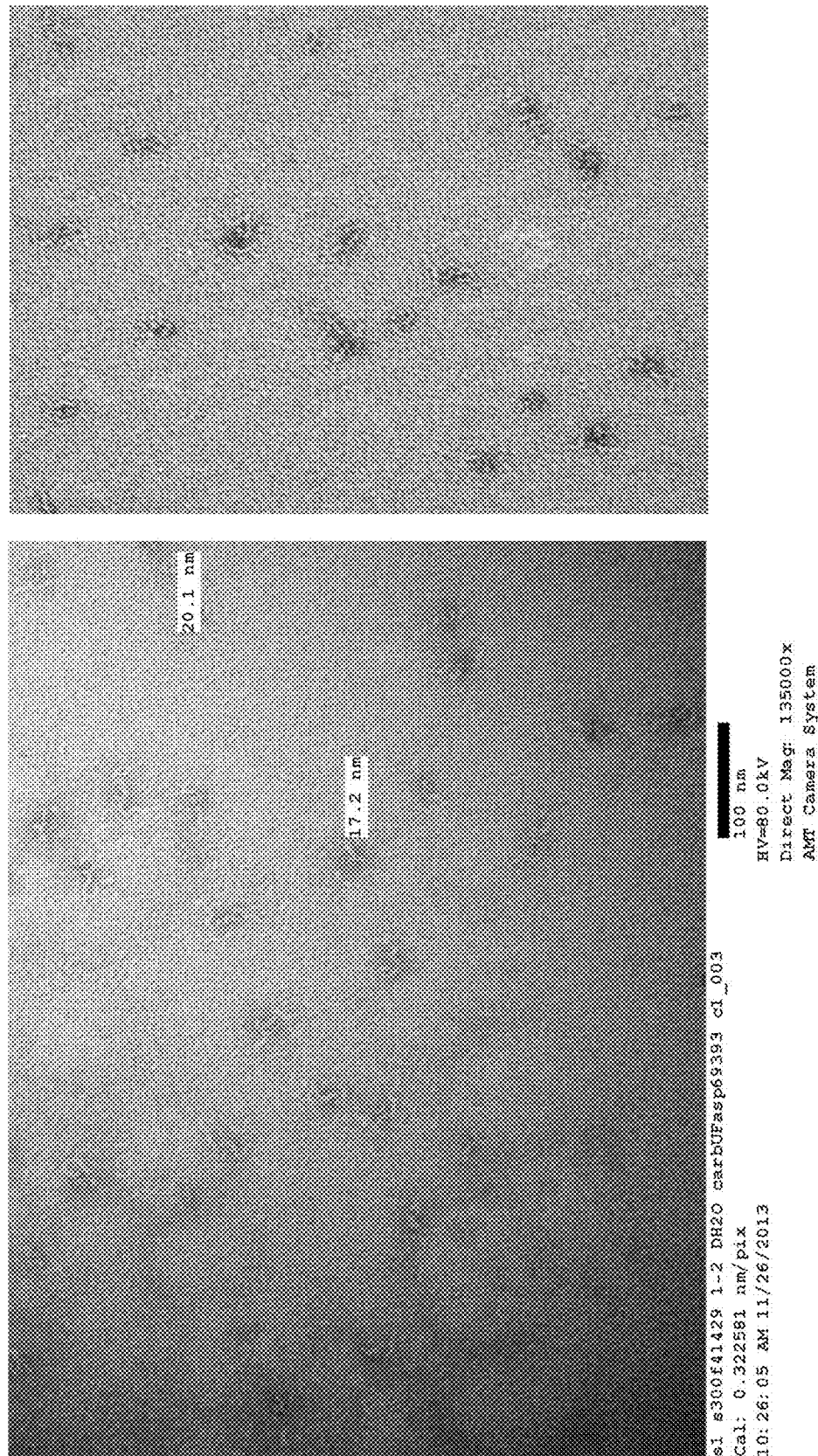

As used herein, the term "adjuvant" refers to a compound that, when used in combination with an immunogen, augments or otherwise alters or modifies the immune response induced against the immunogen. Modification of the immune response may include intensification or broadening the specificity of either or both antibody and cellular immune responses.

As used herein, the terms "immunogen," "antigen," and "epitope" are used interchangeably and refer to substances such as proteins, and peptides that are capable of eliciting an immune response.

As used herein, the term "fusion protein" means a protein comprised of two or more proteins or protein fragments that are joined or fused, directly or indirectly via a linking peptide, at the amino terminus of one protein and the carboxy terminus of another protein, to form a single continuous polypeptide. In some aspects, a fusion protein may be referred to as a "multivalent protein." A multivalent protein contains proteins or protein fragments from two or more three discrete protein antigens that are fused together.

The terms "treat," "treatment," and "treating," as used herein, refer to an approach for obtaining beneficial or desired results, for example, clinical results. For the purposes of this invention, beneficial or desired results may include inhibiting or suppressing the initiation or progression of an infection or a disease; ameliorating, or reducing the development of, symptoms of an infection or disease; or a combination thereof.

"Prevention," as used herein, is used interchangeably with "prophylaxis" and can mean complete prevention of an infection or disease, or prevention of the development of symptoms of that infection or disease; a delay in the onset of an infection or disease or its symptoms; or a decrease in the severity of a subsequently developed infection or disease or its symptoms.

As used herein an "effective dose" or "effective amount" refers to an amount of an immunogen sufficient to induce an immune response that reduces at least one symptom of malaria. An effective dose or effective amount may be determined e.g., by measuring amounts of neutralizing secretory and/or serum antibodies, e.g., by plaque neutralization, complement fixation, enzyme-linked immunosorbent (ELISA), or microneutralization assay.

As used herein, the term "vaccine" refers to a preparation including an immunogen (e.g. a fusion protein described herein) derived from a pathogen, which is used to induce an immune response against the pathogen that provides protective immunity (e.g., immunity that protects a subject against infection with the pathogen and/or reduces the severity of the disease or condition caused by infection with the pathogen). The protective immune response may include formation of antibodies and/or a cell-mediated response. Depending on context, the term "vaccine" may also refer to a suspension or solution of an immunogen that is administered to a vertebrate to produce protective immunity.

As used herein, the term "subject" includes humans and other animals. The subject, in one embodiment, is a human.

As used herein, the term "pharmaceutically acceptable" means being approved by a regulatory agency of the Federal or a state government or listed in the U.S. Pharmacopeia, European Pharmacopeia or other generally recognized pharmacopeia for use in mammals, and more particularly in humans. These compositions can be useful as a vaccine and/or antigenic compositions for inducing a protective immune response in a vertebrate.

As used herein, the term "about" means plus or minus 10% of the indicated numerical value.

Overview

The present disclosure provides methods and compositions for achieving high expression of large proteins, particularly multivalent proteins containing multiple antigens, from insect cells. The production of high levels of proteins as disclosed herein is particularly unexpected in view of prior experiences in the field.

Multivalent Proteins

The multivalent (the multivalent protein may also be referred to herein as a multimer) proteins disclosed herein can protect against multiple pathogens and/or the effects from multiple pathogenic proteins from the same organism. For example, certain pathogens may produce multiple molecules that each negatively affects a subject. A more effective response is produced by inducing responses against multiple separate antigens.

The proteins multivalent protein contains protein portions from multiple bacterial toxins the In some aspects, the multivalent protein comprises, or consists of, portions of proteins from the same organism, such as toxins for example. In other aspects, the multivalent protein comprises, or consists of, proteins from more than one organism. In particular aspects, no two proteins of a multivalent protein are from the same organism. In some aspects, the same proteins from different strains (i.e., isologs) may be used to produce the portion. Using the same protein from a different strain allows protection against multiple strains and is particularly useful in situations where virulent strains newly arise. Other examples include *C. botulinum*, which has 8 serological types, A through H. The methods and compositions disclosed herein can be used to provide a single vaccine against all 8 serotypes. Other particular examples include combination toxin vaccines to protect against cholera, diptheria and *shigella*, or tetanus, purtussis and diptheria. Thus, in some aspects, a multimeric protein may contain portions from 2, 3, 4, 5, 6, 7, 8, 9, or 10 different proteins. The portions may be used as components to produce the multimeric immunogenic polypeptides.

Exemplary multimers and components used to produce vaccines are described in the table below. Nucleic acid sequences encoding Q-toxin and BV1512, as well as alternative nucleic acid sequences for BV1420 and BV1470, are those using standard codon conversion appropriate degenerate codons that encode the indicated amino acid.

| Vaccine Construct | Components | Protein Sequence | Nucleic Acid Sequence |
| --- | --- | --- | --- |
| BV1420 | CDTb | SEQ ID NO: 10 | SEQ ID NO: 14 |
| (SEQ ID NO: 9; | TcdB | SEQ ID NO: 11 | SEQ ID NO: 15 |
| SEQ ID NO: 13) | TcdA | SEQ ID NO: 12 | SEQ ID NO: 16 |
| BV1470 | CDTb | SEQ ID NO: 2 | SEQ ID NO: 6 |
| (SEQ ID NO: 1; | TcdB | SEQ ID NO: 3 | SEQ ID NO: 7 |
| SEQ ID NO: 5) | TcdA | SEQ ID NO: 4 | SEQ ID NO: 8 |
| BV1512 | CDTb | SEQ ID NO: 18 | |
| (SEQ ID NO: 17) | TD | SEQ ID NO: 19 | |
| | TcdAR19 | SEQ ID NO: 20 | |
| Q-toxin | CDTb | SEQ ID NO: 22 | |
| (SEQ ID NO: 21) | TcdB003 | SEQ ID NO: 23 | |
| | TcdA | SEQ ID NO: 24 | |
| | TcdB027 | SEQ ID NO: 25 | |

Additional vaccine constructs may use the various components above in different orientations. In addition, proteins having at least 90% identity to each of these disclosed sequences may be used as components to produce a multimer protein.

Linkers

In some aspects, linkers may be used between one or more proteins in the multivalent proteins. In some aspects, the linker is a poly-(Gly)n linker, wherein n is 1, 2, 3, 4, 5, 6, 7, 8, 9, 10, 15, 16, 17, 18, 19, or 20. In other aspects, the linker is GG, GGG, or GGGG (SEQ ID NO: 26). In yet other aspects, the linker is selected from the group consisting of: dipeptides, tripeptides, and quadripeptides. Preferred dipeptides are Alanine-Serine (AS), Leucine-Glutamic acid (LE), Serine-Arginine (SR).

Multivalent antigens are particularly suited for protection against organisms that release multiple toxins into a subject. For example, bacteria are known to produce toxins that cause disease in humans. Thus, while the primary focus of the disclosure is C. difficile; the multimeric polypeptides of the disclosure may be prepared using portions of protein toxins from other species.

Toxin-producing species include C. perfringes, C. botulinum, C. difficile, and C. tetani), Bacillus (e.g., B. anthracis), Vibrio (e.g., Vibrio cholerae), Shigella, and Corynebacterium. C. difficile releases two enteric toxins, A and B, which are produced by toxigenic strains. Toxin A is an enterotoxin with minimal cytotoxic activity, whereas toxin B is a potent cytotoxin but has limited enterotoxic activity. A third toxin, Binary Toxin, also known as CDT, is also produced by the bacteria. Sequences encoding toxin A and B are known (Moncrief et al., Infect. Immun. 65:1105-1108 (1997); Barroso et al., Nucl. Acids Res. 18:4004 (1990); Dove et al. Infect. Immun. 58:480-488 (1990)). Sequences encoding Binary Toxin are also known (Accession Nos. ABS57477, AAB67305, AAF81761).

The usefulness of the present disclosure for protection against pathogen infection is illustrated by a trivalent protein vaccine against C. difficile. FIG. 1 shows the structure of two exemplary multimer proteins (BV1420 and BV1470). Each multimer contains portions of three toxin proteins, Toxin A (TcdA), Toxin B (TcdB), and binary toxin (CDTb), from C. difficile. Triple toxin 1420 also contains a furin cleavage site. These proteins are large-over 1800 amino acids—and would not be previously have been expected to yield usable amounts of protein when expressed in insect cells. Surprisingly, however, both proteins are expressed at high levels. See FIG. 3. Indeed, as FIG. 5 demonstrates, the yield for BV1470 was 269 mg/L. Similarly, the yield for BV1420 was 166 mg/L.

Analysis of the purified multimer proteins confirmed they were in nanoparticle structures with peak diameters around about 16 nm for BV1420 and about 18 nm for BV1470. Notably, the distribution of diameters shown in FIGS. 7 and 8 illustrates that a high percentage of the multimer proteins retained nanoparticle structure after purification.

Administering the BV1420 trivalent nanoparticles to mice demonstrates that immune responses to all three proteins were obtained. Moreover, as FIG. 13 illustrates the immune response obtained protected 100% of mice from lethal challenge with Toxin A and Binary toxin, as well as 67% to 83% of mice in response to lethal challenge with Toxin B. In contrast, mice in the PBS control group all died, with the exception of two mice in the binary toxin control group.

Quadrivalent toxins are also a preferred type of multimer immunogenic peptide. FIG. 20 shows two illustrative examples with four portions or components arranged in sequence. Despite the substantial length of the multimer, good protein production was obtained. FIG. 22.

Figure 23:
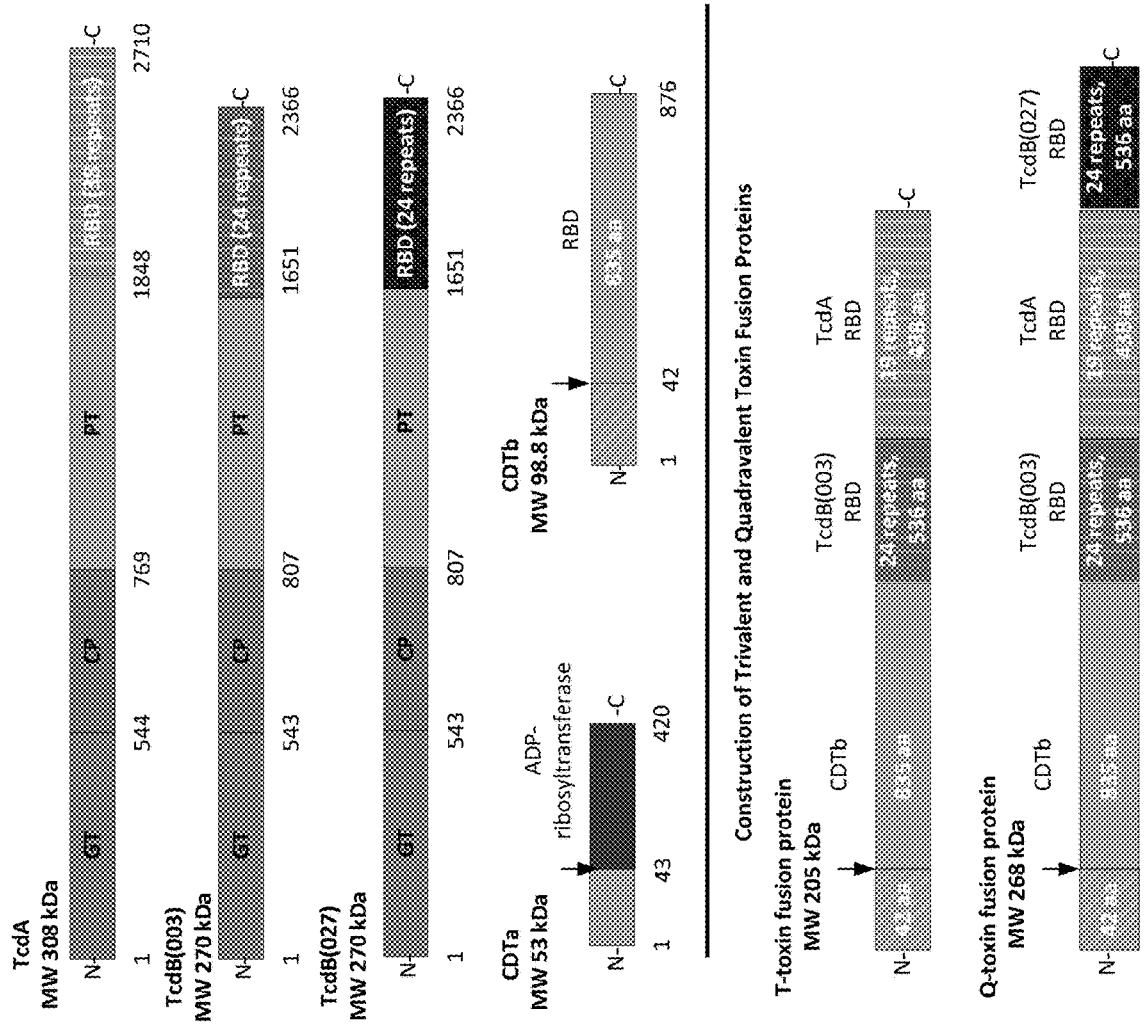
FIG. 23. *C. difficile* Toxins and Design of Chimeric Trivalent (T) and Quadrivalent (Q) Toxin Fusion Proteins.

FIG. 23 illustrates the conversion of a tri-toxin fusion protein to a quadrivalent toxin by addition of portion of a toxin from a second TcdB type. Comparing these two proteins shows that insect cell expression is able to give high level production. See FIG. 24A-D.

Thus, exemplary multimers include portions organized in various orientation. For example, starting from the N-terminus the first portion may be a TcdA portion, a TcdB portion or a CDTb portion. The second portion may be a TcdA portion, a TcdB portion or a CDTb portion. The third portion may be a TcdA portion, a TcdB portion or a CDTb portion. The fourth portion, if present, may be a TcdA portion, a TcdB portion or a CDTb portion. Thus, each portion may occupy each position. Typically, though not always, two adjacent portions are not portions from the same type of toxin. In preferred embodiments, the N-terminal portion is a a CDTb portion.

Molecular Biology Techniques

The multivalent proteins disclosed herein are prepared through molecular biology approaches. General texts which describe molecular biological techniques, which are applicable to the present invention, such as cloning, mutation, cell culture and the like, include Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (3rd Ed.), Vol. 1-3, Cold Spring Harbor Laboratory, Cold Spring Harbor, N.Y., 2000 ("Sambrook") and Current Protocols in Molecular Biology, F. M. Ausubel et al., eds., Current Protocols, a joint venture between Greene Publishing Associates, Inc. and John Wiley & Sons, Inc., ("Ausubel"). These texts describe mutagenesis, the use of vectors, promoters and many other relevant topics related to, e.g., the cloning and mutating PfCSP, etc. Thus, the invention also encompasses using known methods of protein engineering and recombinant DNA technology to improve or alter the characteristics of the proteins expressed on or in the fusion proteins of the invention. Various types of mutagenesis can be used to produce and/or isolate variant nucleic acids that encode for protein molecules and/or to further modify/mutate the proteins in or on the fusion proteins of the invention. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

Methods of cloning the proteins are known in the art. A gene can be cloned as a DNA insert into a vector. The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids or bacmids.

Thus, the invention comprises nucleotides that encode proteins, including chimeric molecules, cloned into an expression vector that can be expressed in a cell that induces the formation of fusion proteins of the invention. An "expression vector" is a vector, such as a plasmid, that is capable of promoting expression, as well as replication of a nucleic acid incorporated therein. Typically, the nucleic acid to be expressed is "operably linked" to a promoter and/or enhancer, and is subject to transcription regulatory control by the promoter and/or enhancer. In one embodiment, the nucleotides encode for a *Plasmodium* protein (as discussed above). In another embodiment, the expression vector is a baculovirus vector.

In some embodiments of the invention, proteins may comprise mutations containing alterations which produce silent substitutions, additions, or deletions, e.g., to optimize codon expression for a particular host (change codons in the human mRNA to those preferred by insect cells such as Sf9 cells). See, for example, U.S. Patent Publication 2005/0118191, herein incorporated by reference in its entirety for all purposes.

In addition, the nucleotides can be sequenced to ensure that the correct coding regions were cloned and do not contain any unwanted mutations. The nucleotides can be subcloned into an expression vector (e.g. baculovirus) for expression in any cell. The above is only one example of how the proteins can be cloned. A person with skill in the art understands that additional methods may be used.

Host Cells

The high level expression was obtained in insect cell expression systems. Non limiting examples of insect cells are, *Spodoptera frugiperda* (Sf) cells, e.g. Sf9, Sf21, *Trichoplusia ni* cells, e.g. High Five cells, and *Drosophila* S2 cells.

Vectors, e.g., vectors comprising polynucleotides that encode fusion proteins, can be transfected into host cells according to methods well known in the art. For example, introducing nucleic acids into eukaryotic cells can be achieved by calcium phosphate co-precipitation, electroporation, microinjection, lipofection, and transfection employing polyamine transfection reagents. In one embodiment, the vector is a recombinant baculovirus.

Nanoparticle Production

The nanoparticles may be produced by growing host cells transformed by an expression vector under conditions whereby the recombinant proteins are expressed. In one aspect, a method of producing a multivalent protein comprises transfecting vectors encoding the protein into a suitable host cell and expressing the protein under conditions that allow nanoparticle formation. In another embodiment, the eukaryotic cell is selected from the group consisting of yeast, insect, amphibian, avian or mammalian cells. The selection of the appropriate growth conditions is within the skill or a person with skill of one of ordinary skill in the art.

Methods to grow host cells include, but are not limited to, batch, batch-fed, continuous and perfusion cell culture techniques. Cell culture means the growth and propagation of cells in a bioreactor (a fermentation chamber) where cells propagate and express protein (e.g. recombinant proteins) for purification and isolation. Typically, cell culture is performed under sterile, controlled temperature and atmospheric conditions in a bioreactor. A bioreactor is a chamber used to culture cells in which environmental conditions such as temperature, atmosphere, agitation and/or pH can be monitored. In one embodiment, the bioreactor is a stainless steel chamber. In another embodiment, the bioreactor is a pre-sterilized plastic bag (e.g. Cellbag®, Wave Biotech, Bridgewater, N.J.). In other embodiment, the pre-sterilized plastic bags are about 50 L to 1000 L bags.

Detergent Extraction and Purification of Nanoparticles

The nanoparticles may be harvested from the host cells using detergents. Suitable detergents include non-ionic surfactants. For example, the non-ionic surfactant may be Bis(polyethylene glycol bis[imidazoylcarbonyl]), nonoxynol-9, Bis(polyethylene glycol bis[imidazoyl carbonyl]), Brij® 35, Brij® 56, Brij® 72, Brij® 76, Brij® 92V, Brij® 97, Brij® 58P, Cremophor® EL, Decaethyleneglycol monododecyl ether, N-Decanoyl-N-methylglucamine, n-Decyl alpha-Dglucopyranoside, Decyl beta-D-maltopyranoside, n-Dodecanoyl-N-methylglucamide, nDodecyl alpha-D-maltoside, n-Dodecyl beta-D-maltoside, n-Dodecyl beta-D-maltoside, Heptaethylene glycol monodecyl ether, Heptaethylene glycol monododecyl ether, Heptaethylene glycol monotetradecyl ether, n-Hexadecyl beta-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-0-(N-heptylcarbamoyl)-alpha-D-glucopyranoside, Nonaethylene glycol monododecyl ether, N-Nonanoyl-N-methylglucamine, N-NonanoylN-methylglucamine, Octaethylene glycol monodecyl ether, Octaethylene glycolmonododecyl ether, Octaethylene glycol monohexadecyl ether, Octaethylene glycol monooctadecyl ether, Octaethylene glycol monotetradecyl ether, Octyl-beta-D glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis(imidazolyl carbonyl), Polyoxyethylene 25 propylene glycol stearate, Saponin from *Quillaja* bark, Span® 20, Span® 40, Span® 60, Span® 65, Span® 80, Span® 85, Tergitol Type 15-S-12, Tergitol Type 15-S-30, Tergitol Type 15-S-5, Tergitol Type 15-S-7, Tergitol Type 15-S-9, Tergitol Type NP-10, Tergitol Type NP-4, Tergitol Type NP-40, Tergitol, Type NP-7 Tergitol Type NP-9, Tergitol Type TMN-10, Tergitol Type TMN-6, Tetradecyl-beta-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton CF-21, Triton CF-32, Triton DF-12, Triton DF-16, Triton GR-5M, Triton QS-15, Triton QS-44, Triton X-100, Triton X-102, Triton X-15, Triton X-151, Triton X-200, Triton X-207, Triton® X-100, Triton® X-114, Triton® X-165, Triton® X-305, Triton® X-405, Triton® X-45, Triton® X-705-70, TWEEN® 20, TWEEN® 21, TWEEN® 40, TWEEN® 60, TWEEN® 61, TWEEN® 65, TWEEN® 80, TWEEN® 81, TWEEN® 85, Tyloxapol, n-Undecyl beta-D-glucopyranoside, semi-synthetic derivatives thereof, or combinations thereof. Tergitol NP-9 is a preferred detergent.

Once the host cells have grown for 48 to 72 hours, the cells are isolated from the media and a detergent-containing solution is added to solubilize the cell membrane, releasing the nanoparticles in a detergent extract. The detergent may be added to a final concentration of about 0.1% to about 1.0%. For example, the concentration may be about 0.1%, about 0.2%, about 0.3%, about 0.5%, about 0.7%, about 0.8%, or about 1.0%. In certain aspects, the range may be about 0.1% to about 0.3%. Preferably, the concentration is about 0.2%.

The nanoparticles may then be isolated using methods that preserve the integrity thereof, such as centrifugation. In some aspects, gradient centrifugation, such as using cesium chloride, sucrose and iodixanol, may be used. Other techniques may be used as alternatives or in addition, such as standard purification techniques including, e.g., ion exchange and gel filtration chromatography.

In one aspect, the detergent extract is added to multiple columns sequentially. For example, the first column may be an ion chromatography column, such as TMAE, the second column may be a hydrophobic interaction column, such as Phenyl HP, and the third column may be a strong anion exchange column such as a Source 30Q column. Increased purity may be obtained by repeating the three-step procedure.

The following provides a general procedure for making isolating and purifying proteins. A person of skill in the art would understand that there variations that can be utilized Production is initiated by seeding Sf9 cells (non-infected) into shaker flasks, allowing the cells to expand and scaling up as the cells grow and multiply (for example from a 125-ml flask to a 50 L Wave bag). The medium used to grow the cell is formulated for the appropriate cell line (preferably serum free media, e.g. insect medium ExCell-420, JRH). Next, the cells are infected with recombinant baculovirus at the most efficient multiplicity of infection (e.g. from about 1 to about 3 plaque forming units per cell). Once infection has occurred, the fusion proteins (and, optionally, other immunogens) are expressed from the virus genome. Usually, infection is most efficient when the cells are in mid-log phase of growth ($4\text{-}8\times10^6$ cells/ml) and are at least about 90% viable.

Proteins of the disclosure can be harvested approximately 48 to 96 hours post infection. In some aspects, harvesting takes place at about 48 hours, about 72 hours, or between about 48 and about 72 hours. Typically, harvesting takes place when the levels of VLPs in the cell culture medium are near the maximum but before extensive cell lysis. The Sf9 cell density and viability at the time of harvest can be about $0.5\times10^6$ cells/ml to about $1.5\times10^6$ cells/ml with at least 20% viability, as shown by dye exclusion assay.

To solubilize the particles, directly add Tergitol NP9 to cell culture to final concentration of 0.2% NP9/25 mM Tris/50 mM NaCl/pH8.0. Incubate at room temperature for 1 hour then centrifuge the lysate at 9000 g for 30 min twice. Collected the supernatant containing the nanoparticles. The supernatant is then added to in Buffer A and eluted in Buffer B (Buffer A: 25 mM Tris pH 8.0/50 mM NaCl Buffer B: 25 mM Tris pH 8.0/1M NaCl). The eluate is applied to Phenyl HP columns (Buffer A: 350 mM Na-Citrate/25 mM Tris pH7.5 and Buffer B: 5 mM Tris pH8.0) and then to a Source 30Q column (Buffer A: 25 mM Tris pH8.0/250 mM NaCl Buffer B: 25 mM Tris pH8.0/IM NaCl). The pooled fractions containing the product are passed through a 2 micron filter. See FIGS. 8-10.

The procedures described above enable a purity of at least about 90%, at least about 95% or about 98% at a yield of 150 mg/L to about 300 mg/L. Purity may be measured by gel-based approaches that indicate total protein.

The intact baculovirus can be inactivated, if desired. Inactivation can be accomplished by chemical methods, for example, formalin or R-propiolactone (BPL). Removal and/or inactivation of intact baculovirus can also be largely accomplished by using selective precipitation and chromatographic methods known in the art, as exemplified above. Methods of inactivation comprise incubating the sample containing the VLPs in 0.2% of BPL for 3 hours at about 25° C. to about 27° C. The baculovirus can also be inactivated by incubating the sample containing the VLPs at 0.05% BPL at 4° C. for 3 days, then at 37° C. for one hour.

The above techniques can be practiced across a variety of scales. For example, T-flasks, shake-flasks, spinner bottles, up to industrial sized bioreactors. The bioreactors can comprise either a stainless steel tank or a pre-sterilized plastic bag (for example, the system sold by Wave Biotech, Bridgewater, N.J.). A person with skill in the art will know what is most desirable for the particular circumstance.

Protein Size and Yield

The yield for the multimer proteins using the methods disclosed herein is remarkable. In some cases, the yield is about 150 mg/L to about 300 mg/L. In some embodiments, the yield is about 40 mg/L, about 60 mg/L, about 80 mg/L, about 100 mg/L, about 150 mg/L, about 200 mg/L, about 250 mg/L, or about 300 mg/L. In particular aspects, the yield ranges from about 40 mg/L to about 300 mg/L, from about 80 mg/L to about 250 mg/L, or about 100 mg/mL to about 300 mg/L.

Large multimer proteins disclosed herein typically range from about 1500-2500 amino acids. In some aspects, they range from about 1500 to about 2000 amino acids. In other aspects, they range from about 1800 to about 2000 amino acids.

Figure 9D:
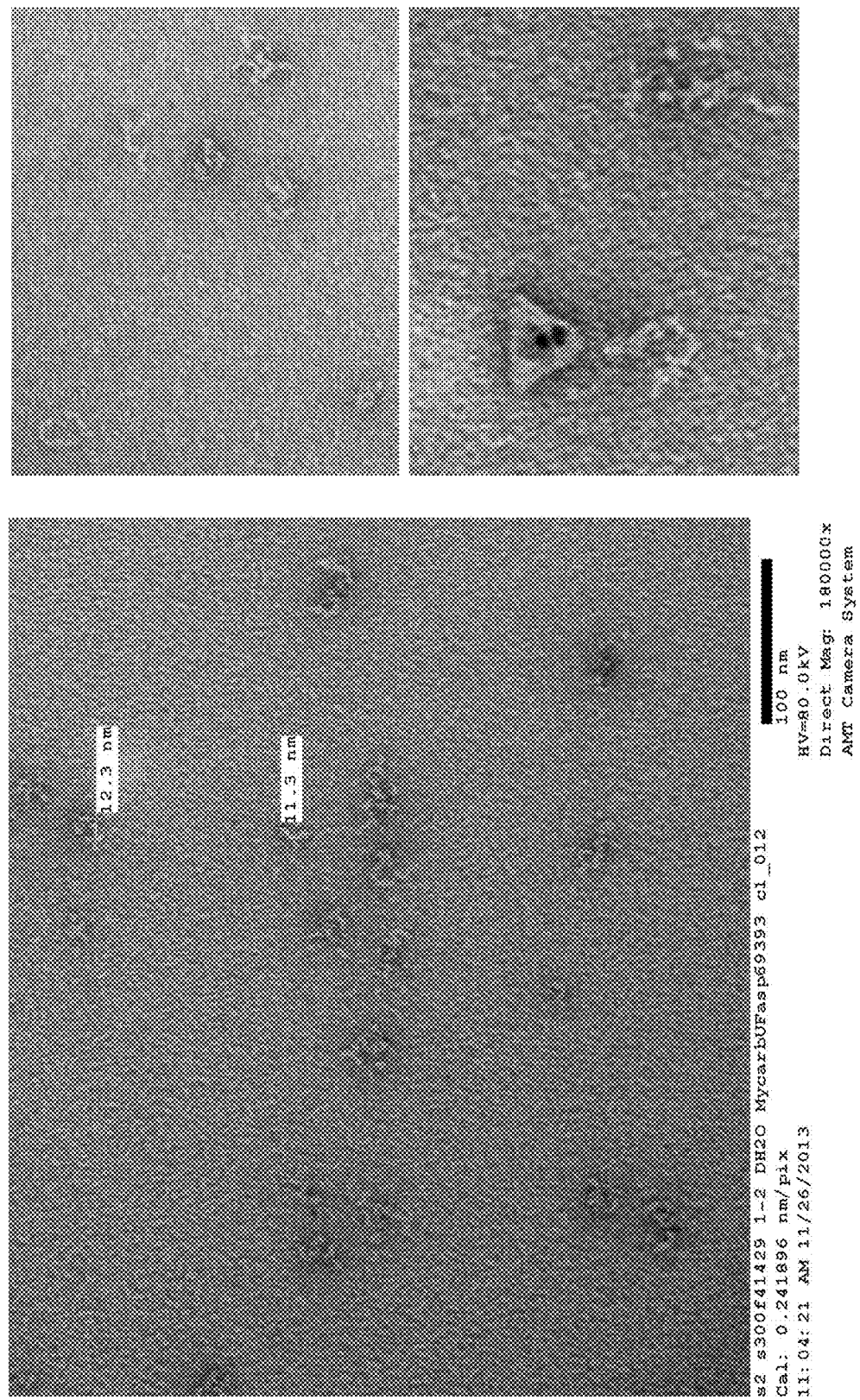

The multimer proteins form nanoparticles having a typical diameter of about 11 nm to about 35 nm. The diameter range may be about 15 nm to about 25 nm. Illustrative examples of multimer protein nanoparticles in these ranges are shown in FIG. 9.

Importantly, even though the proteins are large, they remain soluble. For example, the purified multimer protein may be about 80% soluble, about 85% soluble, about 90% soluble, about 95% soluble, about 97% soluble, or about 99% soluble. In some aspects, solubility is about 90°/to about 99% or about 90% to about 95%.

Modified Antigens and Polypeptides

The antigens disclosed herein encompass variations and mutants of those antigens. In certain aspects, the antigen may share identity to a disclosed antigen. Generally, and unless specifically defined in context of a specifically identified antigens, the percentage identity may be at least 80%, at least 90%, at least 95%, at least 97%, or at least 98%. Percentage identity can be calculated using the alignment program Clustal Omega, available at www.ebi.ac.uk/Tools/msa/clustalo using default parameters.

In particular aspects, the protein contained in the nanoparticles consists of that protein. In other aspects, the protein contained in the nanoparticles comprise that protein. Extensions to the protein itself may be for various purposes.

In some aspects, the antigen may be extended at the N-terminus, the C-terminus, or both. In some aspects, the extension is a tag useful for a function, such as purification or detection. In some aspects the tag contains an epitope. For example, the tag may be a polyglutamate tag, a FLAG-tag, a HA-tag, a polyHis-tag (having about 5-10 histidines), a Myc-tag, a Glutathione-S-transferase-tag, a Green fluorescent protein-tag, Maltose binding protein-tag, a Thioredoxin-tag, or an Fc-tag. In other aspects, the extension may be an N-terminal signal peptide fused to the protein to enhance expression. While such signal peptides are often cleaved during expression in the cell, some nanoparticles may contain the antigen with an intact signal peptide. Thus, when a nanoparticle comprises an antigen, the antigen may contain an extension and thus may be a fusion protein when incorporated into nanoparticles. For the purposes of calculating identity to the sequence, extensions are not included. In some aspects, the antigen may be truncated. For example, the N-terminus may be truncated by about 10 amino acids, about 30 amino acids, about 50 amino acids, about 75 amino acids, about 100 amino acids, or about 200 amino acids. For example, the C-terminus may be truncated by about 10 amino acids, about 30 amino acids, about 50 amino acids, about 75 amino acids, about 100 amino acids, or about 200 amino acids.

Pharmaceutical Compositions

The pharmaceutical compositions disclosed herein comprise a multimer protein and a pharmaceutically acceptable carrier. Pharmaceutically acceptable carriers include any pharmaceutical agent that can be administered to a subject without undue toxicity, irritation, or allergic reaction. Pharmaceutically acceptable carriers may also include one or more pharmaceutically acceptable excipient. A pharmaceutically acceptable excipient is any excipient that is useful in preparing a pharmaceutical composition that is generally safe and non-toxic, and is acceptable for veterinary as well as human pharmaceutical use.

The pharmaceutical compositions useful herein contain a pharmaceutically acceptable carrier, including any suitable diluent or excipient, which includes any pharmaceutical agent that does not itself induce the production of an immune response harmful to the vertebrate receiving the composition, and which may be administered without undue toxicity and an immunogen; for example a multimer fusion protein.

In some aspects, formulations may include a pharmaceutically acceptable carrier or excipient. Pharmaceutically acceptable carriers include but are not limited to saline, buffered saline, dextrose, water, glycerol, sterile isotonic aqueous buffer, and combinations thereof. A thorough discussion of pharmaceutically acceptable carriers, diluents, and other excipients is presented in Remington's Pharmaceutical Sciences (Mack Pub. Co. N.J. current edition). The formulation may be adapted to suit the mode of administration. In an exemplary embodiment, the formulation is suitable for administration to humans, is sterile, non-particulate and/or non-pyrogenic.

The composition may also contain wetting agents, or emulsifying agents, or pH buffering agents, or mixtures thereof. The composition can be a solid form, such as a lyophilized powder suitable for reconstitution (e.g., with water or saline), a liquid solution, suspension, emulsion, tablet, pill, capsule, sustained release formulation, or powder. Oral formulations may include standard carriers such as pharmaceutical grades of mannitol, lactose, starch, magnesium stearate, sodium saccharine, cellulose, magnesium carbonate, etc.

Adjuvants

The immunogenicity of a particular composition may be enhanced by the use of non-specific stimulators of the immune response, known as adjuvants. Adjuvants have been used experimentally to promote a generalized increase in immunity against antigens (e.g., U.S. Pat. No. 4,877,611). Immunization protocols have used adjuvants to stimulate responses for many years, and as such, adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation. The inclusion of any adjuvant described in Vogel et al., "A Compendium of Vaccine Adjuvants and Excipients (2nd Edition)," herein incorporated by reference in its entirety for all purposes, is envisioned within the scope of this disclosure.

Exemplary adjuvants include complete Freund's adjuvant (a non-specific stimulator of the immune response containing killed *Mycobacterium tuberculosis*), incomplete Freund's adjuvants and aluminum hydroxide adjuvant. Other adjuvants comprise GMCSP, BCG, MDP compounds, such as thur-MDP and nor-MDP, CGP (MTP-PE), lipid A, and monophosphoryl lipid A (MPL), MF-59, RIBI, which contains three components extracted from bacteria, MPL, trehalose dimycolate (TDM) and cell wall skeleton (CWS) in a 2% squalene/Tween® 80 emulsion. In other preferred aspects, Alum such as 2% Alhydrogel ($Al(OH)_3$) is used. In some aspects, the adjuvant may be a paucilamellar lipid vesicle; for example, Novasomes®. Novasomes® are paucilamellar nonphospholipid vesicles ranging from about 100 nm to about 500 nm. They comprise Brij 72, cholesterol, oleic acid and squalene. Novasomes have been shown to be an effective adjuvant (see, U.S. Pat. Nos. 5,629,021, 6,387, 373, and 4,911,928.

Saponin Adjuvants

Adjuvants containing saponin may also be combined with the immunogens disclosed herein. Saponins are glycosides derived from the bark of the *Quillaja saponaria* Molina tree. Typically, saponin is prepared using a multi-step purification process resulting in multiple fractions. As used, herein, the term "a saponin fraction from *Quillaja saponaria* Molina" is used generically to describe a semi-purified or defined saponin fraction of *Quillaja saponaria* or a substantially pure fraction thereof.

Saponin Fractions

Several approaches for producing saponin fractions are suitable. Fractions A, B, and C are described in U.S. Pat. No. 6,352,697 and may be prepared as follows. A lipophilic fraction from Quil A, a crude aqueous *Quillaja saponaria* Molina extract, is separated by chromatography and eluted with 70% acetonitrile in water to recover the lipophilic fraction. This lipophilic fraction is then separated by semi-preparative HPLC with elution using a gradient of from 25% to 60% acetonitrile in acidic water. The fraction referred to herein as "Fraction A" or "QH-A" is, or corresponds to, the fraction, which is eluted at approximately 39% acetonitrile. The fraction referred to herein as "Fraction B" or "QH-B" is, or corresponds to, the fraction, which is eluted at approximately 47% acetonitrile. The fraction referred to herein as "Fraction C" or "QH-C" is, or corresponds to, the fraction, which is eluted at approximately 49% acetonitrile. Additional information regarding purification of Fractions is found in U.S. Pat. No. 5,057,540. When prepared as described herein, Fractions A, B and C of *Quillaja saponaria* Molina each represent groups or families of chemically closely related molecules with definable properties. The chromatographic conditions under which they are obtained are such that the batch-to-batch reproducibility in terms of elution profile and biological activity is highly consistent.

Other saponin fractions have been described. Fractions B3, B4 and B4b are described in EP 0436620. Fractions QA1-QA22 are described EP03632279 B2, Q-VAC (Nor-Feed, AS Denmark), *Quillaja saponaria* Molina Spikoside (Isconova AB, Ultunaallén 2B, 756 51 Uppsala, Sweden). Fractions QA-1, QA-2, QA-3, QA-4, QA-5, QA-6, QA-7, QA-8, QA-9, QA-10, QA-11, QA-12, QA-13, QA-14, QA-15, QA-16, QA-17, QA-18, QA-19, QA-20, QA-21, and QA-22 of EP 0 3632 279 B2, especially QA-7, QA-17, QA-18, and QA-21 may be used. They are obtained as described in EP 0 3632 279 B2, especially at page 6 and in Example 1 on page 8 and 9.

The saponin fractions described herein and used for forming adjuvants are often substantially pure fractions; that is, the fractions are substantially free of the presence of contamination from other materials. In particular aspects, a substantially pure saponin fraction may contain up to 40% by weight, up to 30% by weight, up to 25% by weight, up to 20% by weight, up to 15% by weight, up to 10% by weight, up to 7% by weight, up to 5% by weight, up to 2% by weight, up to 1% by weight, up to 0.5% by weight, or up to 0.1% by weight of other compounds such as other saponins or other adjuvant materials.

ISCOM Structures

Saponin fractions may be administered in the form of a cage-like particle referred to as an ISCOM (Immune Stimulating COMplex). ISCOMs may be prepared as described in EP0109942B1, EP0242380B1 and EP0180546 B1. In particular embodiments a transport and/or a passenger antigen may be used, as described in EP 9600647-3 (PCT/SE97/00289).

Matrix Adjuvant

In some aspects, the ISCOM is an ISCOM matrix complex. An ISCOM matrix complex comprises at least one saponin fraction and a lipid. The lipid is at least a sterol, such as cholesterol. In particular aspects, the ISCOM matrix complex also contains a phospholipid. The ISCOM matrix complexes may also contain one or more other immunomodulatory (adjuvant-active) substances, not necessarily a glycoside, and may be produced as described in EP0436620B1.

In other aspects, the ISCOM is an ISCOM complex. An ISCOM complex contains at least one saponin, at least one lipid, and at least one kind of antigen or epitope. The ISCOM complex contains antigen associated by detergent treatment such that that a portion of the antigen integrates into the particle. In contrast, ISCOM matrix is formulated as an admixture with antigen and the association between ISCOM matrix particles and antigen is mediated by electrostatic and/or hydrophobic interactions.

According to one embodiment, the saponin fraction integrated into an ISCOM matrix complex or an ISCOM complex, or at least one additional adjuvant, which also is integrated into the ISCOM or ISCOM matrix complex or mixed therewith, is selected from fraction A, fraction B, or fraction C of *Quillaja saponaria*, a semipurified preparation of *Quillaja saponaria*, a purified preparation of *Quillaja saponaria*, or any purified sub-fraction e.g., QA 1-21.

In particular aspects, each ISCOM particle may contain at least two saponin fractions. Any combinations of weight % of different saponin fractions may be used. Any combination of weight % of any two fractions may be used. For example, the particle may contain any weight % of fraction A and any weight % of another saponin fraction, such as a crude saponin fraction or fraction C, respectively. Accordingly, in particular aspects, each ISCOM matrix particle or each ISCOM complex particle may contain from 0.1 to 99.9 by weight, 5 to 95% by weight, 10 to 90% by weight 15 to 85% by weight, 20 to 80% by weight, 25 to 75% by weight, 30 to 70% by weight, 35 to 65% by weight, 40 to 60% by weight, 45 to 55% by weight, 40 to 60% by weight, or 50% by weight of one saponin fraction, e.g. fraction A and the rest up to 100% in each case of another saponin e.g. any crude fraction or any other faction e.g. fraction C. The weight is calculated as the total weight of the saponin fractions. Examples of ISCOM matrix complex and ISCOM complex adjuvants are disclosed in U.S. Published Application No. 2013/0129770.

In particular embodiments, the ISCOM matrix or ISCOM complex comprises from 5-99% by weight of one fraction, e.g. fraction A and the rest up to 100% of weight of another fraction e.g. a crude saponin fraction or fraction C. The weight is calculated as the total weight of the saponin fractions.

In another embodiment, the ISCOM matrix or ISCOM complex comprises from 40% to 99% by weight of one fraction, e.g. fraction A and from 1% to 60% by weight of another fraction, e.g. a crude saponin fraction or fraction C. The weight is calculated as the total weight of the saponin fractions.

In yet another embodiment, the ISCOM matrix or ISCOM complex comprises from 70% to 95% by weight of one fraction e.g., fraction A, and from 30% to 5% by weight of another fraction, e.g., a crude saponin fraction, or fraction C. The weight is calculated as the total weight of the saponin fractions. In other embodiments, the saponin fraction from *Quillaja saponaria* Molina is selected from any one of QA 1-21.

In addition to particles containing mixtures of saponin fractions, ISCOM matrix particles and ISCOM complex particles may each be formed using only one saponin fraction. Compositions disclosed herein may contain multiple particles wherein each particle contains only one saponin fraction. That is, certain compositions may contain one or more different types of ISCOM-matrix complexes particles and/or one or more different types of ISCOM complexes particles, where each individual particle contains one saponin fraction from *Quillaja saponaria* Molina, wherein the saponin fraction in one complex is different from the saponin fraction in the other complex particles.

In particular aspects, one type of saponin fraction or a crude saponin fraction may be integrated into one ISCOM matrix complex or particle and another type of substantially pure saponin fraction, or a crude saponin fraction, may be integrated into another ISCOM matrix complex or particle. A composition or vaccine may comprise at least two types of complexes or particles each type having one type of saponins integrated into physically different particles.

In the compositions, mixtures of ISCOM matrix complex particles and/or ISCOM complex particles may be used in which one saponin fraction *Quillaja saponaria* Molina and another saponin fraction *Quillaja saponaria* Molina are separately incorporated into different ISCOM matrix complex particles and/or ISCOM complex particles.

The ISCOM matrix or ISCOM complex particles, which each have one saponin fraction, may be present in composition at any combination of weight %. In particular aspects, a composition may contain 0.1% to 99.9% by weight, 5% to 95% by weight, 10% to 90% by weight, 15% to 85% by weight, 20% to 80% by weight, 25% to 75% by weight, 30% to 70% by weight, 35% to 65% by weight, 40% to 60% by weight, 45% to 55% by weight, 40 to 60% by weight, or 50% by weight, of an ISCOM matrix or complex containing a first saponin fraction with the remaining portion made up by an ISCOM matrix or complex containing a different saponin fraction. In some aspects, the remaining portion is one or more ISCOM matrix or complexes where each matrix or complex particle contains only one saponin fraction. In other aspects, the ISCOM matrix or complex particles may contain more than one saponin fraction.

In preferred compositions, the saponin fraction in a first ISCOM matrix is Fraction A (a "Fraction A Matrix") and the saponin fraction in a second ISCOM matrix or ISCOM complex particle is Fraction C (a "Fraction C Matrix"). Thus, preferred compositions comprise, as an adjuvant, a Fraction A Matrix adjuvant and a Fraction C Matrix adjuvant. The amounts of each Matrix in the composition may vary. For example, the amount of Fraction A Matrix may be about 80% (w/w), about 85% (w/w), about 90% (w/w), about 92% (w/w), or about 95% (w/w) with the remainder Fraction C Matrix. A suitable example of a suitable 85:15 Fraction A Matrix and Fraction C Matrix combination is Matrix-M™ (Novavax AB, Uppsala, Sweden), a mixture of Fraction A Matrix and Fraction C Matrix at a ratio of about 85 to about 15.

Other saponin fractions, such as QS-7 and QS-21 fractions, their production and their use is described in U.S. Pat. Nos. 5,057,540; 6,231,859; 6,352,697; 6,524,584; 6,846,489; 7,776,343, and 8,173,141. These fractions may be used in the methods and compositions disclosed herein.

Immune Stimulators

Compositions of the disclosure may also be formulated with "immune stimulators." These are the body's own chemical messengers (cytokines) to increase the immune system's response.

Immune stimulators include, but are not limited to, various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CM); and other immunostimulatory molecules, such as macrophage inflammatory factor, Flt3 ligand, B7.1; B7.2, etc. The immunostimulatory molecules may be administered in the same formulation as the compositions of the disclosure, or may be administered separately. Either the protein or an expression vector encoding the protein may be administered to produce an immunostimulatory effect. Thus, in one embodiment, the disclosure comprises antigenic and vaccine formulations comprising an adjuvant and/or an immune stimulator.

Methods of Inducing Immune Responses

Also provided in the present disclosure are methods of eliciting an immune response against pathogens. The method involves administering an immunologically effective amount of a composition comprising a multimer protein to a subject. Administration of an immunologically effective amount of the composition of the disclosure elicits an immune response specific for epitopes present on the fusion protein. Such an immune response can include B cell responses and/or T cell responses. When administered to a subject, the multimer proteins preferably induce neutralizing antibodies. Preferably, the immune response includes elements that are specific for at least one conformational epitope present each protein contained in the multimer protein.

Administration

Administration may be by any suitable route. Suitable routes include parenteral administration (e.g., intradermal, intramuscular, intravenous and subcutaneous), epidural, and mucosal (e.g., intranasal and oral or pulmonary routes or by suppositories), transdermally or intradermally. Administration may be by infusion or bolus injection, by absorption through epithelial or mucocutaneous linings (e.g., oral mucous, colon, conjunctiva, nasopharynx, oropharynx, vagina, urethra, urinary bladder and intestinal mucosa, etc.) and may be administered together with other biologically active agents. In some aspects, intranasal or other mucosal routes of administration may result in an antibody or other immune response that is substantially higher than other routes of administration. Administration can be systemic or local.

In some aspects, administration may be by injection using a needle and syringe, by a needle-less injection device. In other aspects, administration is by drops, large particle aerosol (greater than about 10 microns), or by spray into the upper respiratory tract.

In some aspects, a pharmaceutical pack or kit comprising one or more containers filled with one or more of the components of the formulations is provided. In a particular aspect, the kit may include two containers, a first container containing a multimer protein, and a second container containing an adjuvant. Associated with such container(s) may be a notice in the form prescribed by a governmental agency regulating the manufacture, use or sale of pharmaceuticals or biological products, which notice reflects approval by the agency of manufacture, use or sale for human administration. Formulations may also be packaged in a hermetically sealed container such as an ampoule or sachette indicating the quantity of composition.

In some aspects, administration may be targeted. For example, the compositions may be administered in such a manner as to target mucosal tissues in order to elicit an immune response at the site of immunization. Mucosal tissues such as gut associated lymphoid tissue (GALT) can be targeted for immunization by using oral administration of compositions which contain adjuvants with particular mucosal targeting properties. Additional mucosal tissues can also be targeted, such as nasopharyngeal lymphoid tissue (NALT) and bronchial-associated lymphoid tissue (BALT).

In some aspects, multiple compositions may be administered each having different collections of antigens. Where more than one multimer protein is administered, the proteins may be co-administered simultaneously to the same position of the subject; for example, by injection of material from one or more containers containing multimer proteins. In other aspects, they may be co-administered sequentially at different sites within a short space of time; for example, one administration may be in the thigh, and a second administration may be in the arm, with both administrations occurring within a short period (e.g. up to 30 minutes).

Human clinical studies can be performed to determine the preferred effective dose for humans by a skilled artisan. Such clinical studies are routine and well known in the art. The precise dose to be employed will also depend on the route of administration. Effective doses may be extrapolated from dose-response curves derived from in vitro or in vivo test systems. Dose may be adjusted based on, e.g., age, physical condition, body weight, sex, diet, time of administration, and other clinical factors.

While stimulation of immunity with a single dose is possible, additional dosages may be administered, by the same or different route, to achieve the desired effect. In neonates and infants, for example, multiple administrations may be required to elicit sufficient levels of immunity. Administration can continue at intervals throughout childhood, as necessary to maintain sufficient levels of protection against infections. Similarly, adults who are particularly susceptible to repeated or serious infections, such as, for example, health care workers, day care workers, family members of young children, the elderly, and individuals with compromised cardiopulmonary function may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

The vaccine compositions may also be used for preparing antibodies against the toxins useful for passive administration therapies. See Casadevall. "Passive Antibody Administration (Immediate Immunity) as a Specific Defense Against Biological Weapons," *Emerging Infectious Diseases.* 2002; 8(8) 833-841.

EXAMPLES

Example 1

*C. difficile* Triple Toxin Vaccine Constructs

Two triple toxin vaccines were constructed. A diagram of the protein structures is shown in FIG. 1. Triple toxin 1420 (also referred to as BV1420) contains, from N-terminus to C-terminus, an Activation domain peptide, a mature CDTb peptide, a TcdB RBD peptide, and a TcdA RBD peptide containing 19 repeats (R19). A furin cleavage site (RARRRKKR; SEQ ID NO:27) was located between the activation domain and mature CDTb peptides. FIGS. 2 and 3 show the protein and genetic sequence of BV1470, respectively. Linker sites at either end of the TcdB peptide.

Example 2

Expression of Triple Toxin Vaccine

Sf9 cells were transformed with a baculovirus vector expressing the triple vaccine as a single transcript. Expression data from the Sf9 cells is shown in FIG. 2. FIG. 2 shows expression of each proteins harvested at 48 hours and at 72 hours. Remarkably, even though each protein is over 200 kDa, high level production is achieved. FIG. 7 shows a time course of expression from 48 hours to 96 hours. The data shows that, for both proteins, the protein is highly soluble.

Example 3

Purification of Triple Toxin Vaccine

To solubilize and purify the particles, Tergitol (NP9) was directly added to cell culture to final concentration of 0.2% NP9/25 mM Tris/50 mM NaCl/pH8.0. Incubate at room temperature for 1 hour then centrifuge the lysate at 9000 g for 30 min twice. Collected the supernatant containing the nanoparticles. The supernatant is then added to in Buffer A and eluted in Buffer B (Buffer A: 25 mM Tris pH 8.0/50 mM NaCl Buffer B: 25 mM Tris pH 8.0/1M NaCl). The eluate is applied to Phenyl HP columns (Buffer A: 350 mM Na-Citrate/25 mM Tris pH7.5 and Buffer B: 5 mM Tris pH8.0) and then to a Source 30Q column (Buffer A: 25 mM Tris pH8.0/250 mM NaCl Buffer B: 25 mM Tris pH8.0/1M NaCl). The pooled fractions containing the product are passed through a 2 micron filter. See FIGS. 4-6. Purification of 1470 from Sf9 yielded 269 mg/liter of protein. Purification of 1420 from Sf9 cells yielded 166 mg/liter.

Example 4

Analysis of Triple Toxin Vaccine Particles

Particle size distribution by volume graph for triple toxin BV1420 was analyzed by dynamic light scattering using a Zeta Sizer Nano. Graph of size distribution by volume is shown in FIG. 7. The average diameter was ~30 nm. FIG. 8 shows particle size distribution by intensity graph for triple toxin BV1470. The average diameter was ~18 nm.

FIG. 9 shows various electronmicrographs of negative stained triple toxin BV1420. Electron-micrograph of purified triple toxin BV1420 was diluted to approximately 10 ug/ml and negatively stained with uranyl acetate.

Example 5

*C. difficile* Triple Toxin Vaccine: Lethal Toxin Challenge and Animal Survival

FIG. 10 provides the results of a mouse trial of the Triple Toxin Vaccine against Toxin A and Binary Toxin. Groups 1-6 were administered BV1420 antigen (30 μg) or PBS as shown. Groups 1 and 4 contain 50 μg Alum OH; Groups 2 and 5 contained 50 μg Alum OH and 50 μg ISCOM Matrix M adjuvant. Mice were immunized at Day 0 and Day 14, with bleeds at Day 0, 14, and 32. Mice were challenged with Toxin A or Binary Toxin at Day 35.

FIG. 11 shows serum IgG responses. PBS did not induce antibodies, as expected. The Triple Toxin Vaccines, either with Alum OH or with both Alum OJ and Matrix M induced Titers ranging from about $10^4$ to about $10^6$ against Toxin A, Toxin B, and CDTb. FIG. 12 establishes that the antibodies neutralized both Toxin A and CTDb. FIG. 13 shows animal survival for the 6 groups. Groups 1, 2, 4, and 5 showed 100% survival. Except for two mice in the binary toxin challenge, all the animals in the control PBS groups died. These data establish that the triple toxin vaccine protects against the effect of the toxins.

In a second challenge study, for Toxin B, several constructs were produced and tested alone or in combination. Group 1 mice were administered BV1420 (30 μg) with Alum OH. Group 2 mice were administered BV1470 (30 μg) with Alum OH, Group 3 was administered a tandem protein containing rotavirus VP6 and the TcdB RBD (10 μg) with Alum OH. Group 4 mice were administered BV1470 and VP6/TcdB RBD. Group 5 was administered Toxoid B (10 μg). Group 6 was the control and was administered PBS. Anti-IgG response is shown in FIG. 15. High titers antibodies were obtained in each case. Each of the groups containing the Toxin A peptide induced high titer anti-Toxin A responses ranging between $10^4$ and about $10^5$. All groups were administered the Toxin B peptide and each demonstrated high titer ranging between $10^4$ and about $10^6$. Each of the groups containing the Binary Toxin peptide induced high titer responses ranging between $10^5$ and about $10^6$. FIG. 16 establishes that the antibodies were produced that neutralized both Toxin B, with the Toxoid B showing higher levels.

Survival of the Groups 1-6 mice is shown in FIG. 17. All mice in the PBS control Group died by Day 3, with 5 of 6 dead within one day. Toxin B survival was 100%. For groups 1 to 4, survival rates ranged from 67% to 83%.

Example 6

Additional Triple Toxin Vaccines

Additional vaccines can be produced while obtaining high expression levels. FIGS. 18 and 19 shows additional trivalent vaccine proteins with the TcdB gene translocations gene. BV1512 is shown in the bottom diagram. FIG. 18 shows additional vaccines structures: Multimer Protein Sequence: Sequence of BV1512 multimer vaccine protein showing CDTb protein separated from the Translocation Domain (TD) by an A-S linker and the TD separated from the TcdAR19 portion by an S-R linker. FIG. 19 shows expression of the multimer protein BV1512 from Sf9 cells.

Example 7

Quadrivalent Vaccines

Figure 26C:
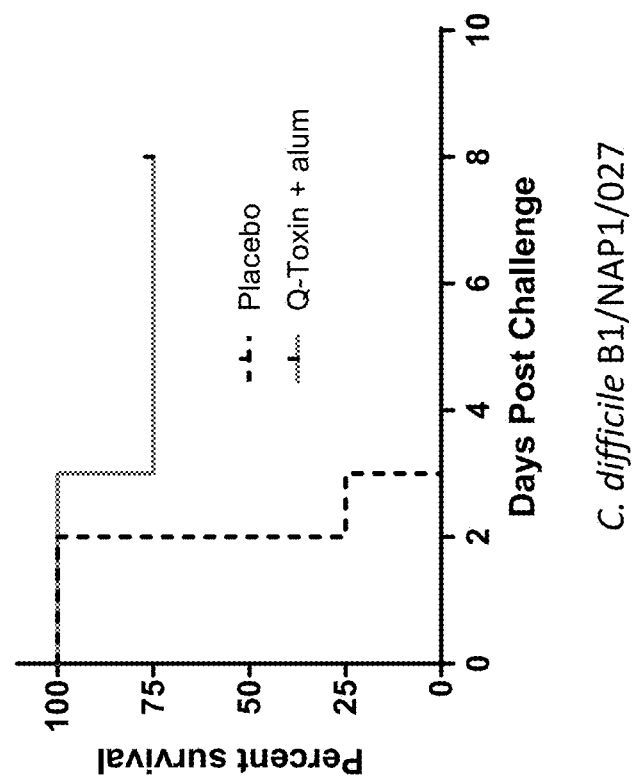
Figure 26D:
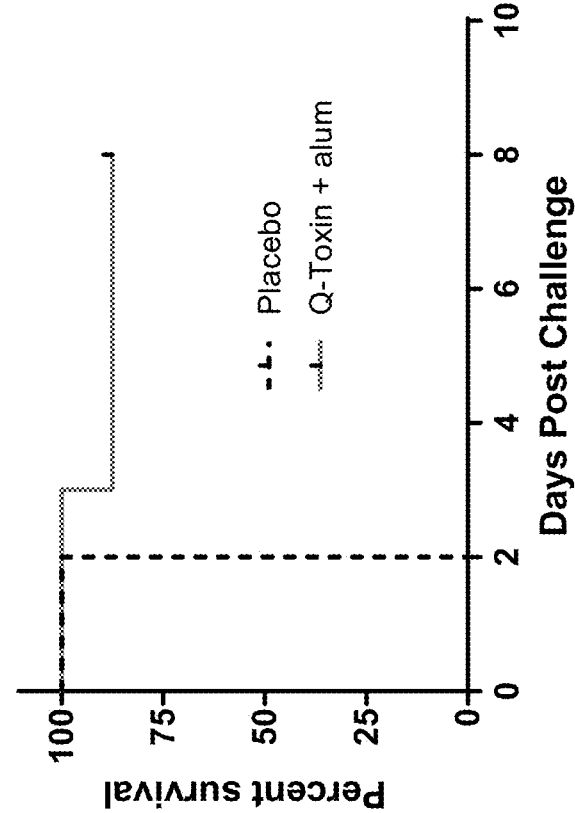

Multimer proteins containing four peptides were produced. FIG. 20. In this example, a peptide from a second TcdB strain was introduced to broaden immunity against an additional *C. difficile* strain. The first quadrivalent multimer protein (CBAB, or pCDTb/TcdB$_{630}$/TcdAR19/TcdB$_{027}$) included a TcdB peptide from Strain 027 added at the C-terminus (See FIG. 20, upper diagram). In a second quadrivalent multimer peptide, a TcdB peptide from Strain 027 peptide was introduced between the TcdB protein and the TcdA(R19) protein from the first strain, strain 630 (See FIG. 20, lower diagram). FIG. 21 shows expression of the CBBA quadrivalent multimer from Sf9 cells as described above. The data shows that the yield obtained was 42 mg/L. A second protein (CBBA, or pCDTb/TcdB$_{630}$/TcdAR19/TcdB$_{027}$ as shown in FIG. 26) was also produced in the Sf9 system and achieved 40 mg/L yield. See FIG. 22.

Example 8

Design, Expression, and Purification of T-Toxin and Q-Toxin Fusion Proteins

Chimeric fusion proteins were constructed to encode RBD of *C. difficile* TcdA, TcdB$_{(003)}$, TcdB$_{(027)}$, and CDTb. The RBD amino acid sequence for TcdA was derived from *C. difficile* strain VPI 10463 (ATCC 43255), NCBI P16154 (toxinotype 0, ribotype 003); TcdB$_{(003)}$ from strain VPI 10463 (ATCC 43255), NCBI P18177 (toxinotype 0, ribotype 003); TcdB$_{(027)}$ from strain CD196, NCBI WP_009888442.1 (toxinotype III, ribotype 027); and CDTb from strain CD196, GenBank ABS57477.1 (toxinotype III, ribotype 027).

The coding sequences for TcdA RBD (truncated with 19 of 38 repeats), TcdB$_{(003)}$ and TcdB$_{(027)}$ RBDs (24 repeats each), and CDTb were codon optimized for expression in insect cells (GenScript).

The nucleotide sequences encoding the CDTb gene fragment (amino acids 1-835), TcdA RBD (1314 base pairs [bp], 6816-8130 bp), and TcdB$_{(003)}$ RBD (1608 bp, 5493-7098 bp) were obtained by PCR amplification from the synthesized gene. PCR-amplified gene fragments were digested with restriction enzyme. CDTb with BamHI/NheI; TcdB$_{(003)}$ RBD with NheI/XbaI; and TcdA RBD with XbaI/HindIII. After digestion, the three genes were ligated into the BamH1 and HindIII sites of pFastBac1 (Invitrogen). The plasmid encoding the three RBDs was used to construct a recombinant *Autographa californica* Multiple Nuclear Polyhedrosis Virus (AcMNPV) baculovirus using the Bac-to-Bac baculovirus expression system (Invitrogen) in *Spodoptera frugiperda* (Sf9) insect cells to express the trivalent fusion protein, hereafter referred to as T-toxin (FIG. 23B).

TcdB$_{(027)}$ RBD (1608 bp, 5493-7098 bp) digested with SpeI/HinIII was fused to the C-terminus of the trivalent fusion gene to form the plasmid and baculovirus construct encoding the RBD of all four toxins, which was similarly expressed in Sf9 cells to produce the quadravalent fusion protein, hereafter referred to as Q-toxin (FIG. 23B; SEQ ID NO: 21).

The construct thus contains pCDTb: 835 amino acid from 1-835; Strain: CD196; toxinotype: III, ribotype: 027; GenBank: ABS57477.1; TcdB$_{003}$: 536 amino acid from 838-1373; NCBI: P18177, STRAIN=ATCC 4325/VPI 10463, Toxinotype 0, Ribotype: 087; TcdA: 438 amino acid from 1376-1813; NCBI: P16154, STRAIN=ATCC 4325/VPI 10463, Toxinotype 0; Ribotype: 087, and TcdB$_{027}$: 536 amino acid from 1815-2351; NCBI: 013315, strain CD196; toxinotype: III, ibotype: 027. Each of the portion is separated by a two amino acid linker: AS between the pCDTb portion and the TcdB003 portion, SR between the TcdB003 portion and the TcdA portion, TS between the TcdA portion and the TcdB027 portion.

Fusion proteins were extracted by detergent lysis in a buffer comprising 0.2% Tergitol NP-9 in 25 mM Tris buffer (pH 8.0), 250 mM NaCl and 2 µg/mL leupeptin. Lysates were purified by centrifugation, and the fusion proteins were purified with Fractogel EMD TMAE, phenyl HP and 30Q column chromatography. Purified T-toxin and Q-toxin were formulated in 25 mM Tris and 250 mM NaCl (pH 8.0) at approximately 4.0 mg/mL and stored at <-60° C. Recovery of purified T-toxin and Q-toxin was 267 and 154 mg/L, respectively. T-toxin and Q-toxin migrate in SDS-PAGE gels with molecular weights of 205 kDa and 268 kDa, respectively, and purity of >90% (FIG. 23A). Western blot analysis with toxin-specific antibodies confirmed expression of CDTb, TcdB, and TcdA in each fusion protein (FIG. 23B-D).

Example 9

Immunogenicity of T-Toxin and Q-Toxin Fusion Proteins in Mice

To evaluate immunogenicity of T-toxin and Q-toxin fusion proteins, Mouse studies were conducted in accordance with Noble Life Sciences' Institutional Animal Care and Use Committee (IACUC) approved protocols. Female C57BL/6 mice (6-8 weeks old) were immunized IM on Days 0 and 14 with T-toxin (30 or 100 µg) or Q-toxin (100 µg) formulated with 50 µg aluminum hydroxide (alum), or PBS (control). Serum was collected 18 days after the second dose. Mice were challenged intraperitoneally (IP) 3 weeks after the second immunization with a 100% minimal lethal dose (MLD$_{100\%}$) of TcdA, TcdB$_{(003)}$, or CDTa and CDTb.

Mouse sera was evaluated for antibodies to the toxins by ELISA. A 96-well MaxiSorp microtiter plates (Thermo Scientific) were coated with each toxin (2 µg/mL) overnight at 2-8° C. Five-fold serial dilutions of sera were added to plates in duplicate. Bound antibodies were detected with horseradish peroxidase-conjugated goat anti-mouse IgG (Southern Biotech). 3,3',5,5'-tetramethylbenzidine (TMB) substrate (Sigma) was added and the reaction stopped with TMB Stop Buffer (Scytek Laboratories). Plates were read at 450 nm with a SpectraMax Plus plate reader (Molecular Devices); results were analyzed using SoftMax Pro software. Titers were reported as the reciprocal dilution that resulted in a reading of 50% the maximum OD$_{450nm}$. Titer values recorded as below the lower limit of detection (LLOD) were assigned a titer 50 for calculating GMT. Mouse serum IgG titers following immunization were high for TcdA, TcdB, and CDT and comparable between T-toxin and Q-toxin (FIG. 25A).

Vero cells (CCL-81, ATCC) were maintained in DMEM supplemented with 20% heat-inactivated fetal bovine serum (FBS) and antibiotics (Gibco). Two-fold serial dilutions of mouse sera were prepared in 96-well, flat-bottom tissue culture plates (Thermo Scientific). An equal volume (50 µL) of assay medium (1x DMEM with 5% heat-inactivated FBS, 1×NEAA, 0.3% dextrose, 1× penicillin/streptomycin/glutamine, 0.006% Phenol Red) containing 2× minimum cytotoxic dose of TcdA, TcdB, or CDT was added to diluted serum and incubated for 1 hour at 37° C. Vero cells (7.5×10$^4$ cells/mL) suspended in 50 µL medium and 150 µL sterile mineral oil (Sigma) were added and plates were incubated for 6-7 days at 37° C. After incubation, plates were observed for well color. Media and toxin-treated control wells were red/reddish-pink; cell control wells were yellow/yellow-orange. For each sample dilution, the last well that was yellow/yellow-orange was recorded as the endpoint neutralizing-antibody titer. Titer values recorded as <LLOD were assigned a value of 5 for calculating GMT. Toxin-neutralizing antibody (TNA) titers to each of the three toxins were comparable between the T-toxin and Q-toxin fusion proteins (FIG. 25B).

Three weeks after the second immunization, mice were challenged TcdB$_{(003)}$. The group vaccinated with Q-toxin had 80% survival (p=0.0043), while 65% (p=0.018) of the T-toxin group survived challenge. In contrast, only 20% survived toxin challenge in the control group (FIG. 25C).

Example 10

Immunogenicity of T-Toxin and Q-Toxin Fusion Proteins in Hamsters

Golden Syrian hamsters (HsdHan:Aura; Harlan Laboratories), males aged 5-7 weeks and 70 to 100 grams, received 3 immunizations at 3-week intervals with 30 μg Q-toxin and 120 μg alum, or PBS (control), administered IM in alternating thighs. Two weeks after the third immunization serum was collected and animals were treated with 10 mg/kg clindamycin IP. One day later, animals were challenged by gavage with strain 630 or NAP1 and were observed for 8 days.

Hamster sera was evaluated for antibodies to the toxins by ELISA. A 96-well MaxiSorp microtiter plates (Thermo Scientific) were coated with each toxin (2 μg/mL) overnight at 2-8° C. Five-fold serial dilutions of sera were added to plates in duplicate. Bound antibodies were detected with horseradish peroxidase-conjugated rabbit anti-hamster IgG (Southern Biotech). 3,3',5,5'-tetramethylbenzidine (TMB) substrate (Sigma) was added and the reaction stopped with TMB Stop Buffer (Scytek Laboratories). Plates were read at 450 nm with a SpectraMax Plus plate reader (Molecular Devices); results were analyzed using SoftMax Pro software. Titers were reported as the reciprocal dilution that resulted in a reading of 50% the maximum $OD_{450nm}$. Titer values recorded as below the lower limit of detection (LLOD) were assigned a titer 50 for calculating GMT. Hamsters immunized thrice at 3-week intervals with Q-toxin produced high IgG titers to the TcdA, TcdB, and CDTb toxins (FIG. 26A).

Vero cells (CCL-81, ATCC) were maintained in DMEM supplemented with 20% heat-inactivated fetal bovine serum (FBS) and antibiotics (Gibco). Two-fold serial dilutions of hamster sera were prepared in 96-well, flat-bottom tissue culture plates (Thermo Scientific). An equal volume (50 μL) of assay medium (lx DMEM with 5% heat-inactivated FBS, 1×NEAA, 0.3% dextrose, 1× penicillin/streptomycin/glutamine, 0.006% Phenol Red) containing 2× minimum cytotoxic dose of TcdA, TcdB, or CDT was added to diluted serum and incubated for 1 hour at 37° C. Vero cells (7.5-10$^4$ cells/mL) suspended in 50 μL medium and 150 μL sterile mineral oil (Sigma) were added and plates were incubated for 6-7 days at 37° C. After incubation, plates were observed for well color. Media and toxin-treated control wells were red/reddish-pink; cell control wells were yellow/yellow-orange. For each sample dilution, the last well that was yellow/yellow-orange was recorded as the endpoint neutralizing-antibody titer. Titer values recorded as <LLOD were assigned a value of 5 for calculating GMT. TNA titers to each of the three toxins were comparable between the T-toxin and Q-toxin fusion proteins (FIG. 31B).

After clindamycin treatment, animals infected with *C. difficile* strain 630 had 90% survival (FIG. 26C), while animals infected with NAP1 had 75% survival (FIG. 31D). All animals in the placebo group died within 48-72 hours following infection with either strain.

INCORPORATION BY REFERENCE

Each of the patents and published applications identified herein are incorporated herein for all purposes.

The invention claimed is:

1. A multivalent immunogenic polypeptide comprising
    (i) a binary toxin (CDT) portion having an amino acid sequence that compises SEO ID NO: 22 or an amino acid sequence having at least 90% homology to SEQ ID NO: 22;
    (ii) a Toxin A portion having an amino acid sequence that comprises SEQ ID NO:24 or an amino acid sequence having at least 90% homology to SEQ ID NO: 24;
    (iii) a first Toxin B portion having an amino acid sequence that comprises SEQ ID NO: 23 or an amino acid sequence having at least 90% homology to SEQ ID NO: 23; and
    (iv) a second Toxin B portion having an amino acid sequence that comprises SEO ID NO: 25 or an amino acid sequence having at least 90% homology to SEQ ID NO: 25;
    wherein each portion is from a *C. difficile* toxin protein.

2. The multivalent immunogenic polypeptide of claim 1, wherein the Toxin A portion is between the two Toxin B portions.

3. The multivalent immunogenic polypeptide of claim 1, wherein the CDT portion is N-terminal to one or both of the Toxin B portions.

4. The multivalent immunogenic peptide of claim 1, wherein each portion is separated by a two amino acid linker, a three amino acid linker, or a four amino acid linker.

5. The multivalent immunogenic peptide of claim 4, wherein the portions are separated by a two amino acid linker and the linker is selected from the group consisting of Alanine-Serine (AS), Leucine-Glutamic acid (LE), and Serine-Arginine (SR).

6. The multivalent immunogenic polypeptide of claim 1, wherein the polypeptide comprises an amino acid sequence that is at least 95% homologous to SEQ ID NO: 21.

7. The multivalent immunogenic polypeptide of claim 1, wherein the polypeptide comprises an amino acid sequence that is at least 97% homologous to SEQ ID NO: 21.

8. The multivalent immunogenic polypeptide of claim 1, wherein the polypeptide comprises an amino acid sequence that is at least 99% homologous to SEQ ID NO: 21.

9. The multivalent immunogenic polypeptide of claim 1, wherein:
    (i) the CDT portion has an amino acid sequence that is at least 95% homologous to SEQ ID NO: 22;
    (ii) the Toxin A portion has an amino acid sequence that is at least 95% homologous to SEQ ID NO: 24;
    (iii) the first Toxin B portion has an amino acid sequence that is at least 95% homologous to SEQ ID NO: 23; and
    (iv) the second Toxin B portion has an amino acid sequence that is at least 95% homologous to SEQ ID NO: 25.

10. The multivalent immunogenic polypeptide of claim 1, wherein:
    (i) the CDT portion has an amino acid sequence that is at least 97% homologous to SEQ ID NO: 22;
    (ii) the Toxin A portion has an amino acid sequence that is at least 97% homologous to SEQ ID NO: 24;
    (iii) the first Toxin B portion has an amino acid sequence that is at least 97% homologous to SEQ ID NO: 23; and
    (iv) the second Toxin B portion has an amino acid sequence that is at least 97% homologous to SEQ ID NO: 25.

11. The multivalent immunogenic polypeptide of claim 1, wherein:
    (i) the CDT portion has an amino acid sequence that is at least 98% homologous to SEQ ID NO: 22;
    (ii) the Toxin A portion has an amino acid sequence that is at least 98% homologous to SEQ ID NO: 24;
    (iii) the first Toxin B portion has an amino acid sequence that is at least 98% homologous to SEQ ID NO: 23; and
    (iv) the second Toxin B portion has an amino acid sequence that is at least 98% homologous to SEQ ID NO: 25.

12. A nucleic acid molecule, comprising a polynucleotide encoding the polypeptide of claim 1.

13. A method of preparing the polypeptide of claim 1, comprising:
    (a) expressing the polypeptide in an insect host cell,
    (b) isolating, the polypeptide from. the insect host cell in the presence of a non-ionic detergent.

14. The method of claim 13, wherein the insect host is an Sf9 cell.

15. The method of claim 13, wherein the insect host cell is transfected with a recombinant baculovirus construct under suitable conditions for expression of the polypeptide.

16. An immunogenic composition comprising the immunogenic polypeptide of claim 1, and a pharmaceutically acceptable carrier, excipient, or diluent.

17. The immunogenic composition of claim 16, wherein the composition comprises an adjuvant.

18. The immunogenic composition of claim 16, wherein the adjuvant is a saponin-based adjuvant.

19. The immunogenic composition of claim 16, wherein the saponin-based adjuvant contains Fraction A Matrix and Fraction C Matrix.

20. The immunogenic composition of claim 19, wherein the amount of Fraction A Matrix is about 85% to about 92% by weight and the remainder is Fraction C Matrix.

* * * * *